US007179912B2

(12) United States Patent
Halbrook et al.

(10) Patent No.: US 7,179,912 B2
(45) Date of Patent: Feb. 20, 2007

(54) MATERIALS AND METHODS TO POTENTIATE CANCER TREATMENT

(75) Inventors: James Halbrook, Woodinville, WA (US); Edward A. Kesicki, Bothell, WA (US); Laurence E. Burgess, Boulder, CO (US); Stephen T. Schlachter, Boulder, CO (US); Charles T. Eary, Longmont, CO (US); Justin G. Schiro, Firestone, CO (US); Hongmei Huang, Broomfield, CO (US); Michael Evans, Louisville, CO (US); Yongxin Han, Longmont, CO (US)

(73) Assignee: ICOS Corporation, Bothell, WA (US)

( * ) Notice: Subject to any disclaimer, the term of this patent is extended or adjusted under 35 U.S.C. 154(b) by 0 days.

(21) Appl. No.: 09/941,897

(22) Filed: Aug. 28, 2001

(65) Prior Publication Data

US 2002/0165218 A1 Nov. 7, 2002

Related U.S. Application Data

(60) Provisional application No. 60/229,899, filed on Sep. 1, 2000.

(51) Int. Cl.
*C07D 265/30* (2006.01)
*C07D 295/02* (2006.01)

(52) U.S. Cl. ........................ 544/106; 544/178
(58) Field of Classification Search ............... 544/175, 544/106, 178
See application file for complete search history.

(56) References Cited

U.S. PATENT DOCUMENTS

| | | | | |
|---|---|---|---|---|
| 3,904,631 A | | 9/1975 | Elslager et al. | |
| 4,003,699 A | * | 1/1977 | Rose et al. | 8/409 |
| 4,161,589 A | | 7/1979 | Baumann et al. | |
| 4,410,708 A | * | 10/1983 | Yahagi et al. | 548/407 |
| 4,451,462 A | | 5/1984 | Wenk et al. | |
| 4,539,412 A | | 9/1985 | Archer | |
| 4,558,043 A | | 12/1985 | Wenk et al. | |
| 4,904,798 A | * | 2/1990 | Kranz et al. | 548/472 |
| 5,401,739 A | | 3/1995 | Ohno et al. | |
| 6,174,887 B1 | | 1/2001 | Haruta et al. | |
| 6,297,242 B1 | | 10/2001 | Hlasta | |
| 6,407,092 B1 | | 6/2002 | Hester et al. | |
| 6,555,593 B1 | | 4/2003 | Hoyle et al. | |
| 6,589,984 B1 | | 7/2003 | Naniwa et al. | |

2001/0027210 A1 10/2001 Wilson

FOREIGN PATENT DOCUMENTS

| | | |
|---|---|---|
| DE | 27 37 207 A1 | 3/1979 |
| DE | 29 22 488 A | 12/1980 |
| DE | 29 50 291 A1 | 6/1981 |
| DE | 31 41 970 A1 | 5/1983 |
| DE | 44 24 712 A | 1/1996 |
| EP | 0 078 241 A | 5/1983 |
| EP | 0 106 800 A | 4/1984 |
| EP | 0 107 620 A | 5/1984 |
| EP | 0 342 665 A | 11/1989 |
| EP | 0 471 516 A1 | 2/1992 |
| FR | 1 355 173 A | 3/1964 |
| FR | 8 298 M | 11/1970 |
| GB | 2109373 * | 2/1983 |
| GB | 2326410 A | 12/1998 |
| JP | 55-44830 | 3/1980 |
| JP | 11 106371 A | 4/1999 |
| JP | 11-199565 | 7/1999 |
| JP | 2002-97382 | 4/2002 |
| WO | WO 90/14008 A1 | 11/1990 |
| WO | WO 92/16517 A1 | 10/1992 |
| WO | WO 92/20666 A | 11/1992 |
| WO | WO 95/20652 A | 8/1995 |
| WO | WO 96/16632 A1 | 6/1996 |
| WO | WO 96/22077 A1 | 7/1996 |
| WO | WO 97/08133 A | 3/1997 |
| WO | WO 97/31891 A | 9/1997 |
| WO | WO 98/13502 A | 4/1998 |
| WO | WO 99/14212 | 3/1999 |
| WO | WO 99/29705 A | 6/1999 |
| WO | WO 99/39247 A1 | 8/1999 |
| WO | WO 99/46262 | 9/1999 |
| WO | WO 00/00644 A | 1/2000 |
| WO | WO 00/17386 A | 3/2000 |
| WO | WO 00/18750 | 4/2000 |
| WO | WO 01/17985 A1 | 3/2001 |
| WO | WO 02/20500 A2 | 3/2002 |

OTHER PUBLICATIONS

Eiden et al. (Archiv der Pharmazie (Weinheim, Germany) (1985), 318(4), 328-40).*
Brown et al. (Can. J. Research (1948), 26D, 177-87). Abstract.*

(Continued)

*Primary Examiner*—Bruck Kifle
(74) *Attorney, Agent, or Firm*—Wolf, Greenfield & Sacks, P.C.

(57) ABSTRACT

Compounds that inhibit DNA-dependent protein kinase, compositions comprising the compounds, methods to inhibit the DNA-PK biological activity, methods to sensitize cells the agents that cause DNA lesions, and methods to potentiate cancer treatment are disclosed.

7 Claims, No Drawings

OTHER PUBLICATIONS

Gilman et al. (Journal of the American Chemical Society (1952), 74, 3027-9). Abstract.*
Cretcher et al. (Journal of the American Chemical Society (1925), 47, 163-6).*
Elslager et al. (Journal of Medicinal Chemistry (1970), 13(3), 370-376).*
Langer et al. (Monatshefte fuer Chemie (1959), 90, 623-33). Abstract.*
Effenberger et al. (Chemische Berichte (1972), 105(6), 1926-42). Abstract.*
Izzard et al., *J. Cancer Research*, 59, pp. 2581-2586 (1999).
Russell et al., *J. Cancer Research*, 55, pp. 1639-1642 (1995).
Powell et al., *J. Cancer Research*, 55, pp. 1643-1648 (1995).
Araki et al., *Proc. Natl. Acad. Sci., USA*, vol. 94, pp. 2438-2443 (1997).
Blunt et al., *Proc. Natl. Acad. Sci., USA*, vol. 93, pp. 10285-10290 (1996).
Peterson et al., *Proc. Natl. Acad. Sci., USA*, vol. 92, pp. 3171-3174 (1995).
Blunt et al., *Cell*, vol. 80, pp. 813-823 (1995).
Biedermann et al., *Proc. Natl. Acad. Sci., USA*, vol. 88, pp. 1394-1397 (1991).
Hendrickson et al., *Proc. Natl. Acad. Sci., USA*, vol. 88, pp. 4061-4065 (1991).
Fulop et al., *Nature*, vol. 347, pp. 479-482 (1990).
Christodouopoulos et al., *Cancer Research*, 58, pp. 1789-1792 (1998).
Jackson, *Int. J. Biochem. Cell Biol.*, vol. 29, No. 7, pp. 935-938 (1997).
Daniel et al., *Science*, vol. 284, pp. 644-647 (1999).
M. Windholz (Ed.) et al., "The Merck Index, ninth edition," p. 84, No. 658; p. 159, No. 1229; p. 187, No. 1458; p. 193, No. 1500; p. 263, No. 2050; p. 474, No. 3550; p. 680, No. 5043; p. 847, No. 6342; p. 871, No. 6521; p. 936, No. 7009; p. 939, No. 7031; p. 1069, No. 8011; p. 1080, No. 8094; p. 1275, No. 9592; 1976, Rahway, N. J.
Abadi, A.H., et al., "Synthesis, Antitumor and Antitubercular Evaluation of Certain New Xanthenone and Acridinone Analogs," *Arzneim.-Forsch./Drug Res.* 49 (I), Nr. 3, pp. 259-266 (1999).

Agasimundin, Y.S., et al., "Furano compounds. XX. Synthesis of angular and linear furoxanthones," *Journal fuer Praktische Chemie* (Leipzip) (1972), 314(3-4), pp. 507-514, Abstract.
Croisy-Delcey, M., et al., "Aza Analogues of Lucanthone: Synthesis and Antitumor and Bactericidal Properties," *J. Med. Chem.* (1983), 26, pp. 1329-1333.
Fonteneau, N., et al., "Synythesis of quinone and xanthone analogs of rhein," *Tetrahedron* 57 (2001) pp. 9131-9135.
Fujioka, H., et al., "Activities of New Acridone Alkaloid Derivatives against Plasmodium yoelii in vitro," *Arzneim.-Forsch./Drug Res.* 40 (II), Nr. 9 (1990), pp. 1026-1029.
Ghosh, C.K., et al., "Benzopyrans. Part 30. Synthesis of Substituted Xanthones from 3-Acyl-2-methyl-1-benzopyran-4-ones," *Tetrahedron* vol. 49, No. 19, pp. 4127-4134, 1993.
Goud, A.N., et al., "Furan compounds. XVI," *Monatsh. Chem.* (1969), 100(1), pp. 38-41, Abstract.
Harfenist, M., et al., "Selective Inhibitors of Monoamine Oxidase. 3. Structure-Activity Relationship of Tricyclics Bearing Imidazoline, Oxadiazole, or Tetrazole Groups," *J. Med. Chem.* 1996, 39, pp. 1857-1863.
Klopman, G., et al., "An artificial intelligence approach to the study of the structural moieties relevant to drug-receptor interactions in aldose reductase inhibitors," *Molecular Pharmacology* (1988), 34(6), pp. 852-862, Abstract.
Mari, S., et al., "Flavone and xanthone derivatives related to fluoroquinolones," *Il Farmaco* 54 (1999) pp. 411-415.
Tabarrini, O., et al., "Design and Synthesis of Modified Quinolones as Antitumoral Acridones," *J. Med. Chem.*, 1999, vol. 42, No. 12, pp. 2136-2144.
Xuan, T., et al., "Two new O-and C-glycosylxanthones from the Gentiana tizuensis Franch," *Gaodeng Xuexiao Huaxue Xuebao* (2001), 22(10, Suppl.), pp. 148-150, Abstract.
Effenberge, F. et al., "Aminobenzenes. VIII. Rearrangement of phenyl carbamates. Syntheses of 2,4-dioxo-3,4-dihydro-2H-1,3-benzoxazines and salicylamides," Chemische Berichte 1972, 105(6), 1926-42.

* cited by examiner

MATERIALS AND METHODS TO POTENTIATE CANCER TREATMENT

CROSS-REFERENCE TO RELATED APPLICATION

This application claims the benefit of provisional U.S. Patent Application No. 60/229,899, filed Sep. 1, 2000.

FIELD OF THE INVENTION

The present invention relates to inhibitors of DNA-dependent protein kinase (DNA-PK), and to methods of using the inhibitors to potentiate cancer treatment.

BACKGROUND OF THE INVENTION

All cells possess mechanisms to maintain integrity of the cellular genome through detection and repair of, for example, adduct formation, cross-linking, single-strand breaks, and double-strand breaks. The mechanisms of detection and damage repair, collectively, are called DNA repair. DNA repair functions are carried out on lesions that arise from exposure to a variety of environmental chemical and physical agents, as well as from toxic agents generated intracellularly in normal cellular metabolism. Because DNA provides the information required for cell, tissue, and organism function, a large amount of cellular energy is devoted to maintaining intact structure of the genome.

The most genotoxic damages are those which induce DNA chain disruptions, particularly double-strand breaks. DNA double-strand breaks (dsbs) can be induced by chemical or physical agents, including intercalating agents, electrophilic compounds and ionizing radiation. At least two pathways responsible for the repair of DNA dsbs exist, i.e., homologous recombination (HR) and nonhomologous end joining (NHEJ). The former reaction requires undamaged DNA from the homologous chromosome to be used as a template in the repair of the DNA discontinuity. NHEJ, in contrast, is DNA homology independent and simply requires two free DNA ends to be re-ligated. The exact molecular mechanisms by which both HR and NHEJ are effected remain to be elucidated.

DNA dsbs also are generated during the course of normal cellular development in some tissues. This observation first was appreciated following the discovery and characterization of the severe combined immuno-deficiency (scid) mouse. The scid syndrome is a genetic disorder which manifests as an absence of B- and T-cell immunity (Bosma et al., *Nature*, 301:527–530 (1983), and reviewed in Bosma and Carroll, *Annu. Rev. Immunol.*, 9:323–350 (1991)). The scid mouse is defective in the earliest stages of lymphoid cell development as a result of an inability to correctly rearrange T-cell receptor (TCR) and IgM μ chain DNA (Bosma and Carroll, *Annu. Rev. Immunol.*, 9:323–350 (1991), Dorshkind et al., *J. Immunol.*, 132:1804–1808 (1984), Lauzon et al., *J. Exp. Med.*, 164:1797–1802 (1986), Schuler et al., *Cell*, 46:963–972 (1986), Tutt et al., *J. Immunol.*, 138:2338–2344 (1987), Lieber et al., *Cell*, 55:7–16 (1988)). As a result, T- and B-cells do not progress beyond the $CD25^+$ $CD4^-$ $CD8^-$ and $CD25^-$ pro-B cell stages, respectively. Site-specific V(D)J recombination is initiated in scid mice through the activity of the RAG1 and RAG2 gene products, however, resolution of recombination intermediates is disrupted (Fulop and Phillips, *Nature*, 347:479–482 (1990), Biedermann et al., *Proc. Natl. Acad. Sci. USA*, 88:1394–1397 (1991), Hendrickson et al., *Proc. Natl. Acad. Sci. USA*, 88:4061–4065 (1991), Oettinger et al., *Science*, 248:1517–1522 (1990), Mombaerts et al., *Cell*, 68:869–877 (1992), Shinkai et al., *Cell*, 68:855–867 (1992), van Gent et al., *Cell*, 81:925–934 (1995), and reviewed in Lieber, *FASEB J.*, 5:2934–2944 (1991)). Nonproductive rearrangements in scid cells typically result in large deletions at the TCR and Ig loci, while the processing of recombination signal sequences is not affected in these cells. The scid mutation, therefore, specifically disrupts the formation of recombinant coding junctions (Lieber et al., *Cell*, 55:7–16 (1988), Malynn et al., *Cell*, 54:453–460 (1988)).

The defect in the scid mouse is caused by mutation of the gene encoding the catalytic subunit of the DNA-dependent protein kinase (DNA-PK) (Blunt et al., *Cell*, 80:813–823 (1995), Peterson et al., *Proc. Natl. Acad. Sci. USA*, 92:3171–3174 (1995)). Specifically, a nonsense mutation at tyrosine-4046 results in the deletion of the last 83 amino acid residues (Blunt et al., *Proc. Natl. Acad. Sci. USA*, 93:10285–10290 (1996), Danska et al., *Mol. Cell. Biol.*, 16:5507–5517 (1996), Araki et al., *Proc. Natl. Acad. Sci. USA*, 94:2438–2443 (1997)).

DNA-PK is a trimeric complex composed of a p460 catalytic subunit and Ku80 (86 kDa) and Ku70 regulatory proteins. Ku70 and Ku80 were initially described as human autoantigens and function as cofactors in vitro stimulating protein kinase activity through binding DNA (Mimori, *J. Clin. Invest.*, 68:611–620 (1981), Dvir et al., *Proc. Natl. Acad. Sci. USA*, 89:11920–11924 (1992), Gottlieb and Jackson, *Cell*, 72:131–142 (1993)). Ku70 and Ku80 exhibit highest affinity for DNA duplex termini and gaps (Blier et al., *J. Biol. Chem.*, 268:7594–7601 (1993), Falzon et al., *J. Biol. Chem.*, 268: 10546–10552 (1993)). Although, the precise function of DNA-PK and its natural substrates remain unknown, this enzyme phosphorylates a number of proteins in vitro, including many transcription factors and p53 (Lees-Miller et al., *Mol. Cell. Biol.*, 12:5041–5049 (1992), Anderson and Lees-Miller, *Crit. Rev. Euk. Gene Exp.*, 2:283–314 (1992)).

Cultured scid cells are sensitive to killing by agents that induce DNA double-strand breaks (dsbs), indicating a role for DNA-PK in the repair of these lesions. The scid defect also sensitizes mice to radiation-induced lymphomagenesis (Lieberman et al., *J. Exp. Med.*, 176:399–405 (1992)). Lymphomas arise in scid mice at frequencies ranging from 50 to 100% at x-ray doses that do not affect wild-type mice. Since unirradiated scid mice are not particularly sensitive to lymphomagenesis, the background level of tumor-inducing dsbs must either be low enough to be effectively repaired or the damaged cells are effectively eliminated.

The therapeutic benefit of radiation and chemotherapy in the treatment of cancer is well documented. These physical and chemical agents act by disrupting DNA metabolism at the level of DNA structure, synthesis, transcription and chromosome transmission. Most of these agents act by inducing DNA-specific lesions. Presumably, if tumor cells are sensitive to therapies that introduce DNA specific lesions, then these therapies will be made more effective by simultaneously disrupting the cellular repair of these damages. Therefore, inhibition of cellular DNA-PK activity following treatment with agents that induces DNA dsbs will potentiate the therapeutic index of these agents.

Thus, there exists a need in the art to identify compounds that can improve the efficiency of radiation and chemotherapy in treatment of cancer. Identification of DNA-PK inhibitors can permit development of treatment regimens that include lower doses of radiation and/or chemotherapy drugs, thereby reducing the unwanted side effects that often accompany the treatments.

SUMMARY OF THE INVENTION

The invention provides compounds having a DNA-PK inhibiting activity. The present DNA-PK inhibitors can be used in diagnostic and therapeutic methods useful in the field of cancer therapy. More particularly, the DNA-PK inhibitors permit development of compositions and treatment regimens that can be used with doses of radiation and/or chemotherapy drugs lower than a standard prescribed dose. The reduced exposure to radiation and chemotherapy drugs improves a patient's prognosis with regard to unwanted adverse side effects that often accompany cancer treatments.

The DNA-PK inhibitors of the invention are compounds having a formula (I):

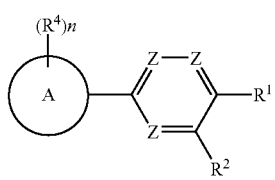

(I)

or a pharmaceutically acceptable salt thereof, wherein:

n is an integer 0 through 4;

Z, independently, is $CR^3$ or N;

A is an optionally substituted four- to seven-membered aliphatic ring containing 0, 1, 2, or 3 heteroatoms, independently selected from the group consisting of N, O, and S;

$R^1$ is selected from the group consisting of hydrogen, alkyl, substituted alkyl, cycloalkyl, heterocycloalkyl, $N(R^h)_2$, $OR^h$, carboxyl, carboxy, nitro, hydrazono, hydroxyamino, cyano, aldehyde, carboxarmide, thiocarboxamide, acyl, mercapto, sulfonyl, trifluoromethyl, heteroaryl, and substituted heteroaryl;

$R^2$ is selected from the group consisting of hydrogen, alkyl, substituted alkyl, carbamoyl, carboxamide, $N(R^h)_2$, carboxy, $OR^h$, sulfamyl, nitro, phosphate, and sulfonamido; or $R^1$ and $R^2$ are taken together with the carbon atoms to which each is attached to form a 5-, 6-, or 7-membered ring, wherein 1, 2, or 3 carbon atoms of $R^1$ and $R^2$ optionally are a heteroatom selected from the group consisting of O, N, S, and P, said ring optionally substituted with one or more =O, =S, =NH, $OR^b$, $N(R^h)_2$, carboxyl, carboxy, alkyl, aryl, substituted aryl, heteroaryl, or substituted heteroaryl, said heteroatom optionally substituted with a group selected from the group consisting of aryl, substituted aryl, alkyl, alkyl substituted with acyl, and acyl;

$R^3$, independently, is selected from the group consisting of hydrogen, halo, aldeyhde, $OR^h$, nitro, $N(R^h)_2$, carboxyl, carboxy, sulfonamido, sufamyl, and sulfo or a halide derivative thereof, wherein $R^h$, independently, is selected from the group consisting of hydrogen, alkyl, substituted alkyl, cycloalkyl, aryl, substituted aryl, heteroaryl, and substituted heteroaryl; and $R^4$, independently, is selected from the group consisting of $OR^h$, halo, $N(R^h)_2$, aldehyde, alkyl, substituted alkyl, acyl, aryl, substituted aryl, heteroaryl, and substituted heteroaryl;

with the proviso that when A is morpholinyl, $R^2$ and $R^4$ are hydrogen, and $ZR^3$ is CH at each occurrence, then $R^1$ is different from —(CO)—$CH_3$, (C=$CH_2$)-phenyl, and nitro; and with the proviso that when A is morpholinyl, $R^4$ is hydrogen, and Z is nitrogen at each occurrence, then $R^1$ and $R^2$, when taken together, is different from triazole.

Additional compounds useful as DNA-PK inhibitors have a structural formula (II):

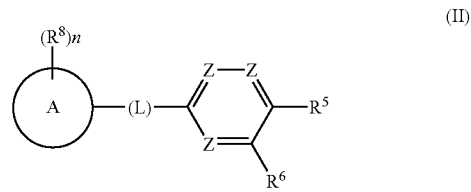

(II)

or a pharmaceutically acceptable salt thereof, wherein:

Z, independently, is $CR^7$ or N;

L is selected from the group consisting of alkylene, substituted alkylene, carbonyl, carbamoyl, $NR^h$, oxy (—O—), thio (—S—), thionyl (—SO—), and sulfonyl;

A is absent, or A is an optionally substituted four- to seven-membered aliphatic ring containing 0, 1, 2, or 3 heteroatoms, independently selected from the group consisting of N, O, and S;

$R^5$ is selected from the group consisting of hydrogen, alkyl, substituted alkyl, cycloalkyl, heterocycloalkyl, $N(R^h)_2$, $OR^h$, carboxyl, carboxy, nitro, hydrazono, hydroxyamino, cyano, aldehyde, carboxamide, thiocarboxamide, acyl, mercapto, sulfonyl, trifluoromethyl, heteroaryl, and substituted heteroaryl;

$R^6$ is selected from the group consisting of hydrogen, alkyl, substituted alkyl, carbamoyl, carboxamide, $N(R^h)_2$, carboxy, $OR^h$, sulfamyl, nitro, phosphate, and sulfonamido; or $R^5$ and $R^6$ are taken together with the carbon atoms to which each is attached to form a 5-, 6-, or 7-membered ring, wherein 1, 2, or 3 carbon atoms of $R^5$ and $R^6$ optionally are a heteroatom selected from the group consisting of O, N, S, and P, said ring optionally substituted with one or more of =O, =S, =NH, $OR^h$, $N(R^h)_2$, carboxyl, carboxy, alkyl, aryl, substituted aryl, heteroaryl, or substituted heteroaryl, and said heteroatom optionally substituted with a substituent selected from the group consisting of aryl, substituted aryl, alkyl, alkyl substituted with acyl, and acyl;

$R^7$, independently, is selected from the group consisting of hydrogen, halo, aldehyde, $OR^h$, nitro, $N(R^h)_2$, carboxyl, carboxy, sulfamyl, sulfonamido, and sulfo or a halide derivative thereof, wherein $R^h$, independently, is selected from the group consisting of hydrogen, alkyl, substituted alkyl, cycloalkyl, aryl, substituted aryl, heteroaryl, and substituted heteroaryl; and $R^8$, independently, is selected from the group consisting of $OR^h$, halo, $N(R^h)_2$, aldehyde, alkyl, substituted alkyl, acyl, aryl, substituted aryl, heteroaryl, and substituted heteroaryl.

The invention further provides a pharmaceutical composition comprising (a) one or more DNA-PK inhibitors of formula (I) or (II) and (b) a pharmaceutically acceptable carrier. The pharmaceutical composition optionally comprises an anti-neoplastic agent.

The invention also provides pharmaceutical compositions comprising (a) one or more DNA-PK inhibitors of formula (I) or (II) and (b) a radiotherapeutic (or anti-neoplastic agent). Radiotherapeutic agents include compounds that can be targeted to neoplastic cell types and include one or more attached radioisotopes.

The invention also provides methods of inhibiting DNA-PK activity. The method comprises the step of contacting a DNA-PK with one or more compounds of formula (I) or (II).

The invention further provides methods of sensitizing a cell to an agent that induces a DNA lesion comprising the step of contacting the cell with one or more DNA-PK inhibitors of formula (I) or (II). In one aspect, the agent that induces a DNA lesion is selected from the group consisting of radiation, exogenous chemicals, metabolite by-products, and combinations thereof The invention further provides methods of potentiating a therapeutic regimen for treatment of cancer comprising the step of administering to an individual in need thereof an effective amount of a DNA-PK inhibitor of formula (I) or (II). In one aspect, methods include those wherein the therapeutic regimen for treatment of cancer is selected from the group consisting of chemotherapy, radiation therapy, and a combination of chemotherapy and radiation therapy. In methods wherein the therapeutic regimen includes chemotherapy, the DNA-PK inhibitor is administered before, concurrently with, and/or after administration of the chemotherapeutic agent. The therapeutic regimen also further can include any other conventional or experimental therapy, including for example, nutritional and/or surgical techniques.

The invention also provides methods of characterizing the potency of a test compound as an inhibitor of a DNA-PK polypeptide, said method comprising the steps of: (a) measuring activity of a DNA-PK polypeptide in the presence of a test compound; (b) comparing the activity of the DNA-PK polypeptide in the presence of the test compound to the activity of the DNA-PK enzyme in the presence of an equivalent amount of a reference compound of formula (I) or (II), wherein a lower activity of the DNA-PK polypeptide in the presence of the test compound than in the presence of the reference compound indicates that the test compound is a more potent inhibitor than the reference compound, and a higher activity of the DNA-PK polypeptide in the presence of the test compound than in the presence of the reference compound indicates that the test compound is a less potent inhibitor than the reference compound.

The invention further provides methods of characterizing the potency of a test compound as an inhibitor of a DNA-PK polypeptide, said method comprising the steps of: (a) determining an amount of a control compound of formula (I) or (II) that inhibits an activity of a DNA-PK polypeptide by a reference percentage of inhibition, thereby defining a reference inhibitory amount for the control compound; (b) determining an amount of a test compound that inhibits an activity of a DNA-PK polypeptide by a reference percentage of inhibition, thereby defining a reference inhibitory amount for the test compound; (c) comparing the reference inhibitory amount for the test compound to a reference inhibitory amount determined according to step (a) for the control compound of formula (I) or (II), wherein a lower reference inhibitory amount for the test compound than for the control compound indicates that the test compound is a more potent inhibitor than the control compound, and a higher reference inhibitory amount for the test compound than for the control compound indicates that the test compound is a less potent inhibitor than the control compound. The method utilizes a reference inhibitory amount, which is the amount of the compound that inhibits the activity of the DNA-PK polypeptide by 50%, by 60%, by 70%, or by 80%. In another aspect, the method employs a reference inhibitory amount that is the amount of the compound that inhibits the activity of the DNA-PK polypeptide by 90%, by 95%, or by 99%. Methods of the invention can comprise determining the reference inhibitory amount of the test compound in an in vitro biochemical assay, determining the reference inhibitory amount of the test compound in an in vitro cell-based assay, or determining the reference inhibitory amount of the test compound in an in vivo assay.

The invention also provides an article of manufacture comprising: (a) an anti-cancer compound that induces double-strand DNA breakage in cells, and (b) a package insert describing coordinated administration to a patient of said anti-cancer compound and a DNA-PK inhibitor compound of formula (I) or (II). The article of manufacture comprises an anti-cancer compound, preferably a chemotherapeutic compound, preferably selected from the group consisting of bleomycin, etoposide, and chlorambucil.

The invention further provides an article of manufacture, comprising: (a) a compound selected from the group consisting of cytokines, lymphokines, growth factors, and hematopoietic factors; and (b) a package insert describing coordinated administration to a patient of said compound and a DNA-PK inhibitor compound selected from compounds of formula (I) or (II).

DETAILED DESCRIPTION OF THE INVENTION

Definitions

An "$IC_{50}$ value" of a compound is defined as the concentration of the compound required to produce 50% inhibition of DNA-PK biological or enzymatic activity. Inhibitors of DNA-PK activity are defined to have an $IC_{50}$ of preferably less than about 200 µM, less than about 100 µM, less than about 50 µM, and from about 0.005 µM to 40 µM. Most preferably, a present inhibitor has an $IC_{50}$ of less than 1 µM.

The term "pharmaceutically acceptable carrier" as used herein refers to compounds suitable for use in contact with recipient animals, preferably mammals, and more preferably humans, and having a toxicity, irritation, or allergic response commensurate with a reasonable benefit/risk ratio, and effective for their intended use.

The term "prodrug" as used herein refers to compounds which transformed rapidly in vivo to a compound of the invention, for example, by hydrolysis. Prodrugs of the invention also can be active in the prodrug form. A thorough discussion is provided in Higuchi et al., *Prodrugs as Novel Delivery Systems, Vol.* 14, of the A.C.S.D. Symposium Series, and in Roche (ed), *Bioreversible Carriers in Drug Design*, American Pharmaceutical Association and Pergamon Press, 1987.

The term "alkyl" and "alkylene" as used herein refers to a straight- or branched-chain hydrocarbon group, preferably containing one to eight carbon atoms. Examples of suitable alkyl groups are $C_1$–$C_5$ alkyl groups. As used herein the designation $C_x$–$C_y$ and $C_{x-y}$, wherein x and y are integers, denotes an alkyl group having from x to y carbons, e.g., a $C_1$–$C_5$ or $C_{1-5}$ alkyl group has one to five carbon atoms. Particular examples of alkyl groups include, but are not limited to, methyl, ethyl, n-propyl, isopropyl, n-butyl, sec-butyl (1-methylpropyl), t-butyl (1,1-dimethylethyl), n-pentyl, t-pentyl (1,1-dimethylpropyl), n-hexyl, and the like. Examples of alkylene groups include methylene (—$CH_2$—) and ethylene (—$CH_2CH_2$—).

The term "substituted alkyl" and "substituted alkylene" as used herein refers to an alkyl or alkylene group having one or more substituents. The substituents can include, but are not limited to, cycloalkyl, aryl, heteroaryl, heterocyclic, substituted aryl, substituted heteroaryl, substituted heterocyclic, $N(R^h)_2$, $OR^h$, $SR^h$, sulfoxide, sulfonyl, halo, carboxyl, acyl, carboxy, hydrazino, hydrazono, and hydroxyamino. Like alkyl groups, the preferred substituted alkyl groups have one to five carbons, not including carbon atoms on the substituent group. Preferably, the alkyl group is either mono- or di- substituted at one, two, or three carbons. The substituents can be bound to the same carbon or different carbons.

The term "alkoxy" as used herein refers to a straight- or branched-chain alkyl or substituted alkyl group attached to the parent molecule through an oxygen atom, typically by a carbon to oxygen bond. The hydrocarbon of the alkoxy group preferably contains one to five carbon atoms. Typical alkoxy groups are methoxy, ethoxy, n-propoxy, isopropoxy, n-butoxy, sec-butoxy (1-methylpropoxy), t-butoxy (1,1-dimethylethoxy), n-pentoxy, t-pentoxy (1,1-dimethylpropoxy), and the like. The term "thioalkoxy" is similarly defined, except sulfur replaces oxygen.

The term "acyl" as used herein refers to an $R^aC(=O)$-group attached to the parent molecule through a carbonyl (—C=O) group. $R^a$ is defined as an alkyl, substituted alkyl, cycloalkyl, aryl, substituted aryl, heteroaryl, substituted heteroaryl, heterocylic, and substituted heterocyclic group. The preferred acyl group contains one to ten carbon atoms.

The term "cycloalkyl" as used herein refers to nonaromatic cyclic hydrocarbon group, preferably containing three to six carbon atoms. Examples of cycloalkyl are cyclopropyl, cyclobutyl, cyclopentyl, cyclohexyl, and the like. Cycloalkyl groups also can have alkyl and alkoxy substituents, as defined above, as well as halo substituents.

The term "aldehyde" as used herein refers to a —CHO group.

The term "amino" as used herein refers an —$NH_2$ or —NH— group, wherein each hydrogen in each formula can be replaced with an alkyl, aryl, heteroaryl, heterocyclic, substituted alkyl, substituted aryl, or substituted heterocyclic group, i.e., $N(R^h)_2$. In the case of —$NH_2$, the hydrogen atoms also can be replaced with a substituents taken together to form a 5- to 6-membered aromatic or nonaromatic ring, wherein one or two carbons of the ring optionally are replaced with a heteroatom selected from the group consisting of sulfur, oxygen, and nitrogen. The ring also optionally can be substituted with an alkyl group. Examples of rings formed by substituents taken together with the nitrogen atom include, but are not limited to, morpholinyl, phenylpiperazinyl, imidazolyl, pyrrolidinyl, (N-methyl)-piperazinyl, piperidinyl, and the like.

The term "aryl" as used herein refers to a monocyclic, fused bicyclic, and fused tricyclic carbocyclic ring systems having one or more aromatic rings including, but not limited to, phenyl, naphthyl, tetrahydronaphthyl, phenanthrenyl, biphenylenyl, indanyl, indenyl, anthracenyl, phenanthrenyl, fluorenyl, and the like.

The term "carbamoyl" as used herein refers to a group of the formula —$NR^bC(=O)R^b$, —$OC(=O)N(R^b)$ and —$NR^bC(=O)$—, wherein $R^b$ is hydrogen, alkyl, substituted alkyl (including trifluoromethyl), aryl, substituted aryl, heteroaryl, or substituted heteroaryl.

The term "carbonyl" as used herein refers to a —(CO)— (or —C=O) group.

The term "carboxyl" as used herein refers to —$CO_2H$.

The term "carboxamide" as used herein refers to —$C(=O)N(R^c)_2$, wherein $R^c$ is defined as hydrogen, alkyl, substituted alkyl, aryl, substituted aryl, heteroaryl, substituted heteroaryl, heterocyclic, substituted heterocyclic, cycloalkyl, and $OR^h$, or the $R^c$ groups are taken together with the nitrogen to which they are attached to form a five- or six-membered optionally substituted aromatic or nonaromatic ring, wherein one or two carbons of the ring optionally are replaced with a heteroatom selected from the group consisting of sulfur, oxygen, and nitrogen.

The term "thiocarboxamide" as used herein refers to —$C(=S)N(R^c)_2$, wherein $R^c$ is defined above.

The term "mercapto" as used herein refers to —$SR^c$, wherein $R^c$ is defined above.

The term "sulfonamido" as used herein refers to —$NHSO_2R^c$, wherein $R^c$ is defined above.

The term "sulfo" as used herein refers to —$SO_3H$, and halide derivatives thereof, like —$SO_2Cl$, i.e., sulfonyl chloride.

The term "carboxy" as used herein refers to —COOH and —$COOR^a$, wherein $R^a$ is defined above.

The term "cyano" as used herein refers to a —C≡N group, also designated —CN.

The term "hydroxyamino" as used herein refers to a —NHOH group.

The term "hydrazono" as used herein refers to a =N—$NH_2$ group, wherein one or both hydrogen atoms can be replaced with an alkyl or substituted alkyl group.

The terms "trifluoromethyl" and "trifluoromethoxy" as used herein refer to —$CF_3$ and —$OCF_3$, respectively.

The term "halo" as used herein refers to bromo, chloro, iodo, and fluoro.

The term "phosphate" as used herein refers to a —OP(=O)(OR$^c$)$_2$, and salts thereof.

The term "sulfonyl" as used herein refers to group represented by —$SO_2$— or —$SO_2$—$R^a$ wherein $R^a$ is defined above.

The term "sulfamyl" as used herein refers to —$SO_2N(R^c)_2$, wherein $R^c$ is defined above.

The term "nitro" as used herein refers to —$NO_2$.

The term "heteroaryl" as used herein refers to a cyclic aromatic ring system having five to ten ring atoms, wherein one to four-ring atoms is selected from the group consisting of oxygen, nitrogen, and sulfur and the remaining ring atoms are carbon, said ring system being joined to the remainder of the molecule by any of the ring atoms. Nonlimiting examples of heteroaryl include pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, thiophenyl, furanyl, quinolinyl, isoquinolinyl, benzoxazolyl, benzimidazolyl, benzothiazolyl, and the like.

The term "heterocycloalkyl," and "heterocyclic" as used herein refers to a nonaromatic partially unsaturated or fully saturated 3- to 10-membered ring system, which includes single rings of 3 to 8 atoms, and bi- or tri-cyclic ring systems. These heterocyclic ring systems include those having from one to four heteroatoms independently selected from oxygen, nitrogen, and sulfur, wherein the nitrogen and sulfur heteroatoms optionally can be oxidized and the nitrogen heteroatom optionally can be substituted. Representative heterocyclics include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, and the like.

The term "substituted aryl," "substituted heteroaryl," and "substituted heterocyclic" as used herein refer to an aryl, heteroaryl, or heterocyclic group substituted by a replacement of one, two, or three of the hydrogen atoms thereon with a substitute selected from the group consisting of halo, $OR^h$, $N(R^h)_2$, CN, alkyl, substituted alkyl, mercapto, nitro, aldehyde, carboxy, carboxyl, carboxamide, aryl, heteroaryl, cycloalkyl, heterocyclic, $O(CH_2)_{1-3}N(R^h)_2$, $O(CH_2)_{1-3}CO_2H$, and trifluoromethyl.

DNA-PK Inhibitors

The invention provides compounds that inhibit DNA-PK biological activity. Inhibitor compounds of the present invention have a formula (I) or (II). Preferred compounds are those of formula (I) and (II) wherein A is a morpholinyl, thiomorpholinyl, piperidinyl, piperazinyl, or tetrahydropyranyl group and L is absent. Other preferred DNA-PK inhibitor compounds are those compounds of formula (I) and (II), wherein:

n is an integer from 0 through 4;

Z, independently, is $CR^3$ or N, or $CR^7$ or N;

L is absent, or L is selected from the group consisting of —$(CH_2)_p$—, —$(CHR^k)_p$—, —$NR^k$—$(CHR^k)_p$—, —$(CHR^k)$—$NR^k$—, —$NR^k$—, —$C(=O)$—, —O—, —$NR^k$—(CO)—, —(CO)—$NR^k$—, —S—, —SO—, —$SO_2$—, and —$NR^sR^t$ (only if A is absent), wherein p is an integer 1 to 5;

$R^k$ is selected from the group consisting of alkyl, aryl, and hydrogen;

$R^s$ is selected from the group consisting of hydrogen, and alkyl;

$R^t$ is alkyl, optionally substituted with oxo, hydroxy, methoxy, benzyloxy, halo, aryl, or heteroaryl;

A is absent, or is selected from the group consisting of a four- to seven-membered heterocyclic ring containing 1 or 2 heteroatoms independently selected from the group consisting of N, O, and S;

$R^1$ or $R^5$ is selected from the group consisting of —H, —$NH_2$, —(CO)—$NH_2$, —(CO)—NH—OH, —(CO)—NH—$NH_2$, —(CO)—NH—NH—$R^f$, —(CO)—OH, —(CO)—O—$CH_3$, —(CO)—O—$CH_2$—$CH_3$, —(CO)-(4-methoxy)phenyl, —(CO)-(4-hydroxy)phenyl, —(CO)-(3-chlorophenyl), —(CO)-phenyl, —(CO)-benzyl, —(CO)—$C_{1-4}$alkyleneOR$^h$, —(CO)—$C_{1-4}$alkyleneSR$^h$,

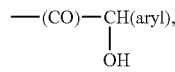

—$NO_2$, —OH, —(CO)—$C_{1-4}$ alkyl, -cycloalkyl, —(CO)-substituted alkyl, —(CO)—(methoxy)alkyl, —(CO)—(alkoxy) substituted alkyl, —(CO)-aryl, —(CO)-heteroaryl, —(CO)-(substituted alkyl)$_p$-aryl, —(CO)-(substituted alkoxy)$_p$-aryl, —(CO)—(($NR^k$)$_p$-substituted alkoxy)-aryl, —(CO)-aryl-$R^d$, —(CO)-aryl-$R^e$, —(CO)-aryl-$R^f$, —CH=N—OH, —CH=N—$NH_2$, —CH=N—NH—$CH_3$, —CH=N—NH—$CH_2$-phenyl, —$CF_3$, —(CO)—$CF_3$, —(CO)—$CH_2$-morpholinyl, —(CO)—$CH_2$-heteroaryl, —(CO)—$CH_2$—CH—($CH_3$)$_2$, —(CO)—$CH_2$—$CH_2$—($SO_2$)—$CH_3$, —CHO, —C≡N, —$CH_2$—OH, —(CO)N$R^d$$R^e$, —(CS)—$NH_2$, —(CO)—$R^f$, —(CO)—$CH_2$Cl, —(CO)—$CH_2$—$NR^dR^e$, —(CO)—$CH_2$—S—(CO)—$CH_3$, —(CO)—$CH_2$—SH, —($SO_2$)-phenyl, 2-(anilino)-4-thiazolyl-, 2-(pyridyl)-4-thiazolyl-, -benzoxazolyl, -imidazolyl, -thiazolyl, -substituted thiazolyl, -benzimidazolyl, -benzothiazolyl, -tetrazolyl, -(N-benzyl)-tetrazolyl, -(N-methyl)-tetrazolyl, -pyrazolyl, -(N-benzyl)-pyrazolyl, -(N-methyl)-pyrazolyl, -(N-acetyl)-pyrazolyl, -(N-mesyl)-pyrazolyl, -pyrazolyl-(CO)—$R^uR^v$, -(N-phenyl)-piperazinyl, -isoxazolyl, -pyrimidinyl, -(2-NH—$CH_2$-phenyl)-pyrimidinyl, -(2-(SO)-methyl)-pyrimidinyl, -(2-N-(N-t-butoxycarbonyl)-piperazinyl)-pyrimidinyl, and -(2-NH—$CH_2$-pyridine)-pyrimidinyl;

wherein $R^d$ is selected from the group consisting of —H, -alkyl, —$CH_2$-phenyl, -phenyl, —O—$CH_3$, -pyridyl, -thiazolyl, -thiazinyl, —O—$CH_2$-phenyl, —O-phenyl, —O-methoxyphenyl, —OH, —$CH_2$—(CO)—O—$CH_3$, and —$CH_2$—(CO)—OH; and $R^e$ is selected from the group consisting of —H, —$CH_2$—$CH_2$—O—$CH_3$, —$CH_2$—$CH_2$—$CH_2$—N($CH_3$)$_2$, —O—$CH_3$, —$CH_2$—$CH_2$—($SO_2$)—$CH_3$, —O—$CH_3$, —$CH_2$-pyridyl, —$CH_2$-phenyl, -alkyl, —$CH_2$—(CO)—O—$CH_3$, and -cylcopropyl; or $R^d$ and $R^e$ are taken together to form -morpholinyl, -phenylpiperazinyl, -imidazolyl, -pyrrolidinyl, -(N-methyl)-piperazinyl, and -piperidinyl;

$R^f$ is selected from the group consisting of -phenyl, -phenyl-($CF_3$), -methylphenyl, -methoxyphenyl, -pyridyl, -alkyl, -benzyl, -thiophenyl, -thiazolyl, -chlorophenyl, —C(=NH)—$NH_2$, -fluorophenyl, —(CO)-phenyl, —($CH_2$)-phenyl;

$R^u$ is selected from the group consisting of —H, and -alkyl;

$R^v$ is selected from the group consisting of —O—(CO)—$CH_3$, —NH-t-butoxycarbonyl, —O-phenyl, and —O—$CH_2$-phenyl; or $R^u$ and $R^v$ are taken together with the carbon atoms to which they are attached to form a 5-membered ring containing an N, said N optionally protected with t-butoxycarbonyl, $R^2$ or $R^6$ is selected from the group consisting of —H, —OH, -Halo, —$CH_2$—OH, —(CO)—$NH_2$, —$NH_2$, —(CO)—O—$CH_3$, —O—$CH_3$, —NH—(CO)—$CF_3$, —NH—(CO)—$CH_3$, —NH—($SO_2$)—$CH_3$, —NH—$CH_3$, —N($CH_3$)—(CO)—$CF_3$, —N=((CH(phenyl)—$CH_2$—(CO)OH, —$NO_2$, —O—$PO_3^=$, —O-alkyl, —O—($CH_2$)$_p$—OH, —O—($CH_2$)$_p$—O-benzyl, —O—(CO)-heteroaryl, —O—(CO)-amino acid, —O—(CO)-nicotinic acid, —O—(CO)-aryl, —O—(CO)-alkyl, —O—$CH_2$—(CO)-benzyl, —O—($SO_2$)—O—$CF_3$, —($CH_2$)—CH=CH=N($CH_3$)$_2$, —O—($SO_3$)—, and —O—(PO)(OR$^j$)(OR$^k$);

wherein $R^j$ independently are H, aryl, alkyl, or heterocyclic; or $R^1$ and $R^2$, or $R^5$ and $R^6$, are taken together to form a three- or four-membered component, respectively, of a five- or six-membered ring, preferably said ring selected from the group consisting of -2-imidazolidonyl-, —$R^g$-thiazolyl-, -carbonylpyrrolyl methyl ketone-, -4-imino-1,3,2,-oxathiaphosphanyl-2-thione-, -4-imino-1,3,2,-oxathiaphosphanyl-2-thione-2-(4'-methoxy)-phenyl-, -3-oxofuranyl-, -N-acetyl-3-oxopyrrolinyl-, —N—($CH_2$—COOH)-quinolonyl-, -N-(t-butoxycarbonyl)-quinolonyl-, —N—($CH_2$—COOH)-quinolinyl-, -N-(t-butoxycarbonyl)-quinolinyl-, and

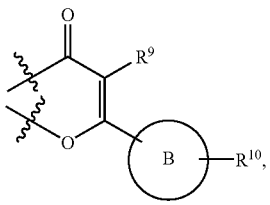

wherein B is aryl or a nitrogen-containing heteroaryl, $R^9$ is H or $OR^h$, and $R^{10}$ is selected from the group consisting of halo, $OR^h$, $O(CH_2)_{1-3}N(R^h)_2$, $O(CH_2)_{1-3}CO_2H$, CN, morpholinyl, and N-(4-methyl)-piperazinyl, wherein $R^g$ is selected from the group consisting of -pyridyl and -anilino;

$R^3$ or $R^7$, independently, is selected from the group consisting of —H, —OH, —$OR^d$, —$NO_2$, —$NH_2$, —NH—$R^d$, -halo, —CHO, —($SO_2$)—OH, —($SO_2$)—Cl, and —($SO_2$)—$NR^iR^k$;

wherein $R^i$ is selected from the group consisting of —H, —$CH_3$, —$CH_2$-phenyl, -phenyl, —$CH_2$—$CH_2$—O—$CH_3$, —$CH_2$—$CH_2$—$CH_2$—$N(CH_3)_2$, —O—$CH_3$, —$CH_2$—$CH_2$—($SO_2$)—$CH_3$, -pyridyl, -thiazolyl, —O—$CH_2$-phenyl, —OH, —$CH_2$—(CO)—O—$CH_3$, and —$CH_2$—(CO)—OH;

$R^k$ is selected from the group consisting of —H, —O—$CH_3$, —$CH_2$-pyridyl, —$CH_2$-phenyl, —$CH_3$, —$CH_2$—(CO)—O—$CH_3$, -cyclopropyl, and —$CH_2$-cyclopropyl; or $R^i$ and $R^k$ are taken together to form morpholinyl, phenylpiperazinyl, imidazolyl, pyrrolidinyl, (N-methyl)-piperazinyl, and piperidinyl; and $R^4$ or $R^8$, independently, is selected from the group consisting of —H, —$CH_3$, —$OCH_3$, —OH, —(CO)—$CH_3$, -methoxyphenyl, and -pyridinyl.

The preferred groups for the substituents $R^1$ and $R^5$ in a compound of formula (I) or (II) are —H, —OH, —$NH_2$, —$CH_2OH$, —C≡N, —(CO)—$NH_2$, —(CO)—OH, —(CO)—O—$CH_3$, —CH═N—OH, —CH═N—$NH_2$, —CH═N—NH—$CH_3$, —(CO)—$CF_3$, —(CO)H, —$NO_2$, —(CO)-alkyl, —(CO)-substituted alkyl, —(CO)-aryl, —(CO)-substituted aryl, —(CO)-heteroaryl, —(CO)—$CH_2$—$NR^dR^e$, and —(CO)$NR^dR^e$, wherein $R^d$ and $R^e$ are as previously defined.

The preferred groups for the substituent $R^2$ and $R^6$ in a compound of formula (I) or (II) are —H, —OH, —F, —$CH_2$—OH, —$NH_2$, —NH—(CO)—$CF_3$, —NH—(CO)—$CH_3$, —NH—($SO_2$)—$CH_3$, —NH—$CH_3$, and —N($CH_3$)—(CO)—$CF_3$.

Examples of compounds of the invention include, but are not limited to, compounds described in Table 1, below.

TABLE 1

DNA-PK INHIBITORS

Benzyl 2-((4-benzyl)carbonyl)-5-morpholin-4-yl-benzene phosphate
4-Methylphenyl 4-morpholin-4-yl-2-(phosphonooxy)phenyl methanone disodium salt
5-Morpholin-4-yl-2-nitrophenylamine
5-(4-Methyl-piperazin-1-yl)-2-nitrophenylamine
2-Hydroxymethyl-5-morpholin-4-yl-phenol
2-Nitro-5-thiomorpholin-4-yl-phenylamine
$N^1$-Morpholin-4-yl-4-nitrobenzene-1,3-diamine
1-(3-Amino-4-nitrophenyl)-piperidin-4-ol
2-Nitro-5-piperidin-1-yl-phenylamine TABLE 1-continued

DNA-PK INHIBITORS 5-(4-acetylpiperazin-1-yl)-2-nitrophenylamine
2-Nitro-5-piperazin-1-yl-phenylamine
1-(3-Amino-4-nitrophenyl)-piperidin-3-ol
$N^1$-(2-Morpholin-4-yl-ethyl)-4-nitrobenzene-1,3-diamine
5-[4-(2-Methoxyphenyl)-piperazin-1-yl]-2-nitrophenylamine
5-(cis-2,6-Dimethylmorpholin-4-yl)-2-nitrophenylamine
2-Nitro-5-(4-pyridin-2-yl-piperazin-1-yl)-phenylamine
$N^1$-(3-Morpholin-4-yl-propyl)-4-nitrobenzene-1,3-diamine
2-Hydroxy-4-morpholin-4-yl-benzonitrile
(5-Morpholin-4-yl-2-nitrophenyl)-methanol
2-Hydroxy-4-morpholin-4-yl-benzoic acid
2-Hydroxy-4-morpholin-4-yl-benzoic acid methyl ester
5-Morpholin-4-yl-2-nitro-benzamide
2-Hydroxy-4-morpholin-4-yl-benzaldehyde
5-Morpholin-4-yl-2-nitro-phenol
1-(2-Hydroxy-4-morpholin-4-yl-phenyl)-ethanone
1-(2-Hydroxy-4-morpholin-4-yl-phenyl)-propan-1-one
1-(2-Hydroxy-4-morpholin-4-yl-phenyl)-3-methyl-butan-1-one
1-(2-Hydroxy-4-morpholin-4-yl-phenyl)-1-phenyl-methanone
2,2,2-Trifluoro-1-(2-hydroxy-4-morpholin-4-yl-phenyl)-ethanone
4-Amino-2-morpholin-4-yl-pyrimidine-5-carboxylic acid
1-(5-Bromo-2-hydroxy-4-morpholin-4-yl-phenyl)-ethanone
1-(3-Bromo-2-hydroxy-4-morpholin-4-yl-phenyl)-ethanone
1-(3,5-Dichloro-2-hydroxy-4-morpholin-4-yl-phenyl)-ethanone
1-(3-Chloro-2-hydroxy-4-morpholin-4-yl-phenyl)-ethanone
1-(5-Fluoro-2-hydroxy-4-morpholin-4-yl-phenyl)-ethanone
1-(3-Fluoro-2-hydroxy-4-morpholin-4-yl-phenyl)-ethanone
1-[2-Hydroxy-4-(tetrahydropyran-4-yloxy)-phenyl]-ethanone
5-(Morpholin-4-yl)-1,3-dihydro-benzimidazol-2-one
2-Methoxy-4-morpholin-4-yl-benzaldehyde
4-Methoxy-6-morpholin-4-yl-benzene-1,3-dicarbaldehyde
2-Hydroxy-5-morpholin-4-yl-benzoic acid methyl ester
2-((Hydroxyimino)methyl)-5-morpholin-4-yl-phenol
2-Hydrazonomethyl-5-morpholin-4-yl-phenol
2-Hydroxy-4-[(1-morpholin-4-yl-methanoyl)amino]-benzoic acid
2-Hydroxy-4-morpholin-4-ylmethyl-benzoic acid methyl ester hydrochloride
2-Hydroxy-4-morpholin-4-ylmethyl-benzoic acid trifluoroacetate
2-Hydroxy-4-morpholin-4-ylmethyl-benzoic acid hydrochloride
4-Amino-2-hydroxy-benzoic acid methyl ester
2-Hydroxy-4-morpholin-4-yl-benzoic acid methyl ester
2-Hydroxy-N-methyl-4-morpholin-4-yl-benzamide
1-(2-Hydroxy-4-morpholin-4-yl-phenyl)-1-morpholin-4-yl-methanone
2-Hydroxy-4-morpholin-4-yl-benzamide
2-Hydroxy-4-morpholin-4-yl-N-benzyl-benzamide
2-Hydroxy-4-morpholin-4-yl-N-phenyl-benzamide
N-Cyclopropyl-2-hydroxy-4-morpholin-4-yl-N-phenyl-benzamide
2-Hydroxy-N-(2-methoxyethyl)-4-morpholin-4-yl-benzamide
2-Hydroxy-4-morpholin-4-yl-N-methoxy-N-methyl-benzamide
2-Hydroxy-4-morpholin-4-yl-N-(3-dimethylaminopropyl)-benzamide
2-Hydroxy-N-methoxy-4-morpholin-4-yl-benzamide
2-Hydroxy-N-(2-methanesulfonylethyl)-4-morpholin-4-yl-benzamide
2-Hydroxy-4-morpholin-4-yl-N-pyridin-3-yl-benzamide
2-Hydroxy-4-morpholin-4-yl-N-pyridin-4-yl-benzamide
2-Hydroxy-4-morpholin-4-yl-N-thiazol-2-yl-benzamide
2-Hydroxy-4-morpholin-4-yl-N-(1,4-thiazin-2-yl)-benzamide
2,N-Dihydroxy-4-morpholin-4-yl-benzamide
2-Hydroxy-4-morpholin-4-yl-N-(4-pyridylmethyl)-benzamide
1-(2-Hydroxy-4-morpholin-4-yl-phenyl)-1-(4-phenylpiperizin-1-yl)-methanone
2-Hydroxy-4-morpholin-4-yl-benzoic acid
N-Carboxymethyl-2-hydroxy-4-morpholin-4-yl-phenyl)-carboxamide methyl ester
N-Carboxymethyl-2-hydroxy-4-morpholin-4-yl-phenyl-carboxamide
2-Hydroxy-4-morpholin-4-yl-thiobenzamide
2-(4-Ethylphenyl)-4-imino-7-morpholin-4-yl-benzo[e]-1,3,2-oxathiaphosphane-2-thione
1-(2-Hydroxy-4-morpholin-4-yl-phenyl)-1-phenyl-methanone
1-(2-Hydroxy-4-morpholin-4-yl-phenyl)-1-(4-trifluoromethylphenyl)-methanone
1-(2-Hydroxy-4-morpholin-4-yl-phenyl)-1-(o-tolyl)-methanone
1-(2-Hydroxy-4-morpholin-4-yl-phenyl)-1-(4-methoxyphenyl)-methanone
1-(2-Hydroxy-4-morpholin-4-yl-phenyl)-1-pyridin-3-yl-methanone
1-(2-Hydroxy-4-morpholin-4-yl-phenyl)-pentan-1-one
1-(2-Hydroxy-4-morpholin-4-yl-phenyl)-2-phenyl-ethanone
1-(2-Hydroxy-4-morpholin-4-yl-phenyl)-1-thiophen-2-yl-methanone
2-Hydroxy-4-morpholin-4-yl-phenyl-1,3-thiazol-2-yl ketone

TABLE 1-continued

DNA-PK INHIBITORS 1-(3-Chlorophenyl)-1-(2-hydroxy-4-morpholin-4-yl-phenyl)-methanone
2-Chloro-1-(2-hydroxy-4-morpholin-4-yl-phenyl)-ethanone
1-(2-Hydroxy-4-morpholin-4-yl-phenyl)-2-morpholin-4-yl-ethanone
1-(2-Hydroxy-4-morpholin-4-yl-phenyl)-2-imidazol-1-yl-ethanone
1-(2-Hydroxy-4-morpholin-4-yl-phenyl)-1-pyrrolidin-1-yl-methanone
1-(2-Hydroxy-4-morpholin-4-yl-phenyl)-1-(4-methyl-piperazin-1-yl)-methanone
2-Hydroxy-4-morpholin-4-yl-phenyl-1-piperidin-1-yl-methanone
2-(Benzyl-methyl-amino)-1-(2-hydroxy-4-morpholin-4-yl-phenyl)-ethanone
2-Acetylthio-1-(2-hydroxy-4-morpholin-4-yl-phenyl)-ethanone
1-(2-Hydroxy-4-morpholin-4-yl-phenyl)-2-mercapto-ethanone
6-Morpholin-4-yl-2-hydrobenzo(b)furan-3-one
4-[2-Methyl-4-morpholin-4-yl-phenyl)-2-(3-pyridyl)-1,3-thiazole
5-Morpholin-4-yl-2-(2-phenylamino-1,3-thiazol-4-yl)-phenol
3-Methoxy-1-morpholin-4-yl-benzene
4-Methoxy-2-morpholin-4-yl-benzenesulfonic acid
4-Methoxy-2-morpholin-4-yl-benzenesulfonyl chloride
4-Methoxy-N-methyl-2-morpholin-4-yl-benzenesulfonamide
4-Methoxy-2-morpholin-4-yl-N-benzyl-benzenesulfonamide
4-Methoxy-2-morpholin-4-yl-N-cyclopropylmethyl-benzenesulfonamide
N,N-Diethyl-(3-morpholin-4-yl-phenoxy)carboxamide
N,N-Diethyl-(2-benzenesulfonyl-5-morpholin-4-yl-phenoxy)carboxamide
2-Benzenesulfonyl-5-morpholin-4-yl-phenol
3-Nitro-1-morpholin-4-yl-benzene
3-Morpholin-4-yl-phenylamine
1-(2-Amino-4-morpholin-4-yl-phenyl)-2-chloro-ethanone
2-Amino-4-morpholin-4-yl-N-benzyl-N-methyl-benzamide
1-(2-Amino-4-morpholin-4-yl-phenyl)-1-pyrrolidin-1-yl-methanone
(2-Amino-4-morpholin-4-yl-phenyl)-1-piperidin-1-yl-methanone
2-Amino-4-fluorobenzoic acid methyl ester
4-Fluoro-2-(2,2,2-trifluoroacetylamino)-benzoic acid methyl ester
4-Morpholin-4-yl-2-(2,2,2-trifluoroacetylamino)-benzoic acid methyl ester
2-Amino-4-morpholin-4-yl-benzoic acid
2-Methylsulfonylamino-4-morpholin-4-yl-benzoic acid
4-Morpholin-4-yl-2-(2,2,2-trifluoroacetylamino)-N-benzyl-benzamide
N,N-Dimethyl-4-morpholin-4-yl-2-(2,2,2-trifluoroacetylamino)-benzamide
2-Amino-4-morpholin-4-yl-N,N-dimethyl-benzamide
N-Methyl-4-morpholin-4-yl-2-(2,2,2-trifluoroacetylamino)-benzamide
2-Amino-4-morpholin-4-yl-benzoic acid methyl ester
2-Acetylamino-4-morpholin-4-yl-benzoic acid methyl ester
2-Acetylamino-4-morpholin-4-yl-benzoic acid
2-Methanesulfonylamino-4-morpholin-4-yl-benzoic acid methyl ester
(2-N-Methyl-N-(2,2,2-trifluoroacetyl)amino)-4-morpholin-4-yl-benzoic acid methyl ester
2-Methylamino-4-morpholin-4-yl-benzoic acid methyl ester
2-Methylamino-4-morpholin-4-yl-benzoic acid
2-Chloro-1-(2-acetamido-4-morpholin-4-yl-phenyl)-ethanone
1-Acetyl-6-morpholin-4-yl-1,2-dihydro-indol-3-one
4-Morpholin-4-yl-2-nitro-benzoic acid methyl ester
4-Morpholin-4-yl-2-nitro-benzoic acid
4-Morpholin-4-yl-2-nitrophenyl)-N-(methylcarboxymethyl)benzamide
5-Hydroxy-7-morpholin-4-yl-2-phenyl-chromen-4-one
5-Hydroxy-2-phenyl-7-piperidin-1-yl-chromen-4-one
Trifluoromethanesulfonic acid 3,5-dihydroxy-4-oxo-2-phenyl-4H-chromen-7-yl ester
3,5-Dihydroxy-7-morpholin-4-yl-2-phenyl-chromen-4-one
Trifluoromethanesulfonic acid 4-acetyl-3,5-dihydroxy-phenyl ester
1-(2,6-Dihydroxy-4-morpholin-4-yl-phenyl)-ethanone
4-(5-Hydroxy-7-morpholin-4-yl-4-oxo-4H-chromen-2-yl)-benzonitrile
3-(5-Hydroxy-7-morpholin-4-yl-4-oxo-4H-chromen-2-yl)-benzonitrile
5-Hydroxy-2-(4-methoxyphenyl)-7-morpholin-4-yl-Chromen-4-one
5-Hydroxy-7-morpholin-4-yl-2-pyridin-3-yl-chromen-4-one
2-Hydroxy-1-(2-hydroxy-4-morpholin-4-yl-phenyl)-ethanone
2-Hydroxy-1-(2-hydroxy-4-morpholin-4-yl-phenyl)-ethanone.

DNA-PK inhibitor compounds of the invention can exist as stereoisomers having asymmetric or chiral centers. Stereoisomers are designated by either "S" or "R" depending on arrangement of substituents around a chiral carbon atom. Mixtures of stereoisomers are contemplated under the invention. Stereoisomers include enantiomers, diastereomers, and mixtures of the two. Individual stereoisomers of compounds of the invention can be prepared synthetically from commercially available starting materials which contain asymmetric or chiral centers or by preparation of racemic mixtures followed by separation or resolution techniques well known in the art. Methods of resolution include (1) attachment of a mixture of enantiomers to a chiral auxiliary, separation of the resulting mixture by recrystallization or chromatography, and liberation of the optically pure product from the auxiliary, (2) salt formation employing an optically active resolving agent, and (3) direct separation of the mixture of optical enantiomers on chiral chromatographic columns.

The invention also provides prodrug forms of DNA-PK inhibitors of the invention. Prodrug design is discussed generally in Hardma et al., (Eds), *Goodman & Gilman's The Pharmacological Basis of Therapeutics*, Ninth Edition, New York, N.Y. (1996), pp. 11–16. Briefly, administration of a drug is followed by elimination from the body or some biotransformation whereby biological activity of the drug is reduced or eliminated. Alternatively, a biotransformation process can lead to a metabolic by-product which is itself more active or equally active as compared to the drug initially administered. Increased understanding of these biotransformation processes permits the design of so-called "prodrugs" which, following a biotransformation, become more physiologically active in an altered state. Prodrugs are pharmacologically inactive or active compounds which are converted to biologically active or more active metabolites. In some forms, prodrugs are rendered pharmacologically active through hydrolysis of, for example, an ester or amide linkage, often times introducing or exposing a functional group on the prodrug. The thus modified drug also can react with an endogenous compound to form a water soluble conjugate which further increases pharmacological properties of the compound, for example, as a result of increased circulatory half-life.

As another alternative, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into circulation, thereby effectively increasing the biological half-life of the originally administered compound. Prodrugs are particularly useful for delivering a compound to a predetermined site of action, and modifications can be effected to facilitate targeting in this manner.

Pharmaceutical Compositions

The invention also provides pharmaceutical compositions comprising one or more DNA-PK inhibitors of formula (I) or (II). The pharmaceutical composition comprises the DNA-PK inhibitors of formula (I) or (II) in a pharmaceutically acceptable carrier or diluent, including, but not limited to, preferred compounds of formula (I) or (II). The invention also provides pharmaceutical compositions having a compound of formula (I) or (II) in combination with an antineoplastic agent.

In a preferred embodiment, the pharmaceutical compositions comprise one or more DNA-PK inhibitor compounds including, but not limited to, the compounds set forth below:

TABLE 2

4-(4-(1-Phenylvinyl)phenyl]morpholine
4-(4-Nitrophenyl)morpholine
Methyl 7-amino-2-morpholin-4-yl-7a-hydro-1,2,4-triazolo-(1,5-a]pyrimidine-6-carboxylate
1-(4-Morpholin-4-ylphenyl)ethan-1-one
Benzyl 2-[(4-benzyl)carbonyl]-5-morpholin-4-yl-benzene phosphate
4-Methylphenyl 4-morpholin-4-yl-2-(phosphonooxy)phenyl methanone disodium salt
5-Morpholin-4-yl-2-nitrophenylamine
5-(4-Methylpiperazin-1-yl)-2-nitrophenylamine
2-Hydroxymethyl-5-morpholin-4-yl-phenol
2-Nitro-5-thiomorpholin-4-yl-phenylamine
$N^1$-Morpholin-4-yl-4-nitrobenzene-1,3-diamine
1-(3-Amino-4-nitrophenyl)-piperidin-4-ol
2-Nitro-5-piperidin-1-yl-phenylamine
5-(4-acetylpiperazin-1-yl)-2-nitrophenylamine
2-Nitro-5-piperazin-1-yl-phenylamine
1-(3-Amino-4-nitrophenyl)-piperidin-3-ol
$N^1$-(2-Morpholin-4-yl-ethyl)-4-nitrobenzene-1,3-diamine
5-[4-(2-Methoxyphenyl)piperazin-1-yl]-2-nitrophenylamine
5-(cis-2,6-Dimethylmorpholin-4-yl)-2-nitrophenylamine
2-Nitro-5-(4-pyridin-2-yl-piperazin-1-yl)-phenylamine
$N^1$-(3-Morpholin-4-yl-propyl)-4-nitrobenzene-1,3-diamine
2-Hydroxy-4-morpholin-4-yl-benzonitrile
(5-Morpholin-4-yl-2-nitrophenyl)-methanol
2-Hydroxy-4-morpholin-4-yl-benzoic acid
2-Hydroxy-4-morpholin-4-yl-benzoic acid methyl ester
5-Morpholin-4-yl-2-nitro-benzamide
2-Hydroxy-4-morpholin-4-yl-benzaldehyde
5-Morpholin-4-yl-2-nitro-phenol
1-(2-Hydroxy-4-morpholin-4-yl-phenyl)-ethanone
1-(2-Hydroxy-4-morpholin-4-yl-phenyl)-propan-1-one
1-(2-Hydroxy-4-morpholin-4-yl-phenyl)-3-methyl-butan-1-one
1-(2-Hydroxy-4-morpholin-4-yl-phenyl)-1-phenyl-methanone
2,2,2-Trifluoro-1-(2-hydroxy-4-morpholin-4-yl-phenyl)-ethanone
4-Amino-2-morpholin-4-yl-pyrimidine-5-carboxylic acid
1-(5-Bromo-2-hydroxy-4-morpholin-4-yl-phenyl)-ethanone
1-(3-Bromo-2-hydroxy-4-morpholin-4-yl-phenyl)-ethanone
1-(3,5-Dichloro-2-hydroxy-4-morpholin-4-yl-phenyl)-ethanone
1-(3-Chloro-2-hydroxy-4-morpholin-4-yl-phenyl)-ethanone
1-(5-Fluoro-2-hydroxy-4-morpholin-4-yl-phenyl)-ethanone
1-(3-Fluoro-2-hydroxy-4-morpholin-4-yl-phenyl)-ethanone
1-[2-Hydroxy-4-(tetrahydropyran-4-yloxy)-phenyl]-ethanone
5-(Morpholin-4-yl)-1,3-dihydro-benzimidazol-2-one
2-Methoxy-4-morpholin-4-yl-benzaldehyde
4-Methoxy-6-morpholin-4-yl-benzene-1,3-dicarbaldehyde
2-Hydroxy-5-morpholin-4-yl-benzoic acid methyl ester
2-((Hydroxyimino)methyl)-5-morpholin-4-yl-phenol
2-Hydrazonomethyl-5-morpholin-4-yl-phenol
2-Hydroxy-4-[(1-morpholin-4-yl-methanoyl)-amino]-benzoic acid
2-Hydroxy-4-morpholin-4-ylmethyl-benzoic acid methyl ester hydrochloride
2-Hydroxy-4-morpholin-4-ylmethyl-benzoic acid trifluoroacetate
2-Hydroxy-4-morpholin-4-ylmethyl benzoic acid hydrochloride
4-Amino-2-hydroxy-benzoic acid methyl ester
2-Hydroxy-4-morpholin-4-yl-benzoic acid methyl ester
2-Hydroxy-N-methyl-4-morpholin-4-yl-benzamide
1-(2-Hydroxy-4-morpholin-4-yl-phenyl)-1-morpholin-4-yl-methanone
2-Hydroxy-4-morpholin-4-yl-benzamide
2-Hydroxy-4-morpholin-4-yl-N-benzyl-benzamide
2-Hydroxy-4-morpholin-4-yl-N-phenyl-benzamide
N-Cyclopropyl-2-hydroxy-4-morpholin-4-yl-N-phenyl-benzamide
2-Hydroxy-N-(2-methoxyethyl)-4-morpholin-4-yl-benzamide
2-Hydroxy-4-morpholin-4-yl-N-methoxy-N-methyl-benzamide
2-Hydroxy-4-morpholin-4-yl-N-(3-dimethylaminopropyl)-benzamide
2-Hydroxy-N-methoxy-4-morpholin-4-yl-benzamide
2-Hydroxy-N-(2-methanesulfonylethyl)-4-morpholin-4-yl-benzamide
2-Hydroxy-4-morpholin-4-yl-N-pyridin-3-yl-benzamide
2-Hydroxy-4-morpholin-4-yl-N-pyridin-4-yl-benzamide
2-Hydroxy-4-morpholin-4-yl-N-thiazol-2-yl-benzamide
2-Hydroxy-4-morpholin-4-yl-N-(1,4-thiazin-2-yl)-benzamide
2,N-Dihydroxy-4-morpholin-4-yl-benzamide
2-Hydroxy-4-morpholin-4-yl-N-(4-pyridylmethyl)-benzamide
1-(2-Hydroxy-4-morpholin-4-yl-phenyl)-1-(4-phenylpiperizin-1-yl)-methanone
2-Hydroxy-4-morpholin-4-yl-benzoic acid
N-Carboxymethyl-2-hydroxy-4-morpholin-4-yl-phenyl)-carboxamide methyl ester
N-Carboxymethyl-2-hydroxy-4-morpholin-4-yl-phenyl-carboxamide
2-Hydroxy-4-morpholin-4-yl-thiobenzamide
2-(4-Ethylphenyl)-4-imino-7-morpholin-4-yl-benzo(e)-1,3,2-oxathiaphosphane-2-thione
1-(2-Hydroxy-4-morpholin-4-yl-phenyl)-1-phenyl-methanone
1-(2-Hydroxy-4-morpholin-4-yl-phenyl)-1-(4-trifluoromethyl-phenyl)-methanone
1-(2-Hydroxy-4-morpholin-4-yl-phenyl)-1-(o-tolyl)-methanone
1-(2-Hydroxy-4-morpholin-4-yl-phenyl)-1-(4-methoxyphenyl)-methanone
1-(2-Hydroxy-4-morpholin-4-yl-phenyl)-1-pyridin-3-yl-methanone
1-(2-Hydroxy-4-morpholin-4-yl-phenyl)-pentan-1-one
1-(2-Hydroxy-4-morpholin-4-yl-phenyl)-2-phenyl-ethanone
1-(2-Hydroxy-4-morpholin-4-yl-phenyl)-1-thiophen-2-yl-methanone
2-Hydroxy-4-morpholin-4-yl-phenyl-1,3-thiazol-2-yl ketone
1-(3-Chlorophenyl)-1-(2-hydroxy-4-morpholin-4-yl-phenyl)-methanone
2-Chloro-1-(2-hydroxy-4-morpholin-4-yl-phenyl)-ethanone
1-(2-Hydroxy-4-morpholin-4-yl-phenyl)-2-morpholin-4-yl-ethanone
1-(2-Hydroxy-4-morpholin-4-yl-phenyl)-2-imidazol-1-yl-ethanone
1-(2-Hydroxy-4-morpholin-4-yl-phenyl)-1-pyrrolidin-1-yl-methanone
1-(2-Hydroxy-4-morpholin-4-yl-phenyl)-1-(4-methylpiperazin-1-yl)-methanone
2-Hydroxy-4-morpholin-4-yl-phenyl-1-piperidin-1-yl-methanone
2-(Benzyl-methyl-amino)-1-(2-hydroxy-4-morpholin-4-yl-phenyl)-ethanone
2-Acetylthio-1-(2-hydroxy-4-morpholin-4-yl-phenyl)-ethanone
1-(2-Hydroxy-4-morpholin-4-yl-phenyl)-2-mercapto-ethanone
6-Morpholin-4-yl-2-hydrobenzo(b]furan-3-one
4-[2-Methyl-4-morpholin-4-yl-phenyl)-2-(3-pyridyl)]-1,3-thiazole
5-Morpholin-4-yl-2-(2-phenylamino-1,3-thiazol-4-yl)-phenol
3-Methoxy-1-morpholin-4-yl-benzene
4-Methoxy-2-morpholin-4-yl-benzenesulfonic acid
4-Methoxy-2-morpholin-4-yl-benzenesulfonyl chloride
4-Methoxy-N-methyl-2-morpholin-4-yl-benzenesulfonamide
4-Methoxy-2-morpholin-4-yl-N-benzyl-benzenesulfonamide
4-Methoxy-2-morpholin-4-yl-N-cyclopropylmethyl-benzenesulfonamide
N,N-Diethyl-(3-morpholin-4-yl-phenoxy)carboxamide
N,N-Diethyl-(2-benzenesulfonyl-5-morpholin-4-yl-phenoxy)carboxamide
2-Benzenesulfonyl-5-morpholin-4-yl-phenol
3-Nitro-1-morpholin-4-yl-benzene
3-Morpholin-4-yl-phenylamine
1-(2-Amino-4-morpholin-4-yl-phenyl)-2-chloro-ethanone
2-Amino-4-morpholin-4-yl-N-benzyl-N-methyl-benzamide
1-(2-Amino-4-morpholin-4-yl-phenyl)-1-pyrrolidin-1-yl-methanone
(2-Amino-4-morpholin-4-yl-phenyl)-1-piperidin-1-yl-methanone
2-Amino-4-fluorobenzoic acid methyl ester
4-Fluoro-2-(2,2,2-trifluoroacetylamino)-benzoic acid methyl ester
4-Morpholin-4-yl-2-(2,2,2-trifluoroacetylamino)-benzoic acid methyl ester
2-Amino-4-morpholin-4-yl-benzoic acid
2-Methylsulfonylamino-4-morpholin-4-yl-benzoic acid
4-Morpholin-4-yl-2-(2,2,2-trifluoroacetylamino)-N-benzyl-benzamide
N,N-Dimethyl-4-morpholin-4-yl-2-(2,2,2-trifluoroacetylamino)-benzamide
2-Amino-4-morpholin-4-yl-N,N-dimethyl-benzamide
N-Methyl-4-morpholin-4-yl-2-(2,2,2-trifluoroacetylamino)-benzamide
2-Amino-4-morpholin-4-yl-benzoic acid methyl ester
2-Acetylamino-4-morpholin-4-yl-benzoic acid methyl ester
2-Acetylamino-4-morpholin-4-yl-benzoic acid
2-Methanesulfonylamino-4-morpholin-4-yl-benzoic acid methyl ester
(2-N-Methyl-N-(2,2,2,-trifluoroacetyl)-amino]-4-morpholin-4-yl-benzoic acid methyl ester
2-Methylamino-4-morpholin-4-yl-benzoic acid methyl ester
2-Methylamino-4-morpholin-4-yl-benzoic acid
2-Chloro-1-(2-acetamido-4-morpholin-4-yl-phenyl)-ethanone
1-Acetyl-6-morpholin-4-yl-1,2-dihydro-indol-3-one
4-Morpholin-4-yl-2-nitro-benzoic acid methyl ester
4-Morpholin-4-yl-2-nitro-benzoic acid
4-Morpholin-4-yl-2-nitrophenyl)-N-(methylcarboxymethyl)benzamide
5-Hydroxy-7-morpholin-4-yl-2-phenyl-chromen-4-one
5-Hydroxy-2-phenyl-7-piperidin-1-yl-chromen-4-one
Trifluoromethanesulfonic acid 3,5-dihydroxy-4-oxo-2-phenyl-4H-chromen-7-yl ester
3,5-Dihydroxy-7-morpholin-4-yl-2-phenyl-chromen-4-one
Trifluoromethanesulfonic acid 4-acetyl-3,5-dihydroxy-phenyl ester
1-(2,6-Dihydroxy-4-morpholin-4-yl-phenyl)-ethanone
4-(5-Hydroxy-7-morpholin-4-yl-4-oxo-4H-chromen-2-yl)-benzonitrile
3-(5-Hydroxy-7-morpholin-4-yl-4-oxo-4H-chromen-2-yl)-benzonitrile
5-Hydroxy-2-(4-methoxyphenyl)-7-morpholin-4-yl-chromen-4-one
5-Hydroxy-7-morpholin-4-yl-2-pyridin-3-yl-chromen-4-one
2-Hydroxy-1-(2-hydroxy-4-morpholin-4-yl-phenyl)-ethanone
2-Hydroxy-1-(2-hydroxy-4-morpholin-4-yl-phenyl)-ethanone.

In one aspect, the pharmaceutical compositions comprise a compound of formula (I) or (II) and one or more antineoplastic agents. In a preferred embodiment, the composition comprises a chemotherapeutic agent, one or more radiotherapeutic agents, or a combination of one or more chemotherapeutic and radiotherapeutic agents in a pharmaceutically acceptable carrier or diluent. Examples of antineoplastic agents, including chemotherapeutic and radiotherapeutic agents, suitable for the invention include, but are not limited to, compounds described in Table 3 below.

invention include, but are not limited to, M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF, G-CSF, Meg-CSF, GM-CSF, thrombopoietin, stem cell factor, erythropoietin, angiopoietins, including Ang-1, Ang-2, Ang-4, Ang-Y, and/or the human angiopoietin-like polypeptide, vascular endothelial growth factor (VEGF), angiogenin, bone morphogenic protein-1 (BMP-1), BMP-2, BMP-3, BMP-4, BMP-5, BMP-6, BMP-7, BMP-8, BMP-9, BMP-10, BMP-11, BMP-12, BMP-13, BMP-14, BMP-15, BMP receptor IA, BMP receptor IB,

TABLE 3

| CHEMOTHERAPEUTIC AGENTS | | |
|---|---|---|
| Alkylating agents | Natural products | Miscellaneous agents |
| Nitrogen mustards | Antimitotic drugs | Platinium coordination complexes |
| mechlorethamine | paclitaxel | cisplatin |
| cyclophosphamide | Vinca alkaloids | carboplatin |
| ifosfamide | vinblastine (VLB) | Anthracenedione |
| melphalan | vincristine | mitoxantrone |
| chlorambucil | vinorelbine | Substituted urea |
| Nitrosoureas | Taxotere ® (docetaxel) | hydroxyurea |
| carmustine (BCNU) | estramustine | Methylhydrazine derivatives |
| lomustine (CCNU) | estramustine phosphate | N-methylhydrazine (MIH) |
| semustine (methyl-CCNU) | Epipodophylotoxins | procarbazine |
| Ethylenimine/Methylmelamine | etoposide | Adrenocortical suppressant |
| thriethylenemelamine (TEM) | teniposide | mitotane (o,p'-DDD) |
| triethylene thiophosphoramide | Antibiotics | aminoglutethimide |
| (thiotepa) | actimomycin D | Cytokines |
| hexamethylmelamine | daunomycin (rubidomycin) | interferon (α, β, γ) |
| (HMM, altretamine) | doxorubicin (adriamycin) | interleukin-2 |
| Alkyl sulfonates | mitoxantrone | Hormones and antagonists |
| busulfan | idarubicin | Adrenocorticosteroids/antagonists |
| Triazines | bleomycins | prednisone and equivalents |
| dacarbazine (DTIC) | plicamycin (mithramycin) | dexamethasone |
| Antimetabolites | mitomycinC | aminoglutethimide |
| Folic Acid analogs | dactinomycin | Progestins |
| methotrexate | Enzymes | hydroxyprogesterone caproate |
| trimetrexate | L-asparaginase | medroxyprogesterone acetate |
| Pyrimidine analogs | | megestrol acetate |
| 5-fluorouracil | Biological response modifiers | Estrogens |
| fluorodeoxyuridine | interferon-alpha | diethylstilbestrol |
| gemcitabine | IL-2 | ethynyl estradiol/equivalents |
| cytosine arabinoside | G-CSF | Antiestrogen |
| (AraC, cytarabine) | GM-CSF | tamoxifen |
| 5-azacytidine | Differentiation Agents | Androgens |
| 2,2'-difluorodeoxycytidine | retinoic acid derivatives | testosterone propionate |
| Purine analogs | Radiosensitizers | fluoxymesterone/equivalents |
| 6-mercaptopurine | metronidazole | Antiandrogens |
| 6-thioguanine | misonidazole | flutamide |
| azathioprine | desmethylmisonidazole | gonadotropin-releasing |
| 2'-deoxycoformycin | pimonidazole | hormone analogs |
| (pentostatin) | etanidazole | leuprolide |
| erythrohydroxynonyladenine | nimorazole | Nonsteroidal antiandrogens |
| (EHNA) | RSU 1069 | flutamide |
| fludarabine phosphate | EO9 | Photosensitizers |
| 2-Chlorodeoxyadenosine | RB 6145 | hematoporphyrin derivatives |
| (cladribine, 2-CdA) | SR4233 | Photofrin ® |
| Type I Topoisomerase | nicotinamide | benzoporphyrin derivatives |
| Inhibitors | 5-bromodeozyuridine | Npe6 |
| camptothecin | 5-iododeoxyuridine | tin etioporphyrin (SnET2) |
| topotecan | bromodeoxycytidine | pheoboride-a |
| irinotecan | | bacteriochlorophyll-a |
| | | naphthalocyanines |

Depending on the neoplastic condition, pharmaceutical compositions of the invention can be formulated to include one or more cytokines, lymphokines, growth factors, or other hematopoietic factors which can reduce negative side effects that may arise from, or be associated with, administration of the pharmaceutical composition alone. Cytokines, lymphokines, growth factors, or other hematopoietic factors particularly useful in pharmaceutical compositions of the brain derived neurotrophic factor, ciliary neutrophic factor, ciliary neutrophic factor receptor α cytokine-induced neutrophil chemotactic factor 1, cytokine-induced neutrophil chemotactic factor 2α, cytokine-induced neutrophil chemotactic factor 2β, β endothelial cell growth factor, endothelin 1, epidermal growth factor, epithelial-derived neutrophil attractant, fibroblast growth factor (FGF) 4, FGF 5, FGF 6, FGF 7, FGF 8, FGF 8b, FGF 8c, FGF 9, FGF 10, FGF acidic, FGF basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor, stem cell factor receptor, transforming growth factor (TGF) α, TGF β, TGF β1, TGF β1.2, TGF β2, TGF β3, TGF β5, latent TGF β1, TGF β, binding protein I, TGF β binding protein II, TGF β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

The therapeutic index of compositions comprising one or more incompounds of the invention can be enhanced by conjugation of the compound(s) with anti-tumor antibodies as previously described (for example, Pietersz and McKinzie, *Immunol. Rev.* 129:57 (1992); Trail et al., *Science* 261:212 (1993); Rowlinson-Busza and Epenetos, *Curr. Opin. Oncol.* 4:1142 (1992)). Tumor directed delivery of compounds of the invention enhances the therapeutic benefit by minimizing potential nonspecific toxicities which can result from radiation treatment or chemotherapy. In another aspect, DNA-PK inhibitor compounds and radioisotopes or chemotherapeutic agents can be conjugated to the same antibody molecule. Alternatively, DNA-PK inhibitor-conjugated tumor specific antibodies can be administered before, during, or after administration of chemotherapeutic-conjugated antitumor antibody or radioimmunotherapy.

Methods to Inhibit DNA-PK

The invention further provides methods of inhibiting DNA-PK activity comprising the step of contacting DNA-PK or a biologically active fragment thereof, with one or more compounds of formula (I) or (II). Particular examples of the compounds suitable for the method include, but are not limited to, compounds as described in Table 2. Methods of the invention include in vivo, in vitro, and ex vivo applications. Cells useful in the methods include those that express endogenous DNA-PK enzymes, "endogenous" indicating that the cells express DNA-PK absent recombinant introduction into the cells of one or more polynucleotides encoding a DNA-PK enzyme or a biologically active fragment thereof. Methods also contemplate use of cells that express exogenous DNA-PK wherein one or more polynucleotides encoding a DNA-PK enzyme or biologically active fragment thereof have been introduced into the cell using recombinant procedures. In another aspect, methods include use of cancer cells. In a preferred embodiment, methods include use of mammalian cancer cells, and in a most preferred method, the mammalian cancer cells are human cancer cells.

In vitro methods also are contemplated comprising the step of contacting DNA-PK with an inhibitor of the invention. The DNA-PK enzyme of an in vitro method can include a purified and isolated enzyme, wherein the enzyme is isolated from natural sources (i.e., cells or tissues that normally express a DNA-PK enzyme absent modification by recombinant technology) or isolated from cells modified by recombinant techniques to express an exogenous enzyme.

Methods to Identify DNA-PK Inhibitors

The invention also provides methods of identifying DNA-PK inhibitors comprising the steps of a) measuring DNA-PK enzyme activity in the presence and absence of a test compound, and b) identifying the test compound as a DNA-PK inhibitor when DNA-PK enzyme activity is decreased in the presence of the test compound. The invention contemplates in vivo and in vitro methods. In one aspect, purified and isolated DNA-PK is utilized in the method. The enzyme can be obtained from cells that naturally express the enzyme, or, alternatively, the enzyme can be obtained from cells transformed or transfected with exogenous DNA that encodes the DNA-PK enzyme. As another alternative, the enzyme can be purchased from commercial sources. In in vivo assays, cells that naturally express the DNA-PK enzyme are utilized.

Compounds that inhibit DNA-PK activity can be identified by incubating a test compound with a DNA-PK polypeptide and determining the effect of the test compound on DNA-PK activity. The selectivity of a compound that inhibits the enzyme activity can be evaluated by comparing its effects on DNA-PK to its effect on other kinase enzymes.

Selective modulators include, for example, antibodies and other proteins or peptides which specifically bind to a DNA-PK polypeptide, oligonucleotides which specifically bind to a DNA-PK polypeptide or a DNA-PK gene sequence, and other nonpeptide compounds (e.g., isolated or synthetic organic and inorganic molecules) which specifically react with a DNA-PK polypeptide or a nucleic acid encoding the polypeptide. Presently preferred targets for the development of selective inhibitors include, for example: (1) regions of the DNA-PK polypeptide that contact other proteins, (2) regions that localize the DNA-PK polypeptide within a cell wherein localization is required for specific kinase activity, (3) regions of the DNA-PK polypeptide that bind substrate, (4) regions of the polypeptide that bind DNA and result in activation of kinase activity. Inhibitors of DNA-PK activity are therapeutically useful in treatment of a wide range of diseases and physiological conditions as described herein.

Methods of the invention to identify inhibitors include variations on any of the methods known in the art to identify binding partner compounds, the variations including techniques wherein a binding partner compound (e.g., a substrate molecule or a DNA sequence that activates the kinase) has been identified and a binding assay is carried out in the presence and absence of a test inhibitor compound. An inhibitor can be identified in those instances where the level of binding between the DNA-PK polypeptide and the binding partner compound changes in the presence of the test compound compared to the level of binding in the absence of the candidate modulator compound.

In addition to the assays described above, other methods are contemplated which are designed to specifically identify DNA-PK inhibitors. In one aspect, methods of the invention use the split hybrid assay, as generally described in WO98/13502. The invention also embraces variations on this method, as described in WO95/20652.

The invention also contemplates high throughput screening (HTS) assays to identify compounds that inhibit DNA-PK biological activity (e.g., inhibit enzymatic activity, binding activity etc.). HTS assays permit screening of large numbers of compounds in an efficient manner. Cell-based HTS systems are contemplated, including melanophore assays to investigate receptor-ligand interaction, yeast-based assay systems, and mammalian cell expression systems (Jayawickreme et al., *Curr. Opin. Biotechnol.* 8:629–634 (1997)). Automated and miniaturized HTS assays are also embraced (Houston et al., *Curr. Opin. Biotechnol.* 8:734–740 (1997)). HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the DNA-PK polypeptide.

There are a number of different libraries used for the identification of compounds, and in particular small molecules, that modulate (i.e., increase or decrease) biological activity of a polypeptide of the invention, including, (1) organic and inorganic chemical libraries, (2) natural product libraries, and (3) combinatorial libraries comprised of random peptides, oligonucleotides or organic molecules.

Chemical libraries can be synthesized readily or purchased from commercial sources and consist of structural analogs of known compounds or compounds that are identified as "hits" or "leads" via natural product screening. The sources for natural product libraries are collections from microorganisms (including bacteria and fungi), animals, plants and other vegetation, or marine organisms which are used to create mixtures for screening by: (1) fermentation and extraction of broths from soil, plant or marine microorganisms or (2) extraction of plants or marine organisms. Natural product libraries include polyketides, nonribosomal peptides, and variants (nonnaturally occurring) variants thereof. For a review, see *Science* 282:63–68 (1998). Combinatorial libraries are composed of large numbers of peptides, oligonucleotides, peptide nucleic acids, or organic compounds as a mixture. They are relatively easy to prepare by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701–707 (1997).

Identification of modulators through use of the various libraries described herein permits modification of the candidate "hit" (or "lead") to optimize the capacity of the "hit" to modulate activity. Compounds that are identified in the binding assays are then tested for antagonist or agonist activity in in vivo tissue culture or animal models that are well known in the art.

The invention also provides methods of characterizing the potency of a test compound as an inhibitor of a DNA-PK polypeptide, said method comprising the steps of: (a) measuring activity of a DNA-PK polypeptide in the presence of a test compound; (b) comparing the activity of the DNA-PK polypeptide in the presence of the test compound to the activity of the DNA-PK enzyme in the presence of an equivalent amount of a reference compound of formula (I) or (II); wherein a lower activity of the DNA-PK polypeptide in the presence of the test compound than in the presence of the reference compound indicates that the test compound is a more potent inhibitor than the reference compound, and a higher activity of the DNA-PK polypeptide in the presence of the test compound than in the presence of the reference compound indicates that the test compound is a less potent inhibitor than the reference compound.

The invention further provides methods of characterizing the potency of a test compound as an inhibitor of a DNA-PK polypeptide, said method comprising the steps of: (a) determining an amount of a control compound of formula (I) or (II) that inhibits an activity of a DNA-PK polypeptide by a reference percentage of inhibition, thereby defining a reference inhibitory amount for the control compound; (b) determining an amount of a test compound that inhibits an activity of a DNA-PK polypeptide by a reference percentage of inhibition, thereby defining a reference inhibitory amount for the test compound; (c) comparing the reference inhibitory amount for the test compound to a reference inhibitory amount determined according to step (a) for the control compound of formula (I) or (II), wherein a lower reference inhibitory amount for the test compound than for the control compound indicates that the test compound is a more potent inhibitor than the control compound, and a higher reference inhibitory amount for the test compound than for the control compound indicates that the test compound is a less potent inhibitor than the control compound. In one aspect, the method utilizes a reference inhibitory amount which is the amount of the compound that inhibits the activity of the DNA-PK polypeptide by 50%, by 60%, by 70%, or by 80%. In another aspect, the method employs a reference inhibitory amount that is the amount of the compound that inhibits the activity of the DNA-PK polypeptide by 90%, by 95% or by 99%. Methods of the invention can comprise determining the reference inhibitory amount of the test compound in an in vitro biochemical assay, determining the reference inhibitory amount of the test compound in an in vitro cell-based assay, or determining the reference inhibitory amount of the test compound in an in vivo assay.

Therapeutic Methods

The invention further provides methods of sensitizing a cell to an agent that induces a DNA lesion comprising the step of contacting the cell with one or more DNA-PK inhibitors of formula (I) or (II). The preferred compounds are set forth in Table 2. In presently preferred methods, the agent that induces a DNA lesion is selected from the group consisting of radiation, exogenous chemicals, metabolite by-products, and combinations thereof. Particularly preferred methods include use of one or more chemotherapeutic/anti-neoplastic agents as set out in Table 3 that induce DNA lesions.

The invention further provides methods of potentiating a therapeutic regimen for treatment of cancer comprising the step of administering to an individual in need thereof an effective amount of a DNA-PK inhibitor of formula (I) or (II). Preferred compounds for use in the methods are set out in Table 2. In one aspect, methods include those wherein the therapeutic regimen for treatment of cancer is selected from the group consisting of chemotherapy, radiation therapy, and a combination of chemotherapy and radiation therapy. In methods wherein the therapeutic regimen includes chemotherapy, the DNA-PK inhibitor is administered before, concurrently with, and/or after administration of the chemotherapeutic/anti-neoplastic agent. In one aspect, methods include use of one or more chemotherapeutic/anti-neoplastic agents selected from the group consisting of those compounds set out in Table 3. In another aspect of the invention, the DNA-PK inhibitor is administered before, concurrently with, or after administration of a cytokine, lymphokine, growth factor, or hematopoietic factor as described herein.

Compounds of the invention are useful in instances where radiation and chemotherapy are indicated to enhance the therapeutic benefit of these treatments, including induction chemotherapy, primary (neoadjuvant) chemotherapy, and both adjuvant radiation therapy and adjuvant chemotherapy. In addition, radiation and chemotherapy frequently are indicated as adjuvants to surgery in the treatment of cancer. The goal of radiation and chemotherapy in the adjuvant setting is to reduce the risk of recurrence and enhance disease-free survival when the primary tumor has been controlled. Chemotherapy is utilized as a treatment adjuvant for colon, lung, and breast cancer, frequently when the disease is metastatic. Adjuvant radiation therapy is indicated in several diseases including colon, lung, and breast cancers as described above. For example, radiation frequently is used both pre- and post-surgery as components of the treatment strategy for rectal carcinoma. Compounds of the invention therefore are particularly useful following surgery in the treatment of cancer in combination with radio- and/or chemotherapy.

The invention further relates to radiosensitizing tumor cells utilizing a compound of formula (I) or (II). The preferred compounds are those as described for the pharmaceutical compositions of the invention. Particular examples of the compounds suitable for the method include, but are not limited to, compounds as described in Table 2. A compound that can "radiosensitize" a cell, as used herein, is defined as a molecule, preferably a low molecular weight molecule, administered to animals in therapeutically effective amount to increase the sensitivity of cells to electromagnetic radiation and/or to promote the treatment of diseases that are treatable with electromagnetic radiation. Diseases that are treatable with electromagnetic radiation include neoplastic diseases, benign and malignant tumors, and cancerous cells.

Electromagnetic radiation treatment of other diseases not listed herein is also contemplated by the present invention. The terms "electromagnetic radiation" and "radiation" as used herein include, but are not limited to, radiation having the wavelength of $10^{-20}$ to 1 meter. Preferred embodiments of the present invention employ the electromagnetic radiation of: gamma-radiation ($10^{-20}$ to $10^{-13}$ m), X-ray radiation ($10^{-12}$ to $10^{-9}$ m), ultraviolet light (10 nm to 400 mn), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Several mechanisms for the mode of action of radiosensitizers have been suggested. Hypoxic cell radiosensitizers (e.g., 2-nitroimidazole compounds, and benzotriazine dioxide compounds) promote reoxygenation of hypoxic tissue and/or catalyze generation of damaging oxygen radicals. Nonhypoxic cell radiosensitizers (e.g., halogenated pyrimidines) can be analogs of DNA bases and preferentially incorporate into the DNA of cancer cells and thereby promote the radiation ion-induced breaking of DNA molecules and/or prevent the normal DNA repair mechanisms. Various other potential mechanisms of action have been hypothesized for radiosensitizers in the treatment of disease.

Many cancer treatment protocols currently employ radiosensitizers activated by electromagnetic radiation, e.g., X-rays. Examples of X-ray-activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more other compounds, including but not limited to, compounds that promote the incorporation of radiosensitizers to the target cells; compounds that control the flow of therapeutics, nutrients, and/or oxygen to the target cells; chemotherapeutic agents that act on the tumor with or without additional radiation; or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, anti-angiogenesis compounds, hydralazine, and L-BSO. Examples of chemotherapeutic agents that can be used in conjunction with radiosensitizers include, but are not limited to, adriamycin, camptothecin, carboplatin, cisplatin, daunorubicin, doxorubicin, interferon (alpha, beta, gamma), interleukin 2, irinotecan, docetaxel, paclitaxel, topotecan, and therapeutically effective analogs and derivatives of the same.

The invention also can be practiced by including another anti-cancer chemotherapeutic agent with a compound of the invention, such as any conventional chemotherapeutic agent. The combination of the inhibitor compound with such other agents can potentiate the chemotherapeutic protocol. Numerous chemotherapeutic protocols known to the skilled practitioner as being capable of incorporation into the method of the invention. Any chemotherapeutic agent can be used, including alkylating agents, antimetabolites, hormones and antagonists, radioisotopes, as well as natural products. For example, the inhibitor compound of the invention can be administered with antibiotics, such as doxorubicin and other anthracycline analogs, nitrogen mustards, such as cyclophosphamide, pyrimidine analogs, such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other anti-neoplastic protocols include the use of an inhibitor compound with another treatment modality, e.g., surgery, radiation etc., also referred to herein as "adjunct anti-neoplastic modalities." Thus, the method of the invention can be employed with such conventional regimens with the benefit of reducing side effects and enhancing efficacy.

The present invention also provides methods of treating cancer in an animal, comprising administering to the animal an effective amount of a compound that inhibits DNA-PK activity, such as a compound of formula (I) or (II). The preferred compound is selected from the group of compounds set forth in Table 2. The invention further is directed to methods of inhibiting cancer cell growth, including processes of cellular proliferation, invasiveness, and metastasis in biological systems. Methods include use of a compound of formula (I) or (II) as an inhibitor of cancer cell growth. Preferably, the methods are employed to inhibit or reduce cancer cell growth, invasiveness, metastasis, or tumor incidence in living animals, such as mammals. Methods of the invention also are readily adaptable for use in assay systems, e.g., assaying cancer cell growth and properties thereof, as well as identifying compounds that affect cancer cell growth.

Compounds of the invention possess one or more desirable, but unexpected, combinations of properties, including increased activity and/or solubility, and reduction of adverse side effects. These compounds have been found to inhibit cancer growth, including proliferation, invasiveness, and metastasis, thereby rendering them particularly desirable for the treatment of cancer. In particular, compounds of the invention exhibit cancer-inhibitory properties at concentrations that appear to be substantially free of side effects. These compounds therefore are useful for extended treatment protocols, where the use of conventional chemotherapeutic compounds can exhibit undesirable side effects. For example, the co-administration of a compound of the invention with another, more toxic, chemotherapeutic agent can achieve beneficial inhibition of a cancer, while effectively reducing the toxic side effects in the patient.

In addition, the properties of hydrophilicity and hydrophobicity of the compounds of the invention are well balanced, thereby enhancing their utility for both in vitro and especially in vivo uses, while other compounds lacking such balance are of substantially less utility. Specifically, compounds of the invention have an appropriate degree of solubility in aqueous media which permits absorption and bioavailability in the body, while also having a degree of solubility in lipids which permits the compounds to traverse the cell membranes, including the nuclear membrane, to a putative site of action. Thus, compounds of the invention are maximally effective when delivered to the site of the tumor and they enter the tumor cells.

The cancers treatable by methods of the present invention preferably occur in mammals. Mammals include, for example, humans and other primates, as well as pet or companion animals, such as dogs and cats, laboratory animals, such as rats, mice and rabbits, and farm animals, such as horses, pigs, sheep, and cattle.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells which infiltrate (invade) the surrounding tissues and give rise to metastases. Adenocarcinomas are carcinomas derived from glandular tissue, or from tissues which form recognizable glandular structures. Another broad category of cancers includes sarcomas, which are tumors whose cells are embedded in a fibrillar or homogeneous substance like embryonic connective tissue. The invention also enables treatment of cancers of the myeloid or lymphoid systems, including leukemias, lymphomas, and other cancers that typically do not present as a tumor mass, but are distributed in the vascular or lymphoreticular systems.

DNA-PK activity can be associated with various forms of cancer in, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma. Methods to potentiate treatment of these and other forms of cancer are embraced by the invention.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens. However, it will be understood that the method of the invention is not limited to the treatment of these tumor types, but extends to any tumor derived from any organ system. Cancers whose invasiveness or metastasis is associated with DNA-PK expression or activity are especially susceptible to being inhibited or even induced to regress by means of the invention.

In addition to the neoplastic conditions described above, DNA-PK activity can be correlated with other pathologies including aberrant apoptotic mechanisms, such as abnormal caspase activity; aberrant enzyme activity associated with cell cycle progression, include for example cyclins A, B, D and E; alterations in viral (e.g., Epstein-Barr virus, papillomavirus) replication in latently infected cells; chromosome structure abnormalities, including genomic stability in general, unrepaired chromosome damage, telomere erosion (and telomerase activity), breakage syndromes including for example, Sjögren's syndrome, Bloom's syndrome, and Nijmegen breakage syndrome; embryonic stem cell lethality; abnormal embryonic development; sensitivity to ionizing radiation; acute immune complex alveolitis; and Fanconi anemia. Treatment of these pathological conditions, and others that arise from enhanced DNA-PK activity, also is embraced by the invention.

The present invention also includes methods to inhibit retroviral infection utilizing a compound of the invention. DNA-PK participates in nonhomologous end joining (NHEJ) of chromosomal DNA and retroviral DNA integration into the host genome in accomplished through this type of NHEJ reaction (Daniel et al., *Science*, 284:644–647 (1999)). Inhibition of DNA-PK therefore can prevent retroviral DNA from integrating into the host genome in infected cells. Because retroviral genomic integration occurs after infections, it is unlikely that inhibition of DNA-PK affects early stages of infection. Instead, inhibiting DNA-PK prevents repair of chromosomal breakage associated with integration and therefore signal apoptosis for the infected cell. Assays to assess the ability of DNA-PK inhibitors to act in this manner can be carried out by measuring apoptosis with virally infected cells in the presence and absence of a DNA-PK inhibitor.

Because many anti-cancer drugs are also immunosuppressive, the DNA-PK inhibitors also can be used to potentiate the efficacy of drugs in the treatment of inflammatory diseases. In particular, the method of the invention can be employed to treat humans therapeutically or prophylactically who are or may subject to an inflammatory disorder. "Inflammatory disorder" as used herein can refer to any disease, disorder, or syndrome in which an excessive or unregulated inflammatory response leads to excessive inflammatory symptoms, host tissue damage, or loss of tissue function. "Inflammatory disorders" can also refer to pathological states mediated by influx of leukocytes and or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and or neutrophil chemotaxis. Inflammation can result from infection with pathogenic organisms and viruses and from noninfectious means, such as trauma or reperfusion following myocardial infarction or stroke, immune response to foreign antigen, and autoimmune responses. Accordingly, inflammatory disorders amenable to the invention encompass disorders associated with reactions of the specific defense system as well as with reactions of the nonspecific defense system.

As used herein, the term "specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD) are fuirther examples of inflammatory reactions of the specific defense system.

The term "nonspecific defense system" as used herein refers to inflammatory disorders that are mediated by leukocytes that are incapable of immunological memory (e.g., granulocytes, macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents. "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue (including organs or cells, e.g., bone marrow), characterized by a loss of function of the grafted and surrounding tissues, pain, swelling, leukocytosis, and thrombocytopenia.

The therapeutic methods of the present invention include methods for the amelioration of disorders associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The present invention enables methods of treating various diseases associated with or characterized by inflammation, for example, arthritic diseases such as rheumatoid arthritis, osteoarthritis, gouty arthritis, spondylitis; Behcet's disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders, such as allergic conjunctivitis, vernal conjunctivitis, uveitis, and thyroid-associated ophthalmopathy; eosinophilic granuloma; pulmonary or respiratory disorders, such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, pneumonia, bronchiectasis, and pulmonary oxygen toxicity; reperfusion injury of the myocardium, brain, or extremities; fibrosis, such as cystic fibrosis; keloid formation or scar tissue formation; atherosclerosis; autoimmune diseases such as systemic lupus erythematosus (SLE), autoimmune thyroiditis, multiple sclerosis, some forms of diabetes, and Reynaud's syndrome; transplant rejection disorders, such as GVHD and allograft rejection; chronic glomerulonephritis; inflammatory bowel diseases such as Crohn's disease, ulcerative colitis and necrotizing enterocolitis; inflammatory dermatoses, such as contact dermatitis, atopic dermatitis, psoriasis, or urticaria; fever and myalgias due to infection; central or peripheral nervous system inflammatory disorders, such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion associated syndromes; and cytokine-induced toxicity.

Methods of the invention can be used with animal models in order to assess the efficacy of compounds of the invention. For example, animal models used in the study of inflammatory bowel disease (EBD) are generally elicited by intrarectal administration of noxious irritants (e.g., acetic acid or trinitrobenzene sulfonic acid/ethanol). Colonic inflammation induced by these agents is the result of chemical or metabolic injury and lacks the chronic and spontaneously relapsing inflammation associated with human IBD. However, a recently described model using subserosal injections of purified peptidoglycan-polysaccharide (PG-PS) polymers from either group A or group D streptococci appears to be a more physiologically relevant model for human IBD (Yamada et al., *Gastroenterology*, 104:759–771 (1993)).

In this model, PG-PS is injected into the subserosal layer of the distal colon. The resulting inflammatory response is biphasic with an initial acute episode three days after injection, which is followed by a spontaneous chronic phase three to four weeks later. The late phase response is granulomatous in nature, and results in colonic thickening, adhesions, colonic nodules and mucosal lesions. In general, granulomatous lesions are the result of chronic inflammation which leads to the recruitment and subsequent activation of cells of the monocyte/macrophage lineage. In addition to mucosal injury, PG-PS colitis frequently leads to arthritis, anemia, and granulomatous hepatitis. The extraintestinal manifestations of the disease make the model attractive for studying Crohn's colitis in that a significant number of patients with active Crohn's disease suffer from arthritic joint disease and hepatobiliary inflammation.

Methods of the invention have particular utility in treating humans who are or may be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of DNA-PK expression or activity will result in reduced amounts of reperfusion injury in such situations.

With respect to the nervous system, global ischemia occurs when blood flow to the entire brain ceases for a period. Global ischemia can result from cardiac arrest. Focal ischemia occurs when a portion of the brain is deprived of its normal blood supply. Focal ischemia can result from thromboembolic occlusion of a cerebral vessel, traumatic head injury, edema, or brain tumor. Even if transient, both global and focal ischemia can cause widespread neuronal damage. Although nerve tissue damage occurs over hours or even days following the onset of ischemia, some permanent nerve tissue damage may develop in the initial minutes following the cessation of blood flow to the brain. Much of this damage has been attributed to glutamate toxicity and to the secondary consequences of tissue reperfusion, such as the release of vasoactive products by damaged endothelium and the release of cytotoxic products, such as free radicals and leukotrienes, by the damaged tissue.

Ischemia also can occur in the heart in myocardial infarction and other cardiovascular disorders in which the coronary arteries have been obstructed as a result of atherosclerosis, thrombus, or spasm. For example, the method of the invention is believed to be useful for treating cardiac tissue damage, particularly damage resulting from cardiac ischemia or caused by reperfusion injury in mammals.

Administration

The compounds and pharmaceutical compositions of the invention can be administered to humans and other animals by any suitable route. For example, the compositions can be administered orally, including sublingually, rectally, parenterally, intracisternally, intravaginally, intraperitoneally, topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the invention under the splenic capsule, brain, or in the cornea.

Compounds of the present invention also can be administered in the form of liposomes. As is known in the art, liposomes generally are derived from phospholipids or other lipid substances. Liposomes are formed by mono- or multi-lamellar hydrated liquid crystals that are dispersed in an aqueous medium. Any nontoxic, physiologically acceptable, and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology, Volume XIV*, Academic Press, New York, N.Y. (1976), p. 33, et seq.

The compounds of the present invention can be used in the form of pharmaceutically acceptable salts derived from inorganic or organic acids. By "pharmaceutically acceptable salt" is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 66:1 (1977). The salts can be prepared in situ during the final isolation and purification of the compounds of the invention or separately by reacting a free base fimction with a suitable acid. Representative acid addition salts include, but are not limited to acetate, adipate, alginate, citrate, aspartate, benzoate, benzenesulfonate, bisulfate, butyrate, camphorate, camphorolsulfonate, digluconate, glycerophosphate, hemisulfate, heptanoate, hexanoate, fumarate hydrochloride, hydrobromide, hydrojodide, 2-hydroxyethanesulfonate (isothionate), lactate, maleate, methanesulfonate, nicotinate, 2-Naphthalenesulfonate, oxalate, pamoate, pectinate, persulfate, 3-phenyl-propionate, picrate, pivalate, propionate, succinate, tartrate, thiocyanate, phosphate, glutamate, bicarbonate, p-toluenesulfonate and undecanoate. Examples of acids that can be employed form pharmaceutically acceptable acid addition salts include inorganic acids, such as hydrochloric acid, hydrobromic acid, sulfuric acid, and phosphoric acid, and organic acids, such as oxalic acid, maleic acid, succinic acid, and citric acid.

Basic nitrogen-containing groups can be quatemized with such agents as lower alkyl halides such as methyl, ethyl, propyl, and butyl chlorides, bromides, and iodides; dialkyl sulfates like dimethyl, diethyl, dibutyl and diamyl sulfates; long chain halides such as decyl, lauryl, myristyl, and stearyl chlorides, bromides, and iodides; and arylalkyl halides, like benzyl and phenethyl bromides and others. Water or oil-soluble or dispersible products thereby are obtained.

Basic addition salts can be prepared in situ during the final isolation and purification of compounds of this invention by reacting a carboxylic acid-containing moiety with a suitable base, such as a hydroxide, carbonate, or bicarbonate of a pharmaceutically acceptable metal cation or with ammonia or organic primary, secondary, or tertiary amine. Pharmaceutically acceptable basic addition salts include, but are not limited to, cations based on alkali metals or alkaline earth metals, such as lithium, sodium, potassium, calcium, magnesium, and aluminum, and the like, and nontoxic quaternary ammonia and amine cations including ammonium, tetramethylammonium, tetraethyl-ammonium, methylamine, dimethylamine, trimethylamine ethylamine, diethylamine, triethylamine, and the like. Other representative organic amines useful for the formation of base addition salts include ethylenediamine, ethanolamine, diethanolamine, piperidine, piperazine, and the like.

Dosage forms for topical administration of a compound of this invention include powders, sprays, ointments, and inhalants as described herein. The active compound is mixed under sterile conditions with a pharmaceutically acceptable carrier and any needed preservatives, buffers, or propellants which may be required. Ophthalmic formulations, eye ointments, powders, and solutions also are contemplated as being within the scope of this invention.

Parenteral Administration

Pharmaceutical compositions of the invention for parenteral injection comprise pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and non-aqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions also can contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin.

In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution which, in turn, may depend upon crystal size and crystalline form. Alternatively, delayed absorption of a parenterally administered drug from is accomplished by dissolving or suspending the drug in an oil vehicle.

Injectable depot forms are made by forming microencapsule matrices of the drug in biodegradable polymers such a polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissue.

The injectable formulations can be sterilized, for example, by filtration through a bacterial- or viral-retaining filter, or by incorporating sterilizing agents in the form of sterile solid compositions which can be dissolved or dispersed in sterile water or other sterile injectable medium just prior to use.

Oral Administration

The invention provides methods for oral administration of a pharmaceutical composition of the invention. Oral solid dosage forms are described generally in *Remington's Pharmaceutical Sciences*, 18th Ed., 1990 (Mack Publishing Co. Easton Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). Liposomal encapsulation may include liposomes that are derivatized with various polymers (e.g., U.S. Pat. No. 5,013,556). In general, the formulation includes a compound of the invention and inert ingredients which protect against degradation in the stomach and which permit release of the biologically active material in the intestine.

In such solid dosage forms, the active compound is mixed with, or chemically modified to include, a least one inert, pharmaceutically acceptable excipient or carrier. The excipient or carrier preferably permits (a) inhibition of proteolysis, and (b) uptake into the blood stream from the stomach or intestine. In a most preferred embodiment, the excipient or carrier increases uptake of the compound, overall stability of the compound and/or circulation time of the compound in the body. Excipients and carriers include, for example, sodium citrate or dicalcium phosphate and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO™, EMDEX™, STA-RX 1500™, EMCOMPRESS™ and AVICEL™.; (b) binders such as, for example, methylcellulose ethylcellulose, hydroxypropyhnethyl cellulose, carboxymethylcellulose, gums (e.g., alginates, acacia), gelatin, polyvinylpyrrolidone, and sucrose, (c) humectants, such as glycerol, (d) disintegrating agents, such as agar-agar, calcium carbonate, potato or tapioca starch, alginic acid, certain silicates, sodium carbonate, starch including the commercial disintegrant based on starch, EXPLOTAB™, sodium starch glycolate, AMBERLITE™, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such a paraffm, (f) absorption accelerators, such as quaternary ammonium compounds and fatty acids including oleic acid, linoleic acid, and linolenic acid (g) wetting agents, such as, for example, cetyl alcohol and glycerol monosterate, anionic detergent surfactants including sodium lauryl sulfate, dioctyl sodium sulfosuccinate, and dioctyl sodium sulfonate, cationic detergents, such as benzalkonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay, (i) lubricants, such as talc, calcium sterate, magnesium stearate, solid polyethylene glycols, sodium lauryl sulfate, polytetrafluoroethylene (PTFE), liquid paraffin, vegetable oils, waxes, CARBOWAX™ 4000, CARBOWAX™ 6000, magnesium lauryl sulfate, and mixtures thereof; (j) glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

Solid compositions of a similar type also can be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells, such as enteric coatings and other coatings well known in the pharmaceutical formulating art. They optionally can contain opacifying agents and also can be of a composition that they release the active ingredients(s) only, or preferentially, in a part of the intestinal tract, optionally, in a delayed manner. Exemplary materials include polymers having pH sensitive solubility, such as the materials available as EUDRAGIT®. Examples of embedding compositions which can be used include polymeric substances and waxes.

The active compounds also can be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms can contain inert diluents commonly used in the art, such as, for example, water or other solvents, solubilizing agents and emulsifiers, such as ethyl alcohol, isopropyl alcohol ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydroflirfuryl alcohol, polyethylene glycols, fatty acid esters of sorbitan, and mixtures thereof.

Besides inert diluents, the oral compositions also can include adjuvants, such as wetting agents, emulsifying and suspending agents, sweetening, coloring flavoring, and perfuming agents. Oral compositions can be formulated and further contain an edible product, such as a beverage.

Suspensions, in addition to the active compounds, can contain suspending agents such as, for example ethoxylated isostearyl alcohols, polyoxyethylene sorbitol and sorbitan esters, microcrystalline cellulose, aluminum metahydroxide, bentonite, agar-agar, tragacanth, and mixtures thereof.

Pulmonary Administration

Also contemplated herein is pulmonary delivery of a DNA-PK inhibitor (or derivatives thereof). The inhibitor is delivered to the lungs of a mammal while inhaling, thereby promoting the traversal of the lung epithelial lining to the blood stream. See, Adjei et al., *Pharmaceutical Research* 7:565–569 (1990); Adjei et al., *International Journal of Pharmaceutics* 63:135–144 (1990) (leuprolide acetate); Braquet et al., *Journal of Cardiovascular Pharmacology* 13 (*suppl.*5): s.143–146 (1989)(endothelin-1); Hubbard et al., *Annals of Internal Medicine* 3:206–212 (1989)(α1-antitrypsin); Smith et al., *J. Clin. Invest.* 84:1145–1146 (1989) (α1-proteinase); Oswein et al., "Aerosolization of Proteins," Proceedings of Symposium on Respiratory Drug Delivery II, Keystone, Colorado, March, 1990 (recombinant human growth hormone); Debs et al., *The Journal of Immunology* 140:3482–3488 (1988) (interferon-γ and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including, but not limited to, nebulizers, metered dose inhalers, and powder inhalers, all of which are familiar to those skilled in the art.

Some specific examples of commercially available devices suitable for the practice of the invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOLIN® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of a compound of the invention. Typically, each formulation is specific to the type of device employed and can involve the use of an appropriate propellant material, in addition to diluents, adjuvants, and/or carriers useful in therapy.

The inhibitor composition is prepared in particulate form, preferably with an average particle size of less than 10 μm, and most preferably 0.5 to 5 μm, for most effective delivery to the distal lung.

Carriers include carbohydrates such as trehalose, mannitol, xylitol, sucrose, lactose, and sorbitol. Other ingredients for use in formulations may include lipids, such as DPPC, DOPE, DSPC and DOPC, natural or synthetic surfactants, polyethylene glycol (even apart from its use in derivatizing the inhibitor itself), dextrans, such as cyclodextran, bile salts, and other related enhancers, cellulose and cellulose derivatives, and amino acids.

Also, the use of liposomes, microcapsules or microspheres, inclusion complexes, or other types of carriers is contemplated.

Formulations suitable for use with a nebulizer, either jet or ultrasonic, typically comprise a compound of the invention dissolved in water at a concentration of about 0.1 to 25 mg of biologically active protein per mL of solution. The formulation also can include a buffer and a simple sugar (e.g., for protein stabilization and regulation of osmotic pressure). The nebulizer formulation also can contain a surfactant to reduce or prevent surface-induced aggregation of the inhibitor composition caused by atomization of the solution in forming the aerosol.

Formulations for use with a metered-dose inhaler device generally comprise a finely divided powder containing the inhibitor compound suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid also can be useful as a surfactant.

Formulations for dispensing from a powder inhaler device comprise a finely divided dry powder containing the inhibitor and also can include a bulking agent, such as lactose, sorbitol, sucrose, mannitol, trehalose, or xylitol, in amounts which facilitate dispersal of the powder from the device, e.g., 50 to 90% by weight of the formulation.

Other Routes of Administration

Nasal delivery of the inhibitor also is contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes also is contemplated.

Compositions for rectal or vaginal administration are preferably suppositories which can be prepared by mixing the compounds of the invention with suitable nonirritating excipients or carriers, such as cocoa butter, polyethylene glycol, or suppository wax, which are solid at room temperature, but liquid at body temperature, and therefore melt in the rectum or vaginal cavity and release the active compound.

In order to facilitate delivery of compounds across cell and/or nuclear membranes, compositions of relatively high hybrophobicity are preferred. Compounds can be modified in a manner which increases hydrophobicity, or the compounds can be encapsulated in hydrophobic carriers or solutions which result in increased hydrophobicity.

Dosages

Actual dosage levels of active ingredients in the pharmaceutical compositions of the invention can be varied to obtain an amount of the active compound(s) that is effective to achieve the desired therapeutic response for a particular patient, compositions, and mode of administration. The selected dosage level depends upon the activity of the particular compound, the route of administration, the severity of the condition being treated, and the condition and prior medical history of the patient being treated. However, it is within the skill of the art to start doses of the compound at levels lower than required to achieve the desired therapeutic effort and to gradually increase the dosage until the desired effect is achieved.

Generally dosage levels of about 0.1 to about 1000 mg, about 0.5 to about 500 mg, about 1 to about 250 mg, about 1.5 to about 100, and preferably of about 5 to about 20 mg of active compound per kilogram of body weight per day are administered orally or intravenously. If desired, the effective daily dose can be divided into multiple doses for purposes of administration, e.g., two to four separate doses per day.

The invention is exemplified by the following examples. Example 1 describes DNA-PK enzyme purification. Example 2 sets forth the standard DNA-PK enzyme assay. Example 3 describes a high throughput assay used to identify inhibitors of DNA-PK. Example 4 addresses determination of selectivity of the DNA-PK inhibitors identified. Example 5 relates to assessing cellular toxicity of the DNA-PK inhibitors. Example 6 describes a V(D)J recombination assay. Example 7 provides an assay to determine the chemosensitization capacity of DNA-PK inhibitors. Example 8 addresses the ability of DNA-PK inhibitors to affect long term cell proliferation. Example 9 relates to assessment of the ability of a representative DNA-PK inhibitor to potentiate the toxic effect of radiation treatment. Example 10 describes the ability of DNA-PK inhibitors to reduce/inhibitor tumor formation in animal models. Example 11 addresses use of DNA-PK inhibitors in the treatment of human diseases. Examples 12–149 provide a description of methods for synthesis and physical properties of exemplary DNA-PK inhibitors of the invention.

EXAMPLE 1

DNA-PK Enzyme Purification

In order to develop an assay to screen for enzyme inhibitors, a method for large scale purification of human DNA-PK was performed (Lees-Miller et al., *Mol. Cell. Biol.* 10:6472–6481 (1990)).

HeLa S3 cells (ATCC CCL-2.2; Batch F12594) were raised in MEM-Joklik media (Gibco) supplemented with 10% FBS, 100 U/mL penicillin and 100 µg/mL streptomycin at 37° C. in a humidified chamber under 5% $CO_2$. For enzyme purification, cells were grown to a density of approximately $1 \times 10^6$ cells/mL in two spinner flasks each containing 6 L media. Cells were collected by centrifugation for 10 min at 1,000 rpm in a GS-6R Beckman centrifuge. Cell pellets were washed 1× in ice cold PBS and collected by centrifugation. Cells were resuspended in ice cold LSB buffer, containing 10 mM HEPES-KOH, pH 7.2, 25 mM KCl, 10 mM NaCl, 1 mM $MgCl_2$, 0.1 mM EDTA, and 0.1 mM DTT, and collected by centrifugation for 10 min at 2,000 rpm. Cell pellets were resuspended in an equal volume of buffer, allowed to stand on ice for 5 min, and then frozen in liquid nitrogen.

The frozen HeLa cell pellet was thawed at 37° C. and immediately centrifuged at 10,000×g in a Beckman JA10 rotor for 20 min at 4° C. The resulting supernatant (S10 faction, fraction I) was collected, solid PMSF was added to 0.5 mM final concentration, and the resulting mixture was centrifuged at 100,000×g in a Beckman Type 45Ti rotor for 3 h at 4° C. The pelleted material was resuspended in H buffer (containing 25 mM HEPES-KOH, pH 7.5, 0.2 mM EDTA, 0.5 mM DTT, 0.5 M KCl, and 10 mM $MgCl_2$) and centrifuged at 100,000×g for 1 h at 4° C. H Buffer was added to the supernatant until the ionic strength was equal to that of H buffer containing 0.1 M KCl (S100-2 fraction, also fraction II).

The S100-2 fraction was applied to a 28 mL Q-SEPHAROSE® FF column (1.5×16 cm) equilibrated in H buffer with 0.1 M KCl. The resin was washed with 5 column volumes and developed with a 140 mL linear gradient (0.1 to 0.5 M KCl in H buffer) at a flow rate of 1.5 mL/min. A broad peak of activity was eluted, pooled, and dialyzed into H buffer with 0.1 M KCl (fraction III).

Fraction III was applied to an 8 mL SP-SEPHAROSE® FF column (1×10 cm) equilibrated in H buffer with 0.1 M KCl. The resin was washed with 5 column volumes and developed with a 30 mL linear gradient (0.1 to 0.5 M KCl in H buffer) at a flow rate of 1.5 mL/min. Active fractions were pooled (fraction IV) and stored at −70° C.

EXAMPLE 2

Standard DNA-PK Assay

Standard kinase reactions used to measure phosphorylation of a p53 peptide substrate (SEQ ID NO: 1) contained, in 20 μL, 25 mM HEPES-KOH, pH 7.5, 10 mM $MgCl_2$, 0.5 mM DTT, 50 μM ATP, 0.01 mCi/mL ($\gamma$-$^{32}$P]ATP, 10 μg/mL replicative form III (RFIII) DNA, 200 μM p53 peptide and 0.2 μg purified DNA-PK (as described in Example 1).

Glu-Pro-Pro-Leu-Ser-Gln-Glu-Ala-Phe-Ala-Asp-Leu-
    Trp-Lys-Lys-Arg                SEQ ID NO: 1

Reactions were carried out at room temperature. Reactions were started by addition of ATP and stopped by application to phosphocellulose paper. Reaction products spotted onto phosphocellulose paper were washed five times with a total volume of at least 250 mL 10% acetic acid or 150 mM phosphoric acid. The paper was air dried and radioactivity was determined in a Beckman LS6000IC scintillation counter.

The DNA-PK kinase activity was found to be stimulated 17-fold in the presence of linear duplex RFIII DNA and activity was dependent upon addition of polypeptide substrate. The $K_m$ and $V_{max}$ for ATP consumption were found to be 6.6 μM ATP and 1.2 pmol ATP/min, respectively. Enzyme activity was inhibited by wortmannin with an $IC_{50}$=100 to 250 nM and by demethoxyviridin at an $IC_{50}$=5 nM.

EXAMPLE 3

High-Throughput DNA-PK Kinase Assay

In order to screen large numbers of compounds for the ability to inhibit DNA-PK activity, an automated high throughput screening assay was developed. The steps in the automated procedure are as set out below.

A stock ($^{32}$P]-ATP mixture was prepared containing 0.5 mM p53 peptide (SEQ ID NO: 1), 125 μM ATP, 25 μg/mL DNA, 2.5×DNA-PK Buffer (62.5 HEPES-KOH, pH 7.5, 25 mM $MgCl_2$, 1.25 mM DTT), and 6.25 μCi/mL $^{32}$P-ATP. The stock mixture was prepared in a 100 mL volume containing 25 mL 2 mM p53 peptide, 2.5 mL 5 mM ATP, 2.5 mg DNA (volume depends on concentration of DNA available), 50 mL 5×DNA-PK Buffer, 625 μL ($^{32}$P]-ATP, and 22.0 mL $H_2O$ (minus volume of DNA used). Approximately 50 mL of the mixture was dispensed into a reagent reservoir in the assay apparatus, and the remaining $^{32}$P-ATP mix was stored at 4° C.

Enzyme dilution buffer (EDB) (containing 25 mM HEPES-KOH, pH 7.5, 10 mM $MgCl_2$, 0.5 mM DTT) was diluted 1:2 (20 mL EDB diluted with 20 mL $H_2O$) and the diluted buffer was transferred to the assay apparatus. A 1.0 mL aliquot of DNA-PK enzyme was thawed, 225 μL enzyme was added to 45 mL diluted EDB, and the mixture was vortexed. The diluted enzyme was transferred to the assay apparatus for the first round of assays, and the remaining undiluted enzyme was dispensed into 150 μL aliquots. For subsequent sets of 15 plates, the 150 μL aliquots of DNA-PK enzyme were added to 30 mL of diluted EDB.

In the assay, a Sagian/SAMI protocol runs a program designated "DNA-PK" which included the following steps. In a first step, 100 μL of 150 mM phosphoric acid was added to each well on a MILLIPORE® filter plate. The phosphoric acid was vacuumed through and an assay plate with controls, a chemical plate, and a dilution plate containing 198 μL $H_2O$ were loaded. The program then added 2 μL assay chemical to dilution plate, mixed the dilution plate, and transferred 20 μL of the diluted chemical to the assay plate. The pipette tips were washed and 20 μL of enzyme was transferred to the assay plate. The tips were washed again and 20 μL $^{32}$P-ATP mix was added to the assay plate. The reaction was mixed and incubated for 20 min.

The program then pipetted 10 μL 150 mM phosphoric acid into the assay plate and mixed the phosphoric acid with the assay mix to stop the reaction. The filter plates were allowed to incubate at least 10 mins before washing to ensure complete binding of the phosphorylated peptide.

After the 10 min incubation, the MILLIPORE® plate was transferred to a wash station and aspirated. Another 200 μL 1.5 mM phosphoric acid was added to each well and the plate was aspirated again. This step was repeated four more times so that a total of five 200 μL phosphoric acid washes were completed. Using an 8 channel pipette, 100 μL 95% ethanol was added to each well and the liquid aspirated through. The plates were blotted on paper towels several times and allowed to air dry approximately 10 to 15 min. Scintillation fluid (50 μL) was added to each well and radioactivity was counted using a Wallac beta counter.

Inhibitors of DNA-PK-catalyzed protein phosphorylation were identified through an analysis of an internal chemical library. This screen yielded 47 compounds with $IC_{50}$ values less than 52 μM. These compounds were defined as hits and tested further.

EXAMPLE 4

Selectivity Determination

The most potent inhibitors of DNA-PK identified in the high throughput screening assay were tested for the ability to inhibit phosphorylation catalyzed by other kinase enzymes. In order to distinguish the DNA-PK specific inhibitors from general protein kinase inhibitors, the inhibitors identified in Example 2 were used in assays with distantly related (from a phylogenic standpoint) protein kinases (Hunter and Plowman, *Trends Biochem Sci* 22:18–22 (1997)) casein kinase I, protein kinase Cθ and the calcium/calmodulin dependent kinase II. To identify which inhibitors preferentially bound to DNA-PK from a set of more closely related kinases, the compounds were assayed for inhibitory activity against the ataxia-telangiectasia related (ATR) protein kinase, the FK506-rapamycin associated protein kinase, and the phosphatidylinositol-3 kinase p110δ. Compounds that selectively inhibited phosphorylation catalyzed by DNA-PK were defined as specific inhibitors of DNA-PK. Selectivity of inhibition can be defined as follows:

($IC_{50}$(test enzyme))/($IC_{50}$(DNA-PK))>50

All assays were carried out at room temperature in polypropylene microfuge tubes or polystyrene microtiter plates.

P110 Assay #1

DNA encoding epitope-tagged p110 δ (Chantry et al., J. Biol. Chem. 272:19236–19241 (1997)) was transfected into COS cells using DEAE dextran. Three days after transfection, the cells were serum-starved overnight in Dulbecco's modified Eagle's medium plus 0.1% fetal bovine serum. The culture plates were rinsed once with calcium- and magnesium-free phosphate-buffered saline and lysed in 3 mL of buffer R (containing 1% TRITON® X-100, 150 mM NaCl, 10 mM Tris, pH 7.4, 1 mM EDTA, 0.5% NONIDET® P-40, 0.2 mM phenylmethylsulfonyl fluoride, and 1% aprotinin) per confluent 150 mm dish. The p110δ enzyme was immunoprecipitated using an anti-FLAG® monoclonal antibody M2 according to the manufacturer's suggested protocol. The immunoprecipitates were washed three times with buffer R, twice with PAN buffer (containing 10 MM PIPES, pH 7.0, 100 mM NaCl, and 20 µg/mL aprotinin), and resuspended in PAN buffer. Standard kinase reactions used to measure phosphorylation of phosphatidylinositol contained, in 20 µL, 20 mM HEPES-KOH, pH 7.5, 5 mM MnCl$_2$, 0.45 mM EGTA, 10 µM ATP, 0.2 mCi/mL ($\gamma$-$^{32}$P]ATP, 0.2 mg/mL phosphatidylinositol, immunoprecipitated p110δ, and variable amounts of kinase inhibitor. Reactions were started by addition of ATP and stopped by placing aliquots in 100 µL 1M HCl.

Reaction products were extracted with 200 µL CHCl$_3$:MeOH (1:1). The organic phase was extracted with 80 µL 1 M HCl/MeOH (1:1), subsequently dried, resuspended in 8 µL ice cold CHCl$_3$/MeOH (1:1) with 0.1% HCl, and applied to a 1% potassium oxalate-impregnated silica 60 thin layer chromatography plate. Reaction products were resolved by ascending chromatography in CHCl$_3$/MeOH/NH$_4$OH (9:7:2) and visualized by autoradiography. Crude phospholipid standards were run in parallel with the radiolabeled samples and visualized by exposing the plate to iodine vapor. Reactions were quantified by densitometry of autoradiograms using PDQUEST with a pdi 325oe densitometer.

P110 Assay #2

Kinase reactions contained, in 30 µL, 20 mM HEPES-KOH, pH 7.5, 5 mM MnCl$_2$, 0.45 mM EGTA, 32 µM ATP, 0.1 mCi/mL ($\gamma$-$^{32}$P]ATP, 0.2 mg/mL phosphatidylinositol, and purified p 110δ enzyme (described above), and variable amounts of kinase inhibitor molecules. Reactions were started by addition of ATP and stopped by placing aliquots in 100 µL 1N HCl. Reaction products were extracted with 100 µL CHCl$_3$ and phosphorylation of phosphatidylinositol was determined by measurement of radioactivity in the organic phase using a Beckman LS6000IC scintillation counter.

FK506-Rapamycin Associated Protein Kinase (FRAP) Assay

Kinase reactions contained, in 60 µL, 15 mM HEPES-KOH, pH 7.4, 10 mM MnCl$_2$, 80 mM NaCl, 0.3 mg/mL BSA, 2 µM ATP, 0.02 mCi/mL [$\gamma$-$^{32}$P]ATP, 0.2 mg/mL pH-acid stable protein (PHAS) substrate, purified recombinant FRAP kinase (Brown et al., Nature, 369:756–758 (1994)), and variable amounts of kinase inhibitor molecules. Reactions were started by addition of ATP and terminated by adding aliquots to 20 µL 0.9 M phosphoric acid. Reaction cocktails were transferred to P81 paper and washed 5× with at least 250 mL 150 mM phosphoric acid. Phosphorylation of PHAS was determined by measurement of radioactivity bound to P81 paper using a Beckman LS6000IC scintillation counter.

Ataxia Telangiectasia Related (ATR) Protein Kinase Assay

ATR from mouse testes was assayed by antibody capture. Microtiter plates coated with 200 ng mAb 224C (Plug et al., J. Cell Sci. 111:413–423 (1998)) were incubated with 12.5 µg mouse testes extract and incubated at 4° C. for at least 18 h. Plates were washed with kinase buffer (containing 25 mM HEPES-KOH, pH 7.5, 50 mM KCl, 10 mM MgCl$_2$, 2% glycerol, and 1 mM DTT) and incubated with 450 µM myoD peptide (DH-22), 10 µM ATP, and 0.12 mCi/mL [$\gamma$-$^{32}$P]ATP in kinase buffer. Reactions (20 µL) were stopped by addition of 180 µL 150 mM phosphoric acid and aliquots spotted onto P81 paper and washed 5× with at least 2 mL 150 mM phosphoric acid. Scintillation cocktail was added to the dried P81 paper and radioactivity was measured using a Wallac scintillation counter.

Protein Kinase Cθ (PKCθ) Assay

Standard reactions contained, in 30 µL, 20 mM Tris-HCl, pH 7.5, 20 mM MgCl$_2$, 1 mM CaCl$_2$, PMA, PS, 0.3% TRITON® X-100, 70 µM ATP, 0.1 mCi/mL [$\gamma$-$^{32}$P]ATP, 60 µM myelin basic protein (MBP) peptide (residues 4 through 14), purified recombinant PKCO (Baier et al., J. Biol.Chem. 268:4997–5004 (1993)) and variable amounts of kinase inhibitor. Reactions were started by addition of ATP and terminated by adding 5% phosphoric acid. Reactions were transferred to P81 paper and the paper was washed 5× with at least 250 mL 150 mM phosphoric acid. Phosphorylation of MBP was determined by measurement of radioactivity bound to P81 paper using a Beckman LS6000IC.

Casein Kinase I (CKI) Assay

Standard 20 µL reactions contained 150 mM NaCl, 50 mM Tris-HCl, pH 7.5, 10 mM MgCl$_2$, 100 µM ATP, 0.1 mCi/mL [$\gamma$-$^{32}$P]ATP, 2.8 µg casein, and 100 ng purified recombinant CKI (Knippschild, Oncogene 15:1727–1736 (1997)). Reactions were started by addition of ATP and stopped by application to P81 paper. Reaction products spotted onto P81 paper were washed five times with a total volume of at least 250 mL 150 mM phosphoric acid, dried, and radioactivity determined in a Beckman LS6000IC scintillation counter.

Calcium/Calmodulin Kinase II (CaMKII) Assay

Standard 20 µL reactions contained 50 mM HEPES-KOH, pH 7.5, 5 mM MgCl$_2$, 1 mM CaCl$_2$, 30 µg/mL calmodulin, 200 µM CaMKII peptide substrate (Calbiochem, La Jolla, Calif.), 50 µM ATP, 1 mCi/mL [$\gamma$-$^{32}$P]ATP, CaMKII (Calbiochem, La Jolla, Calif.) and variable amounts of kinase inhibitors. Reactions were started by addition of ATP and terminated by adding aliquots to 10% acetic acid. Reactions were transferred to P81 paper and washed 5× with greater than 250 mL 10% acetic acid. Phosphorylation of CaMKII peptide was determined by measurement of radioactivity bound to P81 paper using a Beckman LS6000IC scintillation counter.

EXAMPLE 5

Cellular Toxicity Determination

In order to assess toxicity of the DNA-PK inhibitors identified, each inhibitor was first incubated with cells in culture and cell viability monitored.

A large panel of cultured human tumor cell lines (see Table 4) ACHN, 786-0, HCT116, SW620, SK-MEL5, SK-MEL28, A549, H322, OVCAR3, SK-OV3, MCF7, MDA-MB231, MOLT4, HL60, SNB19, PC3) and the normal human fibroblast cell line MRC5 were treated with 2-hydroxy-4-morpholin-4-yl-benzaldehyde and 1-(2-hydroxy-4-morpholin-4-yl-phenyl)-ethanone at concentrations up to 200 µM.

TABLE 4

CULTURED HUMAN CELL LINES ASSAYED

| CELL LINE | CELL TYPE | ATCC DESIGNATION |
|---|---|---|
| ACHN | Human renal adenocarcinoma | CRL-1611 |
| 786-O | Human renal cell adenocarcinoma | CRL-1932 |
| HCT 116 | Human colorectal carcinoma | CCL-247 |
| SW620 | Human colorectal adenocarcinoma | CCL-227 |
| SK-MEL-5 | Human malignant melanoma | HTB-70 |
| SK-MEL-28 | Human malignant melanoma | HTB-72 |
| A549 | Human lung carcinoma | CCL-185 |
| NCI-H322 | Human nonsmall cell lung carcinoma | CRL-5806 |
| OVCAR-3 | Human ovary carcinoma | HTB-161 |
| SK-OV-3 | Human ovary carcinoma | HTB-77 |
| MCF-7 | Human mammary gland adenocarcinoma | HTB-22 |
| MDA-MB-231 | Human mammary gland adenocarcinoma | HTB-26 |
| MOLT-4 | Human acute lymphoblastic leukemia | CRL-1582 |
| HL-60 | Human acute promyelocytic leukemia | CCL-240 |
| SNB-19 | Central nervous system | |
| PC-3 | Human prostate adenocarcinoma | CRL-1435 |

Cultured cells were distributed on 96-well microtiter plates and allowed to adhere for at least 16 h. Cells were treated with 200 µM (2-hydroxy-4-morpholin-4-yl-benzaldehyde or 1-(2-hydroxy-4-morpholin-4-yl-phenyl)-ethanone continuously for 48 h. Cells were then analyzed using the MTS assay, CELLTITER™ cell proliferation assay kit (Promega, Madison, Wis.) according to the manufacturer's recommended protocol.

Using the MTS dye metabolism assay, no evidence of killing of any of these cell lines was observed.

Cell viability was also tested during drug treatment using the trypan blue exclusion assay. Freshly cultured thymocytes from BALB/c and BALB/c p53-/p53- mice were incubated in RPMI 1640 media (Gibco) containing 20% FBS, 1 mM sodium pyruvate, 2 mM L-glutamine, 100 U/mL penicillin and 100 µg/mL streptomycin at 37° C. with 5% $CO_2$ in a humidified incubator. At the time of preparation, $p53^+/p53^+$ and $p53^-/p53^-$ thymocytes exhibited 96% and 89% viability, respectively, measured by vital dye staining (trypan blue). Cultured cells were incubated in the presence of varying concentrations of 2-hydroxy-4-morpholin-4-yl-benzaldehyde up to 32 µM. Cultured human and mouse cell lines were incubated in RPMI 1640 media containing 10% FBS, 100 U/mL penicillin and 100 µg/mL streptomycin at 37° C. with 5% $CO_2$ in a humidified incubator with 2-hydroxy-4-morpholin-4-yl-benzaldehyde for several days. Tumor cell lines, HL60, Jurkat, JY and B16/F10 and the normal cell line WS1 were tested using this assay when incubated at drug concentrations up to 25 µM.

In no instances were cells sensitive to killing by 2-hydroxy-4-morpholin-4-yl-benzaldehyde as determined by the trypan blue exclusion method.

The lack of chemical cytotoxicity of these DNA-PK inhibitors was consistent with the high viability of cells cultured from scid mutant mice and showed no indication that essential cellular functions are nonspecifically targeted by either 2-hydroxy-4-morpholin-4-yl-benzaldehyde or 1-(2-hydroxy-4-morpholin-4-yl-phenyl)-ethanone.

EXAMPLE 6

(a) V(D)J Recombination Assay

Because scid mutant mice are unable to perform V(D)J recombination, assays were designed to assess whether the class of DNA-PK inhibitors could also disrupt the process in vitro.

Recombination assays were performed as previously described (Leu et al., *Mol. Cell. Biol* 15:5657–5670 (1995)). DR3 cells were grown to a density of approximately 0.5 to $0.8 \times 10^5$ cells/mL in RPMI 1640 containing 10% dialyzed FBS, L-glutamine, 100 U/mL penicillin and 100 µg/mL streptomycin, 50 µM β-mercaptoethanol, and 10 µM methotrexate at 37° C. with 5% $CO_2$ in a humidified incubator. Cells were concentrated and washed in HBS (containing 30 mM HEPES-KOH, pH 7.5, 140 mM NaCl, and 5 mM KCl) and resuspended in HBS at a density of $2.0 \times 10^8$ cells/mL. Cells ($1.0 \times 10^7$) were transiently transfected by electroporation with 10 µg of the recombination substrate pJH200 (Leu et al., *Mol. Cell. Biol.* 15:5657–5670 (1995)) and transferred to a 90 mm cell culture dish containing 8 mL media with or without 2-hydroxy-4-morpholin-4-yl-benzaldehyde as described above. After 2 days, cells were removed from the dish with a rubber policeman, concentrated, washed one time with PBS, and resuspended in 0.1 mL lysis buffer (0.3% Triton X-100, 50 mM Tris-HCl, pH 7.5, 50 mM EDTA). Following a five min incubation at room temperature, cellular debris was removed by centrifugation at 12,000 rpm for two min in a microfuge. The supernatant was extracted sequentially with phenol and chloroform/isoamyl acetate (24:1), after which, one tenth volume 3 M sodium acetate and 2 volumes cold 100% ethanol were added to the aqueous phase. Precipitated nucleic acid was collected by centrifugation at 12,000 rpm for 15 min and suspended in 25 µL water. An aliquot of the material was used to transform DH5α cells by electroporation. Cells were plated on LB media containing either carbenicillin (carb) or carbenicillin and chloramphenicol (cm). Recombination was defined as the ratio of colonies resistant to both carbenicilin and chloramphenicol ($carb^r cm^r$) to colonies resistant to carbenicilin ($carb^r$).

Results indicated that V(D)J recombination was inhibited when cultured mouse B-lymphocytes, competent to rearrange immunoglobulin recombination signal-coding sequences present on autonomously replicating plasmids, were treated with 2-hydroxy-4-morpholin-4-yl-benzaldehyde DNA rearrangement was inhibited 8-fold at 50 µM 2-hydroxy-4-morpholin-4-yl-benzaldehyde indicating that DNA-PK participates in V(D)J recombination in vitro and that this drug is capable of inhibiting intracellular DNA-PK.

(b) DNA Double-strand Break Repair Assay

To further determine the cellular effect of DNA-PK inhibitors, an assay to measure chromosomal discontinuities was employed. Ionizing radiation induces chromosomal DNA double-strand breaks. Following high dose radiation, chromosomes can be extracted from cells and fractionated by pulse field electrophoresis to distinguish chromosomal fragments from intact larger chromosomes. Using this technique, the activity of DNA-PK inhibitors was measured.

MDA-MB231 (human breast carcinoma) cells were seeded onto T25 flasks with RPMI1640+10% FBS, 2 mM L-glutamine, penicillin G 100 U/ml-streptomycin sulfate 10µg/ml, 1 mM Na pyruvate. When confluent, media was removed and replaced with media containing DNA-PK inhibitor or vehicle. Cells were incubated at 37° C. for 1 hr in a humidified chamber with 5% $CO_2$. Media then was removed and flasks were filled with ice-cold D-PBS and either: (a) processed immediately; (b) irradiated (25 Gy in a $^{137}Cs$ Mark I irradiator at a flux of 335 rad/min) and processed immediately; (c) irradiated and incubated for 2 hr in complete RPMI1640+vehicle at 37° C. (in humidified 5% $CO_2$ atmosphere to allow for DNA repair), or (d) irradiated and incubated for 2 hr in complete RPMI1640+DNA-PK inhibitor compound. To process cells, D-PBS or media was replaced with 5 ml ice-cold D-PBS and cells were removed from flasks, concentrated with cell resuspension buffer (10 mM Tris pH 7.2, 50 mM EDTA) and added to warm 2% clean cut agarose (Bio-Rad # 170-3594). Cell slurries were embedded in agarose, then incubated in PK buffer (10 mM Tris pH 8.0, 100 mM EDTA, 1% lauryl sarcosine, 0.2% Na deoxycolate, 100 µg/ml Proteinase K (Bio-Rad #732-6348)) at 4° C. for 2 min, followed by incubation at 50° C. overnight. Cells embedded in agarose plugs were washed with buffer containing 10 mM Tris pH 8.0, 50 mM EDTA for 15 min. Agarose plugs then were treated with 50 µg/ml RNase (DNase free; Boehringer#1579-681) at 37° C. for 1 hr. An agarose gel (1% low melt agarose; Bio-Rad #162-0017) then was cast around plugs in 0.5×TBE and chromosomal DNA was fractionated by pulse field gel electrophoresis at 99V (2V/cm), 45sec pulse time, 48 hr with 14° C. recirculating 0.5×TBE in a CHEF-DR II cell apparatus (Bio-Rad). Chromosomal DNA was visualized with SYBR-Gold (Molecular probes # S-11494) and the fluorescent image quantified on the STORM 860 (Molecular Dynamics).

Using this technique, it was found that concentrations of 1-(2-hydroxy-4-morpholin-4-yl-phenyl)-ethanone which enhanced radiation induced cell killing (measured by the DNA synthesis assay) also inhibited DNA double-strand break repair. These data demonstrate that DNA-PK inhibitors perturb chromosomal DNA double-strand break repair, and suggests that inhibition of this DNA repair reaction is responsible for the potentiation of radiation toxicity. Furthermore, these data suggest that DNA-PK inhibitors bind the target in the nucleus ultimately inducing sensitivity to chemical and physical agents that yield DNA dsbs.

(c) Animal Tumor Model: Pro-drug

To increase the solubility and achieve higher plasma drug concentrations, the activity of a phoshorylated derivative of 1-(2-hydroxy-4-morpholin-4-yl-phenyl)-ethanone, i.e., Example 34-p, was tested. Mouse pharmacokinetic analysis of Example 34-p demonstrated that it is rapidly converted to parent compound (Example 34) in plasma. Example 34-p then was tested for anti-tumor activity.

HCT116 cells (human colon carcinoma) or MDA-MB-231 (human breast carcinoma) were used to propagate xenograft tumors in 6–8 week old female athymic BALB/c (nu/nu) mice. Mice were maintained in a laminar airflow cabinet under pathogen-free conditions and fed sterile food and water ad libitum. Human cells were grown to subconfluence in RMPI1640 supplemented with 10% FBS, 100 U/ml penicillin, 100 µg/mL streptomycin and 1.5 mM L-glumtamine in a 5% humidified environment. Single cell suspensions were prepared in CMF-PBS and cell concentrations adjusted to $4 \times 10^7$ cells/mL. Mice were inoculated subcutaneously on the right proximal leg with $4 \times 10^6$ cells.

Mice were randomized (10 mice/group) into three groups with mean tumor volumes ca. 100 mg. Mice then were either mock treated (drug vehicle only), irradiated only (150 rad), or received both ionizing radiation and drug (150 rad+32 mg Example 34-p). Example 34-p was prepared in 25% CREMOPHORO®: 75% normal saline at a concentration of 80 mg/ml. Dosing was modeled to obtain plasma levels of >9,000 ng/ml for approximately 5 hr. Animals were dosed with 100 µl of drug solution (400 mg/kg) and irradiated on the tumor bearing leg using a Mark I $^{137}Ce$ irradiator approximately 20 minutes after the initial bolus drug administration. Animals subsequently were dosed every hour for a total of 4 hrs. This dosing regimen, 4×400 mg/kg with one dose of 150 rad per day was repeated once (HCT116 tumors) or twice (MDA-MB231) for a total of two or three treatment days, respectively. Animals were weighed and tumors were measured every other day for the duration of the experiment. Mice were sacrificed when the tumor volume reached 1200 mg or approximately 7% of body weight.

Animals treated with Example 34-p and radiation showed a significant (p=0.0414; HCT116 experiment) delay in tumor growth rate compared to animals treated with vehicle or radiation only. The time required for the drug and radiation treated animals to reach 50% survival was about 2 weeks longer than for the study group receiving radiation only. These data demonstrate the utility of making and delivering pro-drugs of this class of DNA-PK inhibitor compounds. These data also show that Example 34-p has anti-tumor activity in two different human (colon, breast)-mouse xenograft assays and may be generally applicable to a wide range of human tumor types and cancer disease indications.

EXAMPLE 7

Chemosensitization

To test the hypothesis that inhibition of DNA-PK can potentiate the killing effect of cellular treatment that induces DNA dsbs, cells were incubated in the presence of both selective DNA-PK inhibitors and chemical DNA damaging agents.

Cells plated at a density of 5,000 to 20,000 per well in 96-well microtiter plates were grown in RMPI 1640 containing 10% FBS, 100 U/mL penicillin and 100 µg/mL streptomycin, for 18 h at 37° C. in a humidified incubator with 5% $CO_2$. Cells tested included ACHN, 786-0, HCT-116, SW620, SK-MEL-5, SK-MEL-28, A549, H322, OVCAR-3, SK-OV-3, MCF-7, MDA-MB-231, MOLT4, HL60, SNB-19, PC-3. Cells were treated with media containing chemotherapeutic drugs alone or with media containing chemotherapeutic drugs and a DNA-PK inhibitor of the invention, 1-(2-hydroxy-4-morpholin-4-yl-phenyl)-ethanone. Cells were incubated for two days before growth was measured using a tetrazolium dye assay (MTS). Chemotherapeutic drugs included bleomycin etoposide, vinblastine, doxorubicin, paclitaxel, cisplatin, chlorambucil, cyclophosphamide, 5-fluorouracil, cytosine-arabinoside, 6-mercaptoguanine and methotrexate (all purchased from Sigma). The drug concentration necessary to inhibit cell growth to 50% of untreated control cells was defined as the $GI_{50}$.

Results indicated that 1-(2-hydroxy-4-morpholin-4-yl-phenyl)-ethanone enhanced growth inhibition of the human colon carcinoma cell line HCT116 when incubated with bleomycin etoposide and chlorambucil (agents known to induce DNA dsbs). The $GI_{50}$ (bleomycin) was reduced 7-fold in the presence of 100 μM 1-(2-hydroxy-4-morpholin-4-yl-phenyl)-ethanone from $2 \times 10^{-1}$ units/mL to $3 \times 10^{-2}$ units/mL. The etoposide $GI_{50}$ was reduced 10-fold from $1.2 \times 10^{-4}$ M to $1.4 \times 10^{-5}$ M. The chlorambucil $GI_{50}$ was also reduced 10-fold from $1.2 \times 10^{-4}$ M to $1.4 \times 10^{-5}$ M. The chorambucil $GI_{50}$ was also reduced 10-fold from $1.2 \times 10^{-4}$ M to $1.4 \times 10^{-5}$ M. Therefore, 1-(2-hydroxy-4-morpholin-4-yl-phenyl)-ethanone potentiated the growth inhibitory effect of these three DNA damaging agents.

The inhibitor 1-(2-hydroxy-4-morpholin-4-yl-phenyl)-ethanone did not potentiate the growth inhibitory effects of chemotherapeutic agents that do not induce DNA dsbs, such as vinblastine, doxorubicin, paclitaxel, cisplatin, cyclophosphamide, 5-fluorouracil, cytosine-arabinoside, 6-mercaptoguanine and methotrexate.

EXAMPLE 8

Chemo/Radiosensitization: Colony Forming Assay

In order to assess the ability of the DNA-PK inhibitors to potentiate the effect of radiation treatment on cancer cells, the following assay was carried out.

Colon carcinoma cells (HCT116) plated in RPMI-1640 containing 10% dialyzed FBS, L-glutamine, 100 U/mL penicillin and 100 μg/mL streptomycin with or without 200 μM 2-hydroxy-4-morpholin-4-yl-benzaldehyde or 1-(2-hydroxy-4-morpholin-4-yl-phenyl)-ethanone were treated with increasing amounts of γ-radiation up to 1600 rad. Alternatively, cells were incubated with or without 1-(2-hydroxy-4-morpholin-4-yl-phenyl)-ethanone and increasing amount of etoposide up to 100 μM for 24 h, at which time the drug was removed and cells were incubated in fresh media without drug. After approximately one week, colonies were scored. Culture media was removed and cells were fixed with a solution of methanol/acetic acid (3:1 v/v). Following fixation, PBS was added and colonies were visualized by staining with crystal violet (50 μg/mL final concentration). Colonies were defined as cellular masses 25 to 40 cells in diameter and were estimated to be made up of 500 to 1500 cells.

In addition to the 48 h growth assay, the effect of DNA-PK inhibitors on long term cellular growth was tested following treatment that induced DNA double-strand breaks. Continued cell division of adherent cells in culture results in the formation of a colony. Colony formation is the balance of growth and cell division with cell death by apoptosis, necrosis, or senescence. Because the clonogenic survival assay measures a cell's ability to sustain growth and cell division, it provides a more accurate representation of the effect of drug treatment on cellular proliferation.

Using the clonogenic assay, it was observed that both 2-hydroxy-4-morpholin-4-yl-benzaldehyde and 1-(2-hydroxy-4-morpholin-4-yl-phenyl)-ethanone increased the sensitivity of the HCT116 cell line to killing by γ-radiation. The radiation dosage which kills 50% of the cells ($LD_{50}$) for cells incubated in the presence of 1-(2-hydroxy-4-morpholin-4-yl-phenyl)-ethanone was 4-fold lower than when incubated in the absence of drug, i.e., 35 rad and 150 rad, respectively. Drug alone had no effect on cell division. Likewise, a radiation dose that kills 90% of the cells ($LD_{90}$) also was 4-fold lower when cells were treated with drug than without, i.e., 100 rad and 410 rad, respectively.

An alternative metric by which to characterize the cellular sensitivity to radiation is the slope, $D_0$, of the survival curve during the exponential phase of cell killing (*Radiobiology for the Radiologist*, Fourth Edition, Hall (ed), J.B. Lippincott Co, Philadelphia, 1994; pp. 37–38). More precisely, this measurement indicates the radiation dose required to reduce cell survival $e^{-1}$. By this method, 1-(2-hydroxy-4-morpholin-4-yl-phenyl)-ethanone reduced $D_0$ by one third, from 150 rad to 50 rad. These data clearly demonstrated that this class of DNA-PK inhibitors radiosensitive tumor cells.

These results were in agreement with experiments performed with scid cell lines and leukocytes cultured from wild-type and scid mice. Others (Fulop et al., *Nature* 347: 479–482 (1990)) have demonstrated that scid cells are 2.4-fold more radiosensitive than normal cells as measured by granulocyte-macrophage colony forming units (CFU-GM). Similarly, others (Hendrickson et al., *Proc. Natl. Acad. Sci. USA.*, 88:4061–4065 (1991)) have observed that cultured scid fibroblasts were 2.9-fold more sensitive than normal mouse fibroblasts. In light of these observations, these data strongly suggest that these compounds radiosensitized tumor cells by disrupting DNA dsbs repair as a result of subcellular inhibition of DNA-PK.

To further confirm that inhibition of DNA dsbs repair by this class of DNA-PK enzyme inhibitors enhances tumor cell killing, assays were designed to determine if the inhibitor compounds could sensitize cells to killing by etoposide, a chemical agent that induces DNA dsbs. In experiments set up essentially as described above, it was observed that, as with radiation, the cytotoxicity of etoposide was potentiated by 1-(2-hydroxy-4-morpholin-4-yl-phenyl-ethanone. The $LD_{50}$ of etoposide with and without 1-(2-hydroxy-4-morpholin-4-yl-phenyl)-ethanone was 0.075 μM and 1.1 μM, respectively; a 15-fold enhancement. The $LD_{90}$ was enhanced 3-fold by 1-(2-hydroxy-4-morpholin-4-yl-phenyl)-ethanone, 0.9 μM versus 2.9 μM. This class of DNA-PK inhibitors therefore enhanced cytotoxicity of DNA double-strand breaks induced by both physical and chemical DNA damaging agents.

EXAMPLE 9

Radiosensitization: DNA Synthesis Assay

In order to assess the ability of a representative DNA-PK inhibitor to potentiate the toxic effect of radiation treatment on a large number of cancer cells, the following assay was performed.

Cell lines represented in Table 4 were used to inoculate 96 well microtitre plates at a density of $5 \times 10^3$ cells/mL in RPMI 1640 containing 10% FBS, 100 U/mL penicillin and 100 μg/mL streptomycin. Cells were incubated with or without 1-(2-hydroxy-4-morpholin-4-yl-phenyl)-ethanone at concentrations ranging from 15–125 μM and treated with γ-radiation at doses up to 800 rads. Cells were incubated in a humidified chamber at 37° C. in 5% $CO_2$ for five days. After four days, cells were pulsed with [$^3$H]-thymidine. On day five, cells were harvested and cellular radioactivity determined.

All cell lines exhibited a γ-radiation dose-dependent decrease in the absolute amount of [$^3$H]-thymidine incorporated into cellular DNA. [$^3$H]-thymidine incorporation was further reduced by incubation with the 1-(2-hydroxy-4-morpholin-4-yl-phenyl)-ethanone DNA-PK inhibitor in a dose-dependent manner, with the drug-dependent decrease in DNA synthesis induced by γ-radiation ranging from 1.8- to 4-fold. The effect of 1-(2-hydroxy-4-morpholin-4-yl-phenyl)-ethanone (as a representative of this class of DNA-PK inhibitors) enhanced the toxic effect of γ-radiation on all tumor cells described in Table 4.

This data corroborated the previous observations in the colony forming assay (Example 8), showing that inhibition of DNA-PK sensitizes tumor cells to treatments that induce cellular DNA double-strand break damage. Furthermore, these results indicated that the DNA-PK inhibitors of the invention are applicable to treatment of a wide range of tumors from major organ systems.

EXAMPLE 10

Animal Tumor Models

In order to determine if the results obtained above could be extended to in vivo conditions, an animal model was designed using human tumor cell xenografts.

HCT116 cells (human colon carcinoma) were used to propagate xenograft tumors in 6–8 week old female athymic BALB/c (nu/nu) mice. Mice were maintained in a laminar airflow cabinet under pathogen-free conditions and fed sterile food and water ad libitum. HCT116 cells were grown to subconfluence in McCoy's media supplemented with 10% FBS, 100 U/mL penicillin, 100 µg/mL streptomycin, and 1.5 mM L-glutamine in a 5% $CO_2$ humidified environment. Single cell suspensions were prepared in CMF-PBS (0.9 mM KCl, 2.7 mM $KH_2PO_4$, 13.8 mM NaCl, pH 7.5), and cell concentration adjusted to $4\times10^7$ cells/mL. Mice were inoculated subcutaneously (s.c.) on the right flank or right leg with a total of $4\times10^6$ cells (100 µL).

Mice were randomized (5 mice/group) into four treatment groups and used when tumors reached a weight of 75 to 100 mg (usually 7 to 11 days post-inoculation). Tumors were measured with vernier calipers and tumor weights were estimated using the empirically-derived formula below.

Tumor weight (mg)=tumor length (mm)×tumor width (mm)$^2$/3.3.

Treatment consisted of i) 100 µL s.c. injection of vehicle alone (1:3, CREMOPHOR® (BASF) EL:D-PBS, 0.9 mM $CaCl_2$, 0.5 mM $MgCl_2$, 0.9 mM KCl, 2.7 mM $KH_2PO_4$, 13.8 mM NaCl.); ii) 100 µL 8 mg/mL 2-hydroxy-4-morpholin-4-yl-benzaldehyde in vehicle (approximately 40 mg/kg); iii) vehicle plus 2.5 Gy γ-irradiation 30 min post-injection; or iv) 100 µL 8 mg/mL 2-hydroxy-4-morpholin-4-yl-benzaldehyde in vehicle (approximately 40 mg/kg) plus 2.5 Gy γ-radiation 30 min later. All injections were performed s.c. in the vicinity of the tumor. Radiation was delivered with a using a $^{137}$Ce source. Treatments were repeated daily for 1 to 5 consecutive days. Tumor size was monitored every other day for the duration of the experiment.

Based on previous results, it was expected that tumor cell killing would be most effective if DNA repair and signaling were disrupted at the time of DNA damage induction. Pharmacokinetic analysis of two DNA-PK inhibitors, 2-hydroxy-4-morpholin-4-yl-benzaldehyde and 1-(2-hydroxy-4-morpholin-4-yl-phenyl)-ethanone, indicated that the maximum plasma concentration for each was achieved at approximately 15 to 30 min after administration and remained high for about one hour following subcutaneous administration. The protocol therefore was designed whereby mice were irradiated within 40 min following drug administration so that plasma drug concentration would be near its zenith during radiation treatment.

Preliminary experiments indicated that 2-hydroxy-4-morpholin-4-yl-benzaldehyde enhanced the tumoristatic effect of total body irradiation. In experiments where animals were given 100–500 rad γ-radiation, 2-hydroxy-4-morpholin-4-yl-benzaldehyde delayed tumor growth 1.2- to 1.8-fold relative to animals that received radiation only. When larger doses of radiation were delivered, 2-hydroxy-4-morpholin-4-yl-benzaldehyde treatment had a tumoricidal effect. In an experiment where animals with an average tumor burden of 500 mg were treated with drug and 300 rad once daily for two days, tumors shrank greater than 10-fold. In contrast, irradiated animals receiving the same radiation treatment without drug demonstrated no decrease in tumor size although the rate of tumor regrowth was retarded.

Treatment with 1-(2-hydroxy-4-morpholin-4-yl-phenyl)-ethanone also potentiated the effect of radiation on tumors. Mice receiving 250 rad plus drug once daily for five consecutive days exhibited no increase in tumor growth whereas tumors in mice receiving radiation alone increased at a rate of 7 mg per day.

These data demonstrated that the DNA-PK inhibitors potentiate the killing effect of radiation on tumors by increasing their radioresponsiveness. The inhibitors, therefore, act synergistically with radiation.

EXAMPLE 11

Use of DNA-PK Inhibitors in the Treatment of Human Disease

The observations described herein indicated that the DNA-PK inhibitors have broad applications in the treatment of proliferative disorders, including cancer. In particular, the inhibitors potentiate the therapeutic effects of radiation during the treatment of human cancers and can be used in combination with chemotherapy and several forms of radiation treatments including, teletherapy (i.e., radiation therapy administered from a source at a distance from the body), radioimmunotherapy, and brachytherapy (i.e., radiation therapy wherein the irradiation source is close to or within the body). The radiation can be administered by stereotactic radiosurgery or fractionated microbeam teletherapy.

During teletherapy, drug administration prior to radiation treatment, as was carried out in the animal experiments described above, is most effective in reducing tumor mass. In this method, the drug is administered systemically and radiation is focused locally to the tumor site. Circumstances also can exist wherein it is advantageous to administer the DNA-PK inhibitor following radiation treatment. In either treatment, the drug can be delivered by any of a number of routes described herein. Potentiation of the efficacy of teletherapy can be applied to radiocurative tumors as well as radiorefractory tumors. Seminoma, a carcinoma of the cervix, larynx, breast and prostate, Hodgkin's disease, and acute lymphocytic leukemia are examples of radiocurative tumors for which this class of DNA-PK inhibitors improve treatment by achieving greater therapeutic effect and reducing collateral tissue toxicity. Combination therapy using the drug with teletherapy also has the effect of enhancing the radioresponsiveness of radioresistant tumors; some examples include as glioblastomas, osteogenic sarcomas, retinoblastomas, astrocytomas, and some head and neck cancers. It is anticipated that inhibition of DNA-PK activity can be of therapeutic benefit in all instances where radiation is used with curative intent.

Radiation therapy also is indicated for pain management during cancer treatment. Palliation of pain is an important component of some treatment strategies. It is contemplated that the procedure of radiation with palliative intent also is enhanced by inhibition of DNA-PK in tumor and possible normal tissue, e.g., administration of bone-localizing isotopes, such as Sn-117, for the treatment of bone pain associated with bone cancer.

The DNA-PK inhibitors of the invention also are effective in combination with radioimmunotherapy and brachytherapy. The goal in these therapies is to deliver radiation internally to tumor sites in an attempt to minimize damage to surrounding normal tissue, radioactive seed implants for prostate cancer. The DNA-PK inhibitors can be used to enhance the therapeutic index of these radiation treatments also.

DNA-PK inhibitors of the invention also can be used to potentiate the benefits of chemotherapy. Combination treatment with chemotherapeutic agents that induce DNA damage and a DNA-PK inhibitor induces a synergistic effect on tumor tissue as observed in experiments using etoposide, bleomycin, and chlorambucil with cultured human tumor cells. These data indicate that treatment regimens employing topoisomerase inhibitors, alkylating agents, and/or bleomycin are enhanced by this class of DNA-PK inhibitor. Other chemical agents used in the treatment of cancer can also be made more effective by inhibition of DNA-PK.

Therapeutic benefit also can be obtained through the administration of a DNA-PK inhibitor conjugated to an antibody. Drug delivery can be targeted to specific sites within the body as a function of the determinants of antibody recognition. This method of administration can be combined with radiation or chemotherapy. It is expected that DNA-PK inhibitor drugs can be coadministered with chemotherapeutic drugs which themselves are linked to tumor-specific antibodies.

It also is expected that DNA-PK inhibitors can be used in combination with nongenotoxic modulators of the cell division cycle with or without genotoxic treatments, such as radiation and chemotherapy described above. Such nongenotoxic treatments are anticipated to perturb cell cycle metabolism, affecting the temporal order and kinetics of cell cycle events such as initiation of the cell cycle, DNA replication, centrosome duplication, chromosome segregation and cytokinesis. The execution of these cell cycle events is integrated with events related to DNA damage repair. Therefore, the combined effect of disrupting the coordinated repair of DNA damage with cell cycle progression is expected to reduce the fidelity of the cell division cycle with lethal consequences.

Because many anti-cancer drugs are also immunosuppressive, the DNA-PK inhibitors also can be used to potentiate the efficacy of drugs in the treatment of inflammatory diseases. Examples of some diseases that can benefit from combination therapy with the inhibitors are rheumatoid arthritis, psoriasis, vitiligo, Wegener's granulomatosis, and systemic lupus erythematosus (SLE). A common theme in the treatment of arthritis, Wegener's granulomatosis, and SLE is the use of immunosuppressive therapies such as ionizing radiation, methotrexate, and cyclophosphamide. As these treatments induce, DNA damage, either directly or indirectly, inhibition of DNA-PK activity within offending immune cells will render the cells more sensitive to control by these standard treatments. Psoriasis and vitiligo are commonly treated with ultraviolet radiation (UV) in combination with psoralens. These two DNA damaging agents induce T cell killing thought to be responsible for this disease. Ihibition of DNA-PK enhances the killing effect of UV radiation and psoralens, and increases the therapeutic index of the treatment regimen. In general, the DNA-PK inhibitors can potentiate the control of inflammatory disease cells in combination with currently used immunosuppressive drugs.

Recently, it has been demonstrated that cells cultured from scid mice are refractory to retrovirus infection (Daniel et al., Science, 284: 644–647 (1999)) due to the deficiency in DNA-PK. This class of DNA-PK inhibitors therefore can be used to protect cells from retroviral infection. These inhibitors can have therapeutic benefit in the treatment of acquired immune deficiency syndrome (AIDS) by blocking HIV infection of T-cells. In this example, this class of inhibitors can have significant activity as a single agent or coadministered with other antiviral agents, such as protease inhibitors; transcriptase inhibitors, nucleoside analogs, and the like.

To the degree that DNA-PK participates in retroviral infection, inhibitors of the invention can be used in therapeutic intervention. The RNA genome of retroviruses is copied into DNA which integrates into the genome of an infected cell. Integration necessarily requires introduction of dsbs in the host cell genome, and observations suggest a role for DNA-PK is repairing the break (Daniel et al., Science, 284:644–647 (1999)). Inhibition of DNA-PK therefore arrests cell growth and signal apoptosis of the infected cell.

Preliminary results using retrovirus-infected Jurkat J77 cells indicated that apoptosis increased 1.5- to 2-fold in cells treated with a DNA-PK inhibitor compared to cells that were not treated.

The inhibitors of the invention also can be effective during marrow ablation prior to bone marrow transplantation. Bone marrow conditioning is currently performed by treatment with cytotoxic agents such as ionizing radiation, cyclophosphamide, and/or busulfan. The goal of the procedure is to remove existing marrow cells and provide space for transplanted stem cells to take residence. The inhibitors therefore can potentiate the cytotoxic effect of current treatments by allowing more effective bone marrow conditioning with less toxic side effects.

EXAMPLES 12–149

Description of DNA-PK inhibitors

Compounds structurally related to the DNA-PK-specific inhibitors mentioned above also were tested for kinase inhibitory activity as described above. Synthesis and physical properties of these inhibitors are set out below.

EXAMPLE 12

5-Morpholin-4-yl-2-nitro-phenylamine

A solution of 5-chloro-2-nitrophenylamine (4.3 g, 25 mmol) and morpholine (4.4 mL, 500 mmol) in dimethylsulfoxide (DMSO) (25 mL) was stirred at 90° C. for 16 h. The reaction mixture was poured into water (500 mL) and the resulting precipitate was collected by vacuum filtration and recrystallized from methanol (300 mL) to yield the product as orange crystals (2.4 g, 43%). M.P. 177–178° C. (lit. 184–186° C.). See, *Polymers* 36:3401–3408 (1995).

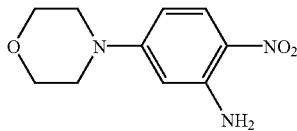

$^1$H NMR (90 MHz, CDCl$_3$) δ 8.02 (d, J=9.2 Hz, 1 H), 6.32–6.09 (m, 4 H), 3.82 (t, J=5.0 Hz, 4 H), 3.29 (t, J=5.0 Hz, 4 H). LRMS: 223 (M$^+$).

EXAMPLE 13

5-(4-Methyl-piperazin-1-yl)-2-nitro-phenylamine

A mixture of 5-chloro-2-nitrophenylamine (2.5 g, 14 mmol), 1-methylpiperizine (3.2 mL, 30 mmol), and potassium carbonate (K$_2$CO$_3$) (2.0 g, 14 mmol) in dimethylformamide (DMF) (20 mL) was stirred at 120° C. for 18 h. The reaction mixture was cooled to room temperature and poured into water (150 mL). The precipitated crude product was collected by filtration, dried in vacuo, and purified by recrystallization from ethyl acetate (EtOAc) (75 mL) to yield yellow-green crystals (1.8 g, 54%). See, *J. Med. Chem.*, 39:997 (1996).

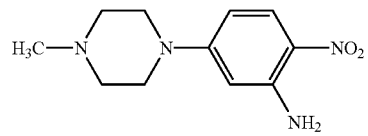

$^1$H NMR (90 MHz, CDCl$_3$) δ 8.00 (d, J =9.9 Hz, 1 H), 6.33–6.15 (m, 3 H), 5.94 (d, J=2.6 Hz, 1 H), 3.37 (t, J=5.3 Hz, 4 H), 2.51 (t, J=5.3 Hz, 4 H), 2.33 (s, 3 H).

EXAMPLE 14

2-Hydroxymethyl-5-morpholin-4-yl-phenol

A solution of sodium borohydride (NaBH$_4$) (0.66 g, 17 mmol) in water (25 mL) was treated with 4-morpholinyl-salicylaldehyde (1.8 g, 9 mmol) in small portions over 30 min and stirred at room temperature for 3 h. The reaction was quenched with acetone (5.1 mL, 100 mmol), acidified to pH 7 with 7.8 mL of 5% hydrochloric acid (aqueous) and extracted with chloroform (CHCl$_3$) (2×100 mL). The combined CHCl$_3$ extracts were dried over sodium sulfate (Na$_2$SO$_4$) and concentrated in vacuo to yield 0.7 g of pale yellow solid which was purified by trituration with 60/40 CHCl$_3$/ethyl acetate (EtOAc) to yield the product as a white solid (0.25 g).

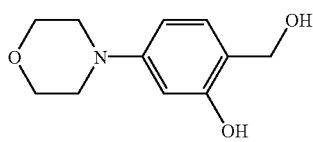

$^1$H NMR (90 MHz, CDCl$_3$) δ 6.90 (d, J=8.0 Hz, 1 H), 6.43–6.34 (m, 2 H), 4.77 (s, 3 H), 3.82 (t, J=4.6 Hz, 4 H), 3.09 (t, J=4.6 Hz, 4 H).

EXAMPLE 15

2-Nitro-5-thiomorpholin-4-yl-phenylamine

A mixture of 5-chloro-2-nitrophenylamine (2.5 g, 14 mmol), thiomorpholine (3.0 g, 30 mmol), and K$_2$CO$_3$ (2.0 g, 14 mmol) in DMF (20 mL) was stirred at 120° C. for 18 h. The reaction mixture was cooled to room temperature and poured into water (150 mL). The crude product that precipitated was collected by filtration, dried in vacuo, and purified by flash chromatography (silica gel, 4×15 cm, eluted with 20% ether in CHCl$_3$) and recrystallized three times from methanol (MeOH) (0.49 g, 15%).

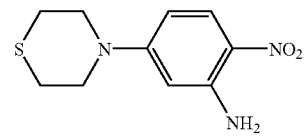

$^1$H NMR (90 MHz, CDCl$_3$) δ 8.01 (d, J=9.9 Hz, 1 H), 6.27–6.00 (m, 3 H), 5.90 (d, J=2.6 Hz, 1 H), 3.78(t, J=4.9 Hz, 4 H), 2.67 (t, J=4.9 Hz, 4 H).

IC$_{50}$ (nM) DNA-PK Assay—100,000.

EXAMPLE 16

N$^1$-Morpholin-4-yl-4-nitrobenzene-1,3-diamine

A mixture of 5-chloro-2-nitrophenylamine (2.5 g, 14 mmol), 4-aminomorpholine (4.4 g, 40 mmol), and K$_2$CO$_3$ (2.0 g, 14 mmol) in DMF (20 mL) was stirred at 120° C. for 18 h. The reaction mixture was cooled to room temperature and poured into water (150 mL). The crude solid product was collected by filtration, air dried, and purified by flash chromatography (silica gel, 4×15 cm, eluted with 20% ether in CHCl$_3$) to yield the product as a yellow solid (0.7 g, 20%).

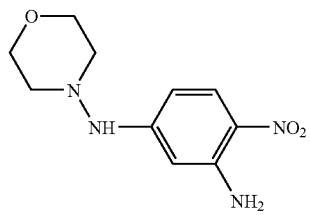

$^1$H NMR (90 MHz, CDCl$_3$) δ 8.06 (d, J=9.9 Hz, 1 H), 6.28 (dd, J=9.9, 2.6 Hz, 1 H), 6.05 (br s, 2 H), 5.97 (d, J=2.6 Hz, 1 H), 3.85 (t, J=4.9 Hz, 4 H), 3.32 (t, J=4.9 Hz, 4 H).

IC$_{50}$ (nM) DNA-PK Assay—1,000.

EXAMPLE 17

1-(3-Amino-4-nitrophenyl)-piperidin-4-ol

A mixture of 5-chloro-2-nitrophenylamine (1.3 g, 7.0 mmol), 4-hydroxypiperidine (2.2 g, 20 mmol), and K$_2$CO$_3$ (1.0 g, 7 mmol) in DMF (20 mL) was stirred at 120° C. for 18 h. The reaction mixture was cooled to room temperature, poured into water (50 mL) and extracted with EtOAc (3×50 mL). The combined organic extracts were dried over sodium sulfate, concentrated in vacuo, and the oily residue was triturated with 70/30 EtOAc/CHCl₃ (8 mL) to yield a yellow solid. The solid product was collected by filtration, washed with 70:30 EtOAc/CHCl₃ (8 mL), and dried in vacuo (0.63 g, 38%).

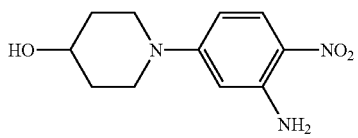

¹H NMR (90 MHz, CDCl₃+D₂O) δ 7.99 (d, 9.2 Hz, 1 H), 6.26 (dd, J=9.9, 2.6 Hz, 1 H), 6.08 (d, J=2.6 Hz, 1 H), 4.04–3.45 (m, 3 H), 3.22–2.88 (m, 2 H), 2.02–1.25 (m, 4 H).

EXAMPLE 18

2-Nitro-5-piperidin-1-yl-phenylamine

A mixture of 5-chloro-2-nitrophenylamine (5 g, 29 mmol), piperidine (2.9 mL, 29 mmol), and K₂CO₃ (4.0 g, 29 mmol) in DMF (20 mL) was stirred at 120° C. for 4 h. The reaction mixture was cooled to room temperature and poured into ice cold water (100 mL). The crude solid product was collected by filtration, air dried, and purified by flash chromatography (silica gel, 4×15 cm, eluted with CHCl₃) to yield the product as orange crystals (1.4 g, 22%). See, *Aust. J. Chem.*, 47:247–262 (1994).

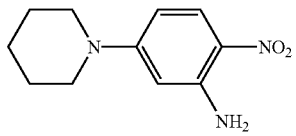

¹H NMR (90 MHz, CDCl₃) δ 7.90 (d, J=9.9 Hz, 1 H, 6.25–6.00 (m, 3 H), 5.86 (d, J=2.6 Hz, 1 H), 3.29 (br s, 4 H), 1.58 (br s, 6 H).

EXAMPLE 19

5-(4-Acetylpiperazin-1-yl)-2-nitrophenylamine

A mixture of 5-chloro-2-nitrophenylamine (5 g, 29 mmol), 1-acetylpiperazine (29 mmol), and K₂CO₃ (4.0 g, 29 mmol) in DMF (20 mL) was stirred at 120° C. for 4 h. The reaction mixture was cooled to room temperature and poured into ice cold water (100 mL). The crude solid product was collected by filtration, air dried, and purified by flash chromatography (silica gel, 4×15 cm, eluted with CHCl₃) to yield the product as orange crystals.

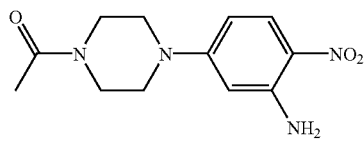

¹H NMR (90 MHz, CDCl₃) δ 11.46 (s, 1 H), 9.59 (s, 1 H), 7.35 (d, J=9.5 Hz, 1 H), 6.46 (dd, J=9.5, 2.3 Hz, 1 H), 6.28 (d, J=2.0 Hz, 1 H), 3.83 (t, J=4.6 Hz, 4 H), 3.35 (t, J=4.9 Hz, 4 H).

EXAMPLE 20

2-Nitro-5-piperazin-1-yl-phenylamine

A mixture of 5-chloro-2-nitrophenylamine (4.3 g, 25 mmol), piperazine (12.5 g, 145 mmol), and K₂CO₃ (4.0 g, 29 mmol) in DMF (50 mL) was stirred at 150° C. for 18 h. The reaction mixture was cooled to room temperature, solids were removed by filtration, and the filtrate was concentrated to a red residue. The residue was dissolved in EtOAc (100 mL), washed with water (50 mL), dried with Na₂SO₄, and concentrated in vacuo to afford the product as a yellow solid (3.9 g, 70%). See, *Pharmazie*, 39:747 (1984).

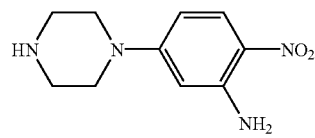

¹H NMR (90 MHz, d6-DMSO) δ 7.89 (d, J=9.9 Hz, 1 H), 7.09 (br s, 2 H), 6.35–6.20 (m, 2 H), 3.33 (t, J=4.6 Hz, 4 H), 2.91 (t, J=4.8 Hz, 4 H).
IC₅₀ (nM) DNA-PK Assay—10,000.

EXAMPLE 21

1-(3-Amino-4-nitrophenyl)-piperidin-3-ol

A mixture of 5-chloro-2-nitrophenylamine (1.3 g, 7.0 mmol), 3-hydroxypiperidine hydrochloride (3.0 g, 20 mmol), and K₂CO₃ (3.0 g, 22 mmol) in DMF (10 mL) was stirred at 120° C. for 18 h. The reaction mixture was cooled to room temperature, poured into water (100 mL) and extracted with EtOAc (3×100 mL). The combined organic extracts were dried over Na₂SO₄, concentrated in vacuo, and purified by flash chromatography (silica gel, 4×7.5 cm, eluted with 50:50 CHCl₃/EtOAc) to yield the product as an orange solid (0.89 g, 54%).

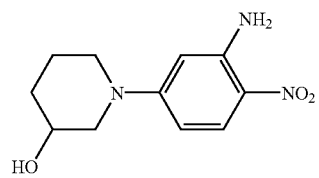

¹H NMR (90 MHz, d6-DMSO/CDCl₃) δ 7.77 (d, J=9.0 Hz, 1 H), 6.25–6.00 (m, 2 H), 3.82–3.25 (m, 3 H), 3.02–2.62 (m, 2 H), 1.90–1.12 (m, 4 H).
IC₅₀ (nM) DNA-PK Assay—100,000.

EXAMPLE 22

N¹-(2-Morpholin-4-yl-ethyl)-4-nitrobenzene-1,3-diamine

A mixture of 5-chloro-2-nitrophenylamine (1.3 g, 7.0 mmol), 2-(4-morpholinyl)-ethylamine (2.8 g, 20 mmol), and K$_2$CO$_3$ (3.0 g, 22 mmol) in DMF (20 mL) was stirred at 110° C. for 48 h. The reaction mixture was cooled to room temperature, poured into water (200 mL) and extracted with dichloromethane (CH$_2$Cl$_2$) (250 mL). The combined organic extracts were washed with water (200 mL) and brine (200 mL), dried over Na$_2$SO$_4$, concentrated in vacuo, and purified by flash chromatography (silica gel, 4×15 cm, eluted with 90:10 EtOAc/MeOH) to yield the product as an orange solid (0.39 g, 20%).

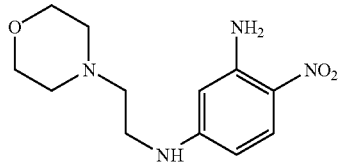

$^1$H NMR (300 MHz, CDCl$_3$) δ 7.96 (d, J=9.4 Hz, 1 H), 6.23 (br s, 2 H) 6.00 (dd, J=9.5, 2.1 Hz, 1 H), 5.69 (d, J=1.9 Hz, 1 H), 5.09 (s, 1 H), 3.74 (br t, J=4.3 Hz, 4 H), 3.20 (br quartet, J=5.3 Hz, 2 H), 2.65 (t, J=5.8 Hz, 2 H), 2.49 (br s, 4 H).

IC$_{50}$ (nM) DNA-PK Assay—100,000.

EXAMPLE 23

5-(4-(2-Methoxyphenyl)-piperazin-1-yl]-2-nitrophenylamine

A mixture of 5-chloro-2-nitrophenylamine (1.3 g, 7.0 mmol), 1-(2-methoxyphenyl)-piperazine hydrochloride (5.0 g, 20 mmol), and K$_2$CO$_3$ (4.0 g, 29 mmol) in DMF (20 mL) was stirred at 110° C. for 18 h. The reaction mixture was cooled to room temperature and poured into water (200 mL). The crude solid product was collected by filtration, air dried, and purified by trituration with CHCl$_3$ (1.3 g, 57%).

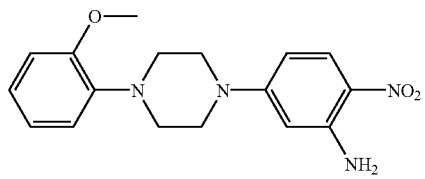

$^1$H NMR (90 MHZ, d6-DMSO/CDCl$_3$) δ 8.23–7.83 (m, 2 H), 7.17 (br s, 2 H), 6.93 (br s, 3 H), 6.42–6.28 (m, 2 H), 3.87 (s, 3 H), 3.52–3.41, (m, 4 H), 3.20–3.12 (m, 4 H).

IC$_{50}$ (nM) DNA-PK Assay—100,000.

EXAMPLE 24

5-(cis-2,6-Dimethylmorpholin-4-yl)-2-nitrophenylamine

A mixture of 5-chloro-2-nitrophenylamine (1.3 g, 7.0 mmol), cis-2,6-dimethylmorpholine (2.5 g, 20 mmol), and K$_2$CO$_3$ (3.0 g, 22 mmol) in DMF (20 mL) was stirred at 110° C. for 48 h. The reaction mixture was cooled to room temperature, poured into water (300 mL). The resulting crude yellow solid was collected by vacuum filtration, air dried, and purified by flash chromatography (silica gel, 4×7.5 cm, eluted with 95/5 CHCl$_3$/ether) to yield the product as a yellow solid (1.2 g, 68%).

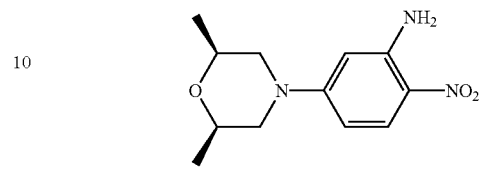

$^1$H NMR (90 MHz, CDCl$_3$) δ 8.03 (d, J=9.9 Hz, 1 H), 6.33–5.96 (m, 4 H), 3.82–3.55 (m, 4 H), 2.58 (t, J=11.9 Hz, 2 H), 1.28 (d, J=6.5 Hz, 6 H).

$^{13}$C NMR (75 MHz, CDCl$_3$) δ 155.4, 147.0, 128.3, 125.7, 105.4, 98.6, 71.3, 52.6, 18.9.

IC$_{50}$ (nM) DNA-PK Assay—100,000.

EXAMPLE 25

2-Nitro-5-(4-pyridin-2-yl-piperazin-1-yl)-phenylamine

A mixture of 5-chloro-2-nitrophenylamine (1.3 g, 7.0 mmol), 1-(2-pyridyl)-piperazine (3.5 g, 20 mmol), and K$_2$CO$_3$ (3.0 g, 22 mmol) in DMF (20 mL) was stirred at 110° C. for 48 h. The reaction mixture was cooled to room temperature and poured into water. The crude yellow solid was collected by vacuum filtration, air dried, and recrystallized from CHCl$_3$ (0.36 g, 17%).

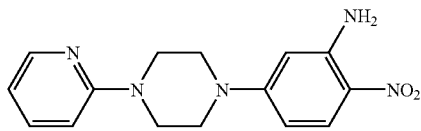

$^1$H NMR (90 MHz, CDCl$_3$) δ 8.25–7.99 (m, 2 H), 7.53–7.42 (m, 1 H), 6.74–6.61 (m, 2 H), 6.36–5.95 (m, 4 H), 3.73–3.46 (m, 8 H).

IC$_{50}$ (nM) DNA-PK Assay—100,000.

EXAMPLE 26

N$^1$-(3-Morpholin-4-yl-propyl)-4-nitrobenzene-1,3-diamine

A mixture of 5-chloro-2-nitrophenylamine (1.3 g, 7.0 mmol), 3-(4-morpholinyl)-1-aminopropane (3.1 g, 20 mmol), and K$_2$CO$_3$ (3.0 g, 22 mmol) in DMF (20 mL) was stirred at 110° C. for 18 h. The reaction mixture was cooled to room temperature, poured into water (200 mL) and extracted with CH$_2$Cl$_2$ (100 mL). The combined organic extracts were washed with brine (50 mL), dried over Na$_2$SO$_4$, concentrated in vacuo, and purified by flash chromatography (silica gel, 4×7.5 cm, eluted with 90/10 EtOAc/MeOH) to yield the product as an orange solid (0.45 g, 23%).

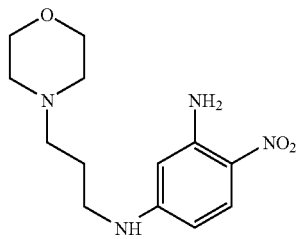

$^1$H NMR (90 MHz, CDCl$_3$) δ 7.93 (d, J=9.9 Hz, 1 H), 6.23 (br s, 3 H), 5.92 (dd, J=9.2, 2.0 Hz, 1 H), 5.65 (d, J=2.0 Hz, 1 H), 3.74 (t, J=4.6 Hz, 4 H), 3.13 (br s, 2 H), 2.58–2.44 (m, 6 H), 1.80 (pentet, J=5.9 Hz, 2 H).
$^{13}$C NMR (75 MHz, CDCl$_3$) δ 154.2, 147.8, 128.5, 124.5, 105.9, 94.6, 67.1, 57.5, 53.8, 42.8, 24.8.
IC$_{50}$ (nM) DNA-PK Assay—100,000.

EXAMPLE 27

2-Hydroxy-4-morpholin-4-yl-benzonitrile

A solution of 4-(4-morpholinyl)-salicylaldehyde oxime (0.9 g, 4 mmol) pyridine (10 mL) was treated with trifluoroacetic anhydride (2.3 mL, 16 mmol), stirred 18 h at room temperature, and concentrated in vacuo at 80° C. The residue was dissolved in a mixture of EtOAc (15 mL) and CHCl$_3$ (10 mL), washed with water (2×20 mL), dried over Na$_2$SO$_4$, and concentrated in vacuo. The product was purified by flash chromatography (silica gel, 4×7.5 cm, eluted with 80/20 CHCl$_3$/ether) to yield the product as a white solid (0.38 g, 42%).

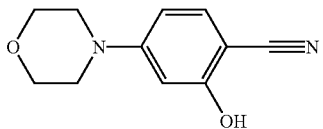

$^1$H NMR (90 MHz, CDCl$_3$) δ 7.30 (d, J=10.8 Hz, 1 H), 6.50–6.40 (m, 2 H), 3.62, (t, J=5.4 Hz, 4 H), 3.10 (t, J=5.4 Hz, 4 H).
$^{13}$C NMR (75 MHz, CDCl$_3$) δ 161.7, 156.5, 134.7, 118.0, 107.8, 101.5, 90.2, 67.0, 48.3. LRMS (EI): m/e 204 (M$^+$). IR (KBr): 3222, 2240 (CN), 1620 cm$^{-1}$.
IC$_{50}$ (nM) DNA-PK Assay—100,000.

EXAMPLE 28

(5-Morpholin-4-yl-2-nitrophenyl)-methanol

A mixture of 5-chloro-2-nitrobenzyl alcohol (1.9 g, 10.0 mmol), morpholine (0.9 mL, 10 mmol), and K$_2$CO$_3$ (1.4 g, 10 mmol) in DMF (20 mL) was stirred at 110° C. for 18 h. The reaction mixture was concentrated in vacuo, poured into aqueous sodium bicarbonate (NaHCO$_3$) (5% w/v, 25 mL), and extracted with dichloromethane (25 mL). The organic extract was washed with brine (25 mL), dried over Na$_2$SO$_4$, concentrated in vacuo, and purified by flash chromatography (silica gel, 4×7.5 cm, eluted with 90/10 EtOAc/MeOH) to yield a solid impure product. The residue was repurified in the same manner and the resulting solid was triturated with hexanes (10 mL) to afford the product as a yellow solid (5 mg, 2%).

$^1$H NMR (90 MHz, CDCl$_3$) δ 8.14 (d, J=9.2 Hz, 1 H), 7.03 (d, J=3.3 Hz, 1 H), 6.75 (dd, J=9.2, 3.3 Hz, 1 H), 4.95 (d, J=4.0 Hz, 2 H), 3.85 (t, J=4.9 Hz, 4 H), 3.39 (t, J=4.9 Hz, 4 H). $^{13}$C NMR (75 MHz, CDCl$_3$) δ 154.7, 139.9, 138.1, 128.2, 113.3, 111.8, 66.4, 63.7, 47.3.

EXAMPLE 29

2-Hydroxy-4-morpholin-4-yl-benzoic acid

A solution of 2-hydroxy-4-morpholin-4-yl-benzonitrile (0.3 g, 1.5 mmol) in concentrated HCl (10 mL) was stirred at reflux for 6 h, and concentrated in vacuo. The residue was dissolved in an additional portion of HCl (10 mL) and stirred under reflux for 6 h and concentrated to a dark solid. The solid was dissolved in aqueous sodium hydroxide (10% w/v, 2.5 mL) and treated with 6 N HCl (1 mL) to precipitate the product which was collected by filtration, washed with water (5 mL), and dried in vacuo at 40° C. (95 mg, 28%).

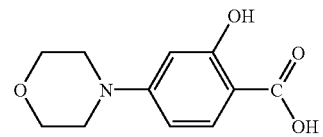

$^1$H NMR (90 MHz, d6-DMSO/D$_2$O): δ 7.58 (d, J=9.2 Hz, 1 H), 6.48 (d, J=9.2 Hz, 1 H), 6.33 (br s, 1 H), 3.70 (t, J=4.3 Hz, 4 H), 3.24 (t, J=4.3 Hz, 4 H). $^{13}$C NMR (75 MHz, d6-DMSO/D$_2$O): δ 171.5, 162.8, 156.2, 131.3, 105.9, 102.6, 99.8, 65.9, 46.8. IR (KBr): 2975, 1626, 1570, 1515, 1240 cm$^{-1}$.
IC$_{50}$ (nM) DNA-PK Assay—500.

EXAMPLE 30

2-Hydroxy-4-morpholin-4-yl-benzoic acid methyl ester

A solution of 2-hydroxy-4-morpholin-4-yl-benzonitrile (0.4 g, 2.0 mmol) in concentrated HCl (20 mL) was stirred at reflux for 16 h, and concentrated in vacuo to yield the corresponding carboxylic acid as a crude solid. The solid was suspended in MeOH (20 mL), treated with a solution of hydrogen chloride in dioxane (4 M, 10 mL), stirred at reflux for 20 h, concentrated, treated again in the same manner and stirred 24 h at reflux. The reaction mixture was concentrated, and the residue was dissolved in EtOAc (20 mL), washed with aqueous sodium bicarbonate (5%, 10 mL), dried over Na$_2$SO$_4$, and concentrated. The residue was purified by flash chromatography (silica gel, 4×7.5 cm, eluted with CHCl$_3$) to yield the product as a white solid (137 mg, 29%).

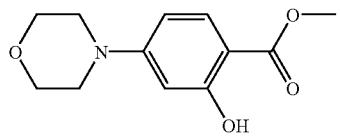

$^1$H NMR (90 MHz, CDCl$_3$): δ 7.65 (d, J=10.7 Hz, 1 H), 6.49–6.31 (m, 2 H), 3.87 (s, 3 H), 3.80 (t, J=4.9 Hz, 4 H), 3.24 (t, J=4.9 Hz, 4 H). $^{13}$C NMR (75 MHz, CDCl$_3$): δ 170.2, 163.3, 156.3. 130.9, 105.9, 103.3, 100.6, 66.4, 51.5, 47.4.

IC$_{50}$ (nM) DNA-PK Assay—500.

EXAMPLE 31

5-Morpholin-4-yl-2-nitro-benzamide

A mixture of 5-chloro-2-nitrobenzamide (2.0 g, 10.0 mmol), morpholine (2.6 mL, 30 mmol), and K$_2$CO$_3$ (4.1 g, 30 mmol) in DMF (20 ml) was stirred at 110° C. for 24 h. The reaction mixture was poured into water (100 mL) and the resulting precipitate was collected by filtration and recrystallized from ethanol to yield the product as a yellow solid (0.5 g, 20%).

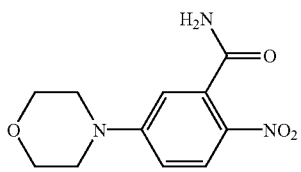

$^1$H NMR (90 MHz, d6-DMSO): δ 7.95 (d, J=9.2 Hz, 1 H), 7.85 (br s, 1 H), 7.51 (br s, 1 H), 7.06–6.86 (m, 2 H), 3.72 (t, J=4.3 Hz, 4 H), 3.38 (t, J=4.3 Hz, 4 H). $^{13}$C NMR (75 MHz, d6-DMSO): δ 169.2, 154.8, 137.3, 136.4, 127.4, 113.6, 113.0, 66.7, 47.7.

IC$_{50}$ (nM) DNA-PK Assay—100,000.

EXAMPLE 32

2-Hydroxy-4-morpholin-4-yl-benzaldehyde

DMF (10 mL) was treated dropwise with phosphorus oxychloride (2.3 g, 15 mmol). The reaction was kept at 25° C. by cooling on ice. The reaction mixture was treated with 3-(4-morpholinyl)phenol (2.5 g, 14 mmol) in small portions, stirred for 30 min at room temperature, then stirred at 100° C. for 8 h. After cooling, the mixture was poured into aqueous sodium acetate (1 M, 40 mL) and 10 mL of water was added. The resulting precipitate was collected by filtration, washed with water (10 mL), air dried, and purified by flash chromatography (silica gel, 4×7.5 cm, eluted with 90/10 CHCl$_3$/ether) to yield the product as a light gray solid (0.66 g, 23%). See U.S. Pat. No. 4,147,552.

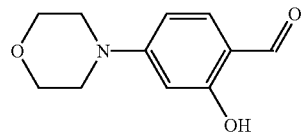

$^1$H NMR (90 MHz, CDCl$_3$) δ 11.45 (s, 1 H), 9.59 (s, 1 H), 7.36 (d, J=8.7 Hz, 1 H), 6.45 (dd, J=8.7, 2.6 Hz, 1 H), 6.27 (d, J=2.6 Hz, 1 H), 3.83 (t, J=5.4 Hz, 4 H), 3.35 (t, J=4.9 Hz, 4 H).

$^{13}$C NMR (22.5 MHz, CDCl$_3$) δ 193.0, 163.9, 156.9, 135.1, 113.3, 124.0, 99.6, 66.4, 47.0. LRMS (EI): m/e 207 (M$^+$), 149.

IC$_{50}$ (nM) DNA-PK Assay—400.

EXAMPLE 33

5-Morpholin-4-yl-2-nitro-phenol

A mixture of 2,4-dichloronitrobenzene (1.9 g, 10.0 mmol), morpholine (0.9 mL, 10 mmol), and K$_2$CO$_3$ (1.4 g, 10 mmol) in DMF (20 mL) was stirred at 110° C. for 18 h. The reaction mixture was poured into water (100 mL) and extracted with CH$_2$Cl$_2$ (2×50 mL). The combined organic extracts were washed with brine (25 mL), dried over Na$_2$SO$_4$, concentrated in vacuo to yield 1.6 g of the crude intermediate, a mixture of regioisomers: 4-(5-chloro-2-nitrophenyl)-morpholine: 4-(3-chloro-4-nitrophenyl)-morpholine, 80:20.

The crude mixture (7 mmol) was suspended in water (85 mL) and treated with sodium hydroxide (2.8 g, 70 mmol) and stirred at 150° C. for 16 h in a sealed container. After cooling to room temp, the mixture was extracted with ether (2×50 mL) to remove unreacted starting material. The aqueous layer was acidified with acetic acid (4.2 mL, 70 mmol) to pH 6 and then extracted with ether (3×100 mL). The ether extracts were dried over Na$_2$SO$_4$, concentrated in vacuo, and purified by flash chromatography (silica gel, 4×7.5 cm, eluted with 90/10 CHCl$_3$/ether) to yield the faster-moving product as a yellow solid (45 mg, 2%). The position of the morpholine was confirmed by 1D-Noe studies, irradiating both aromatic and morpholinyl protons. See, *Organic Syntheses Coll., Vol. II,* 451 (1943).

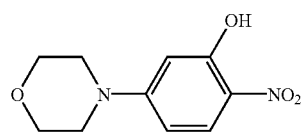

$^1$H NMR (90 MHz, CDCl$_3$) δ 11.1 (s, 1 H), 7.87 (d, J=9.2 Hz, 1 H), 6.39–6.21 (m, 2 H), 3.77 (t, J=4.9 Hz, 4 H), 3.32 (t, J=4.9 Hz, 4 H). $^{13}$C NMR (75 MHz, CDCl$_3$) δ 157.9, 157.0, 127.2, 125.5, 106.6, 100.0, 66.3, 47.0. LRMS (EI): 222 (M$^+$), 94.

IC$_{50}$ (nM) DNA-PK Assay—2000.00

EXAMPLE 34

1-(2-Hydroxy-4-morpholin-4-yl-phenyl)-ethanone

A solution of 2-hydroxy-4-morpholin-4-yl-benzaldehyde (1.0 g, 5 mmol) in anhydrous tetrahydrofuran (20 mL) at −78° C. was treated with methyilithium (1.5 M solution in peiitane, 7.1 mL, 11 mmol) at the rate of 0.5 mL/min. The reaction mixture was stirred at the same temperature for 1.5 h, allowed to warm to room temperature for 1 h, cooled to 0° C., then quenched with sat. ammonium chloride (4 mL). The mixture was extracted with ether (20 mL), and the ether layer was washed with 5% sodium bicarbonate (15 mL), dried over $Na_2SO_4$, and concentrated in vacuo to yield the desired intemniediate carbinol (1.1 g).

The crude carbinol intermediate (0.6 g, 2.7 mmol) was dissolved in acetonitriLe (25 mL) and treated with manganese dioxide (2.34 g, 27 mmol) and stirred for 48 h at room temperature. The solids were filtered off through a pad of CELITE®, washed with acetonitmLe (20 mL), and discarded. The filtrate was concentrated in vacuo and purified by flash chromatography (silica gel, 4×7.5 cm, eluted with 90/10 $CH_2Cl_2$/ether) to yield the product as a white solid (208 mg, 25%).

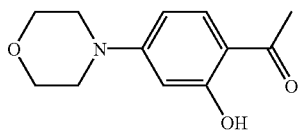

$^1$H NMR (90 MHz, $CDCl_3$) δ 7.55 (d, J=9.2 Hz, 1 H), 6.43–6.28 (m, 2 H), 3.83 (t, J=4.6 Hz, 4 H), 3.31 (t, J=4.9 Hz, 4 H), 2.51 (s, 3 H).
$^{13}$C NMR (75 MHz, $CDCl_3$) δ 201.3, 165.0, 156.6, 132.2, 112.3, 105.4, 100.6, 66.5, 47.2, 25.6. LRMS (EI): m/e 221 ($M^+$), 206, 163, 148.

$IC_{50}$ (nM) DNA-PK Assay—120.

EXAMPLE 35

1-(2-Hydroxy-4-morpholin-4-yl-phenyl)-propan-1-one

Following the procedure for preparing Example 34, 4-(4-morpholinyl)-salicylaldehyde (1.0 g, 5 mmol) and ethyl-magnesium bromide (1.0 M solution in tetrahydrofuran, 11 mL, 11 mmol) were converted to the product (208 mg, 18%).

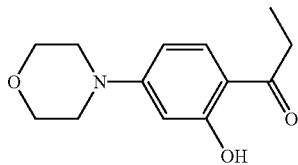

$^1$H NMR (300 MHz, $CDCl_3$): δ 12.8 (s, 1 H), 7.60 (d, J=9.1 Hz, 1 H), 6.37 (dd, J=9.1, 2.5 Hz, 1 H), 6.28 (d, J=2.5 Hz, 1 H), 3.82 (t, J=5.0 Hz, 4 H), 3.31 (t, J=5.0 Hz, 4 H), 2.90 (q, J=7.3 Hz, 2 H), 1.21 (t, J=7.3 Hz, 3 H).
$^{13}$C NMR (75 MHz, $CDCl_3$): δ 204.3, 165.0, 156.4, 131.4, 111.5, 105.4, 100.7, 66.4, 47.2, 30.7, 8.8.

$IC_{50}$ (nM) DNA-PK Assay—120.

EXAMPLE 36

1-(2-Hydroxy-4-morpholin-4-yl-phenyl)-3-methyl-butan-1-one

Following the procedure for preparing Example 34, 4-(4-morpholinyl)-salicylaldehyde (1.0 g, 5 mmol) and propyl-magnesium bromide (2.0 M solution in tetrahydrofuran, 5.5 mL, 11 mmol) were converted to the product (230 mg, 19%).

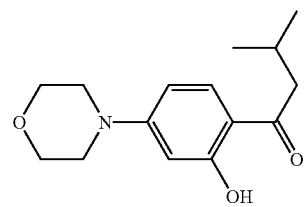

$^1$H NMR (300 MHz, $CDCl_3$): δ 13.0 (s, 1 H), 7.60 (d, J=9.2 Hz, 1 H), 6.37 (dd, J=9.1, 2.6 Hz, 1 H), 6.28 (d, J=2.5 Hz, 1 H), 3.82 (t, J=4.9 Hz, 4 H), 3.31 (t, J=4.9 Hz, 4 H), 2.71 (d, J=7.0 Hz, 2 H), 2.32–2.18 (m, 1 H), 0.99 (d, J=6.7 Hz, 6 H). $^{13}$C NMR (75 MHz, $CDCl_3$): δ 203.7, 165.2, 156.4, 131.8, 112.2, 105.3, 100.7, 66.5, 47.2, 46.5, 26.1, 22.7.

$IC_{50}$ (nM) DNA-PK Assay—150.

EXAMPLE 37

1-(2-Hydroxy-4-morpholin-4-yl-phenyl)-1-phenyl-methanone

Following the procedure for preparing Example 34, 4-(4-morpholinyl)-salicylaldehyde (1.0 g, 5 mmol) and phenyl-lithium (1.8 M solution in tetrahydrofuran, 6.0 mL, 11 mmol) were converted to the product (387 mg, 28%).

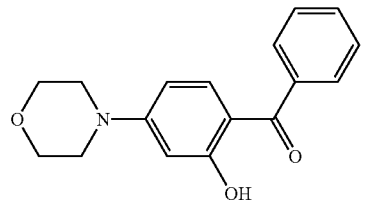

$^1$H NMR (300 MHz, $CDCl_3$) δ 12.74 (s, 1 H), 7.64–7.43 (m, 6 H), 6.38 (d, J=2.3 Hz, 1 H), 6.33 (dd, J=9.1, 2.3 Hz, 1 H), 3.84 (t, J=4.9 Hz, 4 H), 3.36 (t, J=4.9 Hz, 4 H). $^{13}$C NMR (75 MHz, $CDCl_3$) δ 198.9, 166.0, 156.5, 138,8, 135.2, 131.0, 128.7, 128.2, 111.3, 105.1, 100.5, 66.4, 47.1.

$IC_{50}$ (nM) DNA-PK Assay—120.

EXAMPLE 38

2,2,2-Trifluoro-1-(2-hydroxy-4-morpholin-4-yl-phenyl)-ethanone

A solution of 4-(morpholin-4-yl)-salicylaldehyde (1 g, 4.8 mmol), in tetrahydrofuran (10 mL) was treated with a solution of trimethyl(trifluoromethyl)silane (0.5 M in tetrahydrofuran, 21 mL, 10.5 mmol) and tetra-n-butylammonium fluoride (20 mg, catalytic). After stirring for 3 h at room temperature, the reaction mixture was poured into ether (100 mL), washed with brine (25 mL), saturated aqueous NaHCO$_3$ (25 mL), brine (25 mL), dried over magnesium sulfate, and concentrated to a syrup that solidified upon standing (1.35 g crude carbinol).

The crude carbinol (1.16 g, 4.18 mmol) was dissolved in CH$_2$Cl$_2$ and the solution was treated with oxo-bis-trifluoromethyl-1,3-dihydro-1(5-1,2-benziodoxol-1-ol (3.36 g, 8.36 mmol) and stirred for 1 h at room temperature. The reaction mixture was filtered through a plug of silica gel (150 g in a 250 mL fritted funnel) and the silica gel was washed with CH$_2$Cl$_2$. The combined filtrates were concentrated to a syrup and treated with hexanes (50 mL). The resulting precipitate was removed by filtration and discarded. The filtrate was concentrated and purified by flash chromatography (silica gel, 4×15 cm, eluted with 5–15% ether in hexanes) to yield the product as a yellow solid (220 mg, 19%). M.P.: 81–82° C. See, *J. Org. Chem.* 56:984 (1991); *J. Am. Chem. Soc.* 115:6078 (1993).

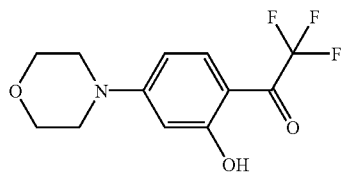

$^1$H NMR (300 MHz, CDCl$_3$) δ 11.62 (s, 1 H), 7.76 (d, J=9.2 Hz, 1 H), 6.42 (d, J=9.2 Hz, 1 H), 6.26 (s, 1 H), 3.81 (t, J=4.9 Hz, 4 H), 3.41 (t, J=4.9 Hz, 4 H). $^{13}$C NMR (75 MHz, CDCl$_3$) δ 180.6 (q, JC-F=34 Hz), 167.4, 157.5, 132.3, 117.2 (q, JC-F=288 Hz), 106.3, 106.0, 99.6, 66.3, 46.7. LRMS (EI): 275 (M+), 206, 148.

IC$_{50}$ (nM) DNA-PK Assay—250.

EXAMPLE 39

4-Amino-2-morpholin-4-yl-pyrimidine-5-carboxylic acid

A mixture of 4-amino-5-carboxy-2-ethylmercaptopyrimidine (0.35 g, 1.8 mmol) and morpholine (0.5 mL, 10 mmol) was warmed at 80° C. for 4 d and concentrated in vacuo. The residue was purified by flash chromatography (silica gel, 4×7.5 cm, eluted with 97.25/2.5/0.25 acetonitrile/water/acetic acid) to yield the product as a white solid (34 mg, 30%).

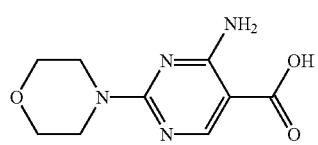

$^1$H NMR (300 MHz, d6-DMSO) δ 8.49 (s, 1 H), 7.65 (br s, 1 H), 7.35, (br s, 1 H), 3.75 (t, J=4.4 Hz, 4 H), 3.63 (t, J=4.4 Hz, 4 H). $^{13}$C NMR (75 MHz, d6-DMSO) δ 167.5, 162.9, 161.5, 160.5, 95.5, 65.8, 43.7.

IC$_{50}$ (nM) DNAPK Assay—100,000.

EXAMPLE 40

1-(5-Bromo-2-hydroxy-4-morpholin-4-yl-phenyl)-ethanone

A solution of 4-(4-morpholinyl)-2-hydroxyacetophenone (0.38 g, 1.3 mmol) in CHCl$_3$ was added to a suspension of cupric bromide (0.46 g, 2.0 mmol) in EtOAc (10 mL) and stirred for 16 h at reflux. The reaction mixture was treated with more cupric bromide (0.39 g, 1.7 mmol) and stirred 20 h at reflux. Solids were filtered off, and the filtrate was concentrated and purified by flash chromatography (silica gel, 4×7.5 cm, eluted with 15–20% ether in hexanes) to yield the product as a yellow solid (111 mg, 28%).

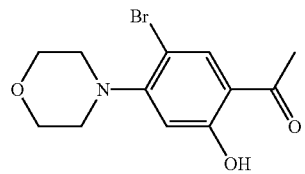

$^1$H NMR (300 MHz, CDCl$_3$) δ 12.39 (s, 1H), 7.87 (s, 1H), 6.53 (s, 1H), 3.87 (t, J=4.5 Hz, 4 H), 3.15 (t, J=4.5 Hz, 4 H), 2.56 (s, 3 H).

IC$_{50}$ (nM) DNA-PK Assay—100,000.

EXAMPLE 41

1-(3-Bromo-2-hydroxy-4-morpholin-4-yl-phenyl)-ethanone

A solution of 4-(4-morpholinyl)-2-hydroxyacetophenone (0.17 g, 0.6 mmol) in MeOH was treated with cupric bromide (0.20 g, 0.9 mmol) and stirred for 16 h at reflux. The reaction mixture was treated with more cupric bromide (0.39 g, 1.7 mmol) and stirred 20 h at reflux. The solids were filtered off, and the filtrate was concentrated and purified by flash chromatography (silica gel, 4×7.5 cm, eluted with 10% ether in hexanes) to yield the product as a yellow syrup (62 mg, 34%).

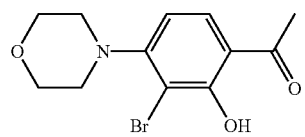

$^1$H NMR (300 MHz, CDCl$_3$) δ 7.66 (d, J=8.5 Hz, 1 H), 6.56 (d, J=8.5 Hz, 1 H), 3.88 (t, J=4.5 Hz, 4 H), 3.20 (t, J=4.5 Hz, 4 H). $^{13}$C NMR (75 MHz, CDCl$_3$) δ 202.5, 161.0, 157.5, 130.5, 115.9, 110.6, 106.5, 66.9, 51.5, 26.0.

IC$_{50}$ (nM) DNA-PK Assay—100,000.

EXAMPLE 42

A: 1-(3,5-Dichloro-2-hydroxy-4-morpholin-4-yl-phenyl)-ethanone

B: 1-(3-Chloro-2-hydroxy-4-morpholin-4-yl-phenyl)-ethanone

A solution of 4-(4-morpholinyl)-2-hydroxyacetophenone (0.21 g, 0.7 mmol) in glacial acetic acid (2 mL) was treated with chlorine gas and stirred 18 h at room temperature. The entire mixture was poured into water (30 mL) and extracted with ether (2×25 mL). The combined organic extracts were washed with 5% NaHCO₃ (2×30 mL) and brine (30 mL), dried with Na₂SO₄, concentrated in vacuo. The residue was purified by flash chromatography (silica gel, 4×7.5 cm, eluted with 10–20% EtOAc in hexanes) to yield A (faster-eluting band, 40 mg, 18%) and B (slower-eluting band, 60 mg, 27%). See, ACCUFLUOR® brochure from Allied-Signal Corp.

A:

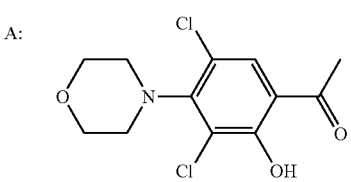

$^1$H NMR (300 MHz, CDCl₃) δ 12.97 (s, 1 H), 7.66 (s, 1 H), 3.85 (t, J=4.5 Hz, 4 H), 3.36 (t, J=4.5 Hz, 4 H), 2.60 (s, 3 H). LRMS (EI): 291/289 (M⁺), 254, 231, 216.

IC₅₀ (nM) DNA-PK Assay—100,000.

B:

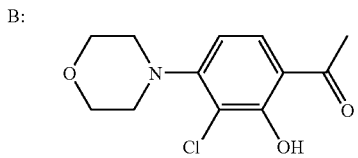

$^1$H NMR (300 MHz, CDCl₃) δ 13.19 (s, 1 H), 7.62 (d, J=8.9 Hz, 1 H), 6.56 (d, J=8.9 Hz, 1 H), 3.39 (t, J=4.6 Hz, 4 H), 3.22 (t, J=4.5 Hz, 4 H), 2.60 (s, 3 H). LRMS (EI): 257/255 (M⁺), 199, 182.

IC₅₀ (nM) DNA-PK Assay—14,000.

EXAMPLE 43

C: 1-(5-Fluoro-2-hydroxy-4-morpholin-4-yl-phenyl)-ethanone

D: 1-(3-Fluoro-2-hydroxy-4-morpholin-4-yl-phenyl)-ethanone

A solution of 4-(4-morpholinyl)-2-hydroxyacetophenone (1.0 g, 4.5 mmol) in acetonitmLe (20 mL) was treated with ACCUFLUOR® NFTh (50% w/w on alumina, 5.8 g, 9 mmol) and warmed at 40° C. for 48 h. The solids were removed by filtration, and the filtrate was concentrated, dissolved in CH₂Cl₂ (50 mL), and washed with 5% NaHCO₃ (50 mL). The CH₂Cl₂ layer was dried over Na₂SO₄, concentrated, and the residue was purified by flash chromatography (silica gel, 4×7.5 cm, eluted with 15% EtOAc in hexanes) to yield C (faster-eluting band, 83 mg, 8%) and D (slower-eluting band, 95 mg, 9%).

C:

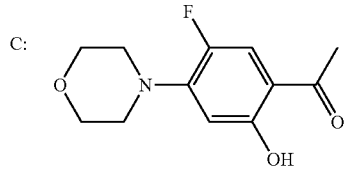

$^1$H NMR (300 MHz, CDCl₃): δ 12.41 (s, 1 H), 7.29 (d, JH-F=13.5 Hz, 1 H), 6.34 (d, JH-F=7.4 Hz, 1 H), 3.85 (t, J=4.5 Hz, 4 H), 3.26 (t, J=4.5 Hz, 4 H), 2.50 (s, 3 H). $^{13}$C NMR (75 MHz, CDCl₃): δ 202.4, 161.6, 148.2 (d, JC-F=9 Hz), 148.1 (d, JC-F=240 Hz), 117.5 (d, JC-F=23 Hz), 112.9, 106.5, 67.6, 50.8, 27.0. LRMS (EI): m/e 239 (M⁺), 224, 167, 155.

IC₅₀ (nM) DNA-PK Assay—1,500.

D:

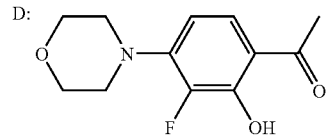

$^1$H NMR (300 MHz, CDCl₃): δ 12.51 (s, 3 H), 7.44 (dd, JH-H=8.8 Hz, JH-F=1.6 Hz, 1H), 6.41 (JH-H=8.8 Hz, JH-F=7.7 Hz, 1 H), 3.88 (t, J=4.5 Hz, 4 H), 3.30 (t, J=4.5 Hz, 4 H). $^{13}$C NMR (75 MHz, CDCl₃): δ 202.6, 152.4 (d, JC-F=13 Hz), 145.4 (d, JC-F=4 Hz), 142.2 (d, JC-F=244 Hz), 126.3, 115.1, 107.4, 67.0, 49.9, 26.0. LRMS (EI): m/e 239 (M⁺), 224, 196, 167, 155, 127.

IC₅₀ (nM) DNA-PK Assay—240.00

EXAMPLE 44

1-(2-Hydroxy-4-(tetrahydropyran-4-yloxy)-phenyl]-ethanone

A mixture of tetrahydro-4H-pyran-4-ol (1.53 g, 15 mmol), 2,4-dihydroxyacetophenone (1.52 g, 10 mmol), and triphenyiphosphine, polymer-bound (5 g, 3 mmol P/g resin, 15 mmol) in CH₂Cl₂ (150 mL) was treated with diethyilazodicarboxylate (2.61 g, 15 mmol) and stirred at 20° C. for 20 h. The reaction mixture was treated with ether (200 mL) and the resin was filtered off and discarded. The filtrate was concentrated irn vacuo and purified by flash chromatography (silica gel, 4×7.5 cm, eluted with 25% ether in hexanes) to yield the white solid product (0.74 g, 31%).

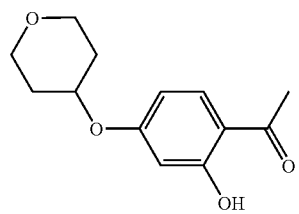

M.P.: 99–104° C. $^1$H NMR (90 MHz, CDCl₃) δ 12.71 (s, 1 H), 7.63 (d, J=9.9 Hz, 1 H), 6.50–6.40 (m, 2 H), 4.60–4.50 (m, 1 H), 4.11–3.85 (m, 2 H), 3.67–3.45 (m, 2 H), 2.55 (s,

3 H), 2.00–1.74 (m, 4 H). $^{13}$C NMR (75 MHz, CDCl$_3$) δ 200.2, 165.1, 163.9, 132.3, 114.0, 108.5, 102.4, 71.9, 64.8, 31.5, 25.8.

IC$_{50}$ (nM) DNA-PK Assay—100,000.

EXAMPLE 45

5-(Morpholin-4-yl)-1,3-dihydro-benzimidazol-2-one

A solution of 5-morpholin-4-yl-2-nitro-phenylamine (4.0 g, 0.02 mol) in acetic acid (100 mL) and ethanol (100 mL) was treated with hydrogen gas (60 psi) for 30 min in the presence of palladium on carbon catalyst (0.5 g, 10% Pd). The catalyst was removed by filtration through CELITE®, and the filtrate was concentrated to a syrup and dried in vacuo to afford the intermediate 4-morpholin-4-yl-benzene-1,2-diamine as a crude green solid (3.2 g).

A solution of crude 4-morpholin-4-yl-benzene-1,2-diamine (0.75 g, 3.9 mmol) in tetrahydrofuran (4 mL) was treated dropwise with a solution of carbonyldiimidazole (0.76 g, 4.7 mmol) in tetrahydrofuran (12 mL). The reaction mixture was stirred for 16 h at room temperature, and the solid product was collected by filtration and recrystallized from ethanol to afford the white solid product (0.47 g, 55%). See, *J. Am. Chem., Soc.,* 118:4018 (1996).

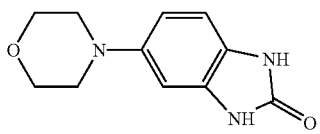

$^1$H NMR (90 MHz, d6-DMSO): δ 11.17 (s, 1 H), 11.05 (s, 1 H), 7.55 (d, J=9.2 Hz, 1 H), 7.32–7.24 (m, 2 H), 4.46 (t, J=4.3 Hz, 4 H), 3.70 (t, J=4.6 Hz, 4 H). $^{13}$C NMR (75 MHz, d6-DMSO): δ 155.4, 146.2, 130.3, 123.4, 108.9, 108.4, 97.5, 66.1, 50.2.

IC$_{50}$ (nM) DNA-PK Assay—100,000.

EXAMPLE 46

A: 2-Methoxy-4-morpholin-4-yl-benzaldehyde

B: 4-Methoxy-6-morpholin-4-yl-benzene1,3-dicarbaldehyde

A solution of m-anisidine (11.2 mL, 0.1 mol), chloroethyl ether (11.7 mL, 0.1 mol), and diisopropylethylarine (35 mL, 0.2 mol) in toluene (100 mL) was stirred at reflux for 72 h. The precipitate was removed by filtration and washed with toluene (100 mL). The combined toluene solutions were concentrated in vacuo and purified by distillation (120–130° C., 0.2 Torr) to afford the intermediate 4-(3-methoxyphenyl)-morpholine (14.9 g, 77%).

DMF (10 mL) was treated dropwise with phosphorus oxychloride (1.3 g, 14 mmol). The reaction was kept at 25° C. bycooling on ice. The reaction mixture was treated with 4-(3-methoxyphenyl)-morpholine (2.5 g, 13 mmol) in small portions, stirred for 30 min at room temperature, then stirred at 100° C. for 4 h. After cooling, the mixture was poured into aqueous sodium acetate (1 M, 40 mL) and 25 mL of water was added. The resulting precipitate was collected by filtration, washed with water (10 mL), air dried, and purified by flash chromatography (silica gel, 4×15 cm, eluted with 80/20 CHCl$_3$/ether) to yield A and B as white solids: A: (1.0 g, 35%), B: (0.3 g, 9%).

A:

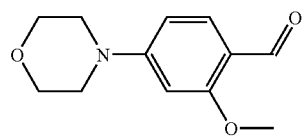

$^1$H NMR (90 MHz, CDCl$_3$): δ 10.21 (s, 1 H), 7.75 (d, J=8.6 Hz, 1 H), 6.48 (dd, J=8.6, 1.7 Hz, 1 H), 6.30 (s, 1 H), 3.90–3.80 (m, 7 H), 3.32 (t, J=4.9 Hz, 4 H). $^{13}$C NMR (75 MHz, CDCl$_3$): δ 187.5, 164.2, 156.1, 30.0, 117.5, 106.4, 96.0, 65.0, 54.9, 46.3.

IC$_{50}$ (nM) DNA-PK Assay—10,000.

B:

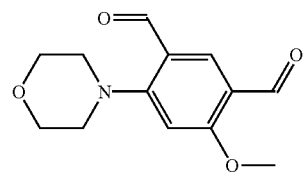

$^1$H NMR (90 MHz, CDCl$_3$): δ 10.26 (s, 1 H), 9.93 (s, 1 H), 8.27 (s, 1 H), 6.40 (s, 1 H), 3.99–3.88 (m, 7 H), 3.24 (t, J=4.6 Hz, 4 H). $^{13}$C NMR (75 MHz, CDCl$_3$): δ 188.2, 187.3, 166.1, 159.8, 137.7, 120.8, 119.3, 99.8, 66.2, 57.7, 52.5.

EXAMPLE 47

2-Hydroxy-5-morpholin-4-yl-benzoic acid methyl ester

Step 1: A solution of methyl 5-nitrosalicylate (10.0 g, 50.7 mmol) and imidazole (3.8 g, 55.8 mol) in DMF (50 mL) at 0° C. was treated with t-butyl-chloro-dimethyl-silane and stirred 16 h at room temperature. The reaction mixture was poured into water (100 mL) and extracted with ether (3×50 mL). The combined extracts were washed with water (4×100 mL) and brine (50 mL), dried over magnesium sulfate, and concentrated. The crude residue was purified by flash chromatography (silica gel, 4×15 cm, eluted with 95/5 hexanes/ EtOAc) to yield 2-(tert-butyl-dimethyl-silanyloxy)-5-nitrobenzoic acid methyl ester as a white solid (4.9 g, 31%).

Step 2: A solution of 2-(tert-butyl-dimethyl-silanyloxy)-5-Nitro-benzoic acid methyl ester (4.9 g, 16 mmol) in ethanol (100 mL) was treated with hydrogen gas (60 psi) for 48 h in the presence of palladium on carbon catalyst (0.31 g, 10% Pd). The catalyst was removed by filtration through CELITE®, and the filtrate was concentrated to a syrup and dried in vacuo to afford the intermediate 5-amino-2-(tert-butyl-dimethyl-silanyloxy)-benzoic acid methyl ester as a dark brown solid (4.52 g, 99%).

Step 3: A solution of 5-amino-2-(tert-butyl-dimethyl-silanyloxy)-benzoic acid methyl ester (4.5 g, 16 mmol), 2-chloroethyl ether (1.9 mL, 16.2 mmol), and diisopropylethylamine (5.6 mL, 32.1 mmol) in DMF (50 mL) was stirred at 100° C. for 48 h. The reaction mixture was poured into 10% aqueous NaHCO$_3$ (100 mL) and extracted with ether (200 mL). The organic layer was washed with water (5×100 mL) and brine (100 mL), dried over magnesium sulfate (MgSO$_4$), and concentrated to a red syrup. The residue was purified by flash chromatography (silica gel, 4×15 cm, eluted with 9/1 hexanes/EtOAc) to yield 2-(tert-butyl-dimethyl-silanyloxy)-5-morpholin-4-yl-benzoic acid methyl ester (1.0 g, 18%).

Step 4: A solution of 2-(tert-butyl-dimethyl-silanyloxy)-5-morpholin-4-yl-benzoic acid methyl ester (1.0 g, 2.8 mmol) in tetrahydrofuran (35 mL) was treated with tetrabutylammonium fluoride (3.55 g, 11.25 mmol) and stirred for 2 h at room temperature. The reaction mixture was concentrated and purified by flash chromatography (silica gel, 4×7.5 cm, eluted with 80/20 hexanes/EtOAc) to yield the final product as a yellow solid (206 mg, 31%).

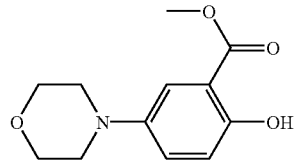

$^1$H NMR (300 MHz, CDCl$_3$): δ 10.40 (s, 1 H), 7.34 (d, J=2.7 Hz, 1 H), 7.16 (dd, J=9.0, 2.7 Hz, 1 H), 6.94 (d, J=9.0 Hz, 1 H), 3.95 (s, 3 H), 3.89–3.86 (m, 4 H), 3.08–3.05 (m, 4 H). $^{13}$C NMR (75 MHz, CDCl$_3$): δ 170.4, 156.3, 144.3, 126.2, 118.3, 116.4, 112.2, 67.0, 52.1, 50.9. LRMS (EI): m/z 237 (M$^+$), 205, 177, 147.

IC$_{50}$ (nM) DNA-PK Assay—40,000.

EXAMPLE 48

2-((Hydroxyimino)methyl)-5-morpholin-4-yl-phenol

A solution of 2-hydroxy-4-morpholin-4-yl-ben zaldehyde (0.135 g, 0.65 mmol) in pyridine (5 mL) was treated with hydroxylamine hydrochloride (45 mg, 0.65 mmol) and stirred for 30 min at room temperature. The reaction mixture was concentrated in vacuo and the residue was partitioned between EtOAc and 5% sodium bicarbonate. The organic layer was dried over Na$_2$SO$_4$ and concentrated in vacuo to afford the product as a pale yellow solid (51 mg, 35%).

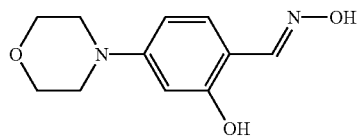

$^1$H NMR (90 MHz, CDCl$_3$) δ 8.04 (s, 1 H), 7.34 (s, 1 H), 6.97 (d, J=9.2 Hz, 1 H), 6.44–6.32 (m, 3 H), 3.76 (t, J=4.9 Hz, 4 H), 3.13 (t, J=4.9 Hz, 4 H).

IC$_{50}$ (nM) DNA-PK Assay—1,000.

EXAMPLE 49

2-Hydrazonomethyl-5-morpholin-4-yl-phenol

A solution of 2-hydroxy-4-morpholin-4-yl-benzaldehyde (0.135 g, 0.65 mmol) in pyridine (5 mL) was treated with hydrazine hydrate (33 mg, 0.65 mmol) and stirred for 3 h at room temperature. The reaction mixture was concentrated in vacuo and the residue was partitioned between EtOAc and 5% sodium bicarbonate. The organic layer was dried over Na$_2$SO$_4$ and concentrated in vacuo to afford the product as a pale yellow solid (96 mg, 67%)

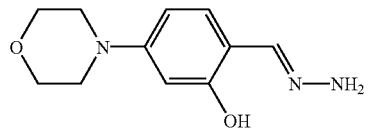

$^1$H NMR (90 MHz, CDCl$_3$) δ 7.80 (s, 1 H), 6.97 (d, J=9.3 Hz, 1 H), 6.44–6.32 (m, 3 H), 5.24 (br s, 2 H), 3.83 (t, J=4.9 Hz, 4 H), 3.18 (t, J=4.9 Hz, 4 H).

IC$_{50}$ (nM) DNA-PK Assay—1,000.

EXAMPLE 50

2-Hydroxy-4-((1-morpholin-4-yl-methanoyl)amino]-benzoic acid

A solution of 4-amino-2-hydroxy-benzoic acid methyl ester (1.0 g, 6 mmol) and triethylamine (0.8 mL, 6 mmol) in CHCl$_3$ (25 mL) was treated with morpholine-4-carbonyl chloride (4.2 mL, 48 mmol) and stirred at reflux for 72 h. After cooling to room temperature, the solution was washed with 5% aqueous hydrochloric acid (25 mL), saturated aqueous sodium bicarbonate (25 mL), and brine (25 mL), dried over Na$_2$SO$_4$, and concentrated to an orange solid. The crude solid was triturated with CHCl$_3$ (10 mL) to afford the product as an off-white solid (0.25 g, 15%).

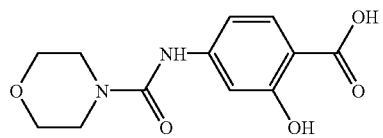

$^1$H NMR (300 MHz, d6-DMSO): δ 10.47 (s, 1 H), 8.17 (s, 1 H), 7.42 (d, J=8.8 Hz, 1 H), 6.90 (s, 1 H), 6.81 (dd, J=8.8, 1.7 Hz, 1 H), 3.62 (s, 3 H), 3.43 (t, J=4.5 H, 4 H), 3.27 (t, J=4.5 Hz, 4 H).

IC$_{50}$ (mM) DNA-PK Assay—100,000.

EXAMPLE 51

2-Hydroxy-4-morpholin-4-ylmethyl-benzoic acid methyl ester hydrochloride

Step 1: A solution of 4-methylsalicylic acid (75 g, 0.49 mmol) in MeOH (500 mL) at 0° C. was treated with dicyclohexylcarbodiimide (101 g, 0.49 mmol) and the mixture was stirred at room temperature for 2 h. The precipitated dicyclohexylurea was removed by filtration and the filtrate was concentrated in vacuo. The crude residue was purified by distillation (110° C. bath temp, 0.5 mm Hg) to afford 4-methylsalicylic acid methyl ester Step 2: A refluxing solution of 4-methylsalicylic acid methyl ester (5.1 g, 31.3 mmol) in carbon tetrachloride (50 mL) was treated dropwise with a solution of bromine (1.6 mL, 31.3 mmol) in carbon tetrachloride (5 mL) while under illumination by a 200 W incandescent light bulb. The reaction mixture was stirred for an additional 30 min at reflux and concentrated in vacuo. The residue was dissolved in EtOAc (50 mL) and washed with aqueous sodium thiosulfate (5%, 50 mL), water (50 mL), and brine (50 mL). The organic layer was dried over Na$_2$SO$_4$, concentrated, and the product 4-bromomethylsalicylic acid methyl ester was isolated by recrystallization from heptane (1.6 g, 21%).

Step 3: A solution of 4-bromomethylsalicylic acid methyl ester (245 mg, 1 mmol) and triethylamine (0.139 mL, 1 mmol) in acetonitmLe (5 mL) was treated with morpholine (0.087 mL, 1 mmol) and stirred at room temperature for 2 h. The reaction mixture was poured into saturated aqueous sodium bicarbonate (50 mL) and extracted with EtOAc (3×25 mL). The combined organic extracts were washed with water (25 mL) and brine (25 mL), dried with $Na_2SO_4$, and concentrated in vacuo. The residue was dissolved in ether (30 mL), cooled to 0° C., and treated with HCl gas. An equal volume of heptane was added and the crude solid product was collected by filtration, washed with heptane, and dried in vacuo. Half of the solid was purified by recrystallization from EtOAc/MeOH/heptane to yield the product 2-hydroxy-4-morpholin-4-yl-methyl-benzoic acid methyl ester hydrochloride (49 mg, 17%).

M.P.: 213–214° C.

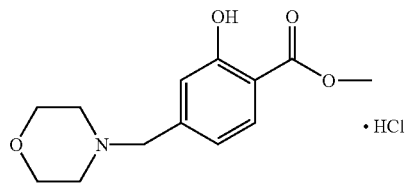

$^1$H NMR (300 MHz, d6-DMSO): δ 11.65 (bs, 1 H), 10.59 (s, 1 H), 7.82 (d, J=8.1 Hz, 1 H), 7.32 (s, 1 H), 7.22 (d, J=8.1 Hz, 1 H), 4.32 (d, J=5.1 Hz, 2 H), 3.95–3.70 (m, 4 H), 3.90 (s, 3 H), 3.25–3.00 (m, 4 H). $^{13}$C NMR (75 MHz, d6-DMSO): δ 168.6, 159.6, 136.8, 130.4, 122.2, 120.4, 114.2, 63.0, 58.1, 52.6, 50.8. Elemental analysis: Calc'd: C, 54.26; H, 6.31; N, 4.87%. Found: C, 54.19%; H, 6.20%; N, 4.65%.

$IC_{50}$ (nM) DNA-PK Assay—100,000.

EXAMPLE 52

2-Hydroxy-4-morpholin-4-ylmethyl-benzoic acid trifluoroacetate

A solution of 2-hydroxy-4-morpholin-4-ylmethyl-benzoic acid methyl ester hydrochloride (100 mg, 0.35 mmol) in MeOH (2 mL) was treated with 1 M sodium hydroxide (1.4 mL, 1.4 mmol) and stirred at 50° C. for 18 h. The reaction mixture was concentrated in vacuo to ¼ the original volume, treated with 1 M hydrochloric acid (0.7 mL, 6.7 mmol). The solution was purified by HPLC on a 2.1×25 cm Vydac C18 Protein and Peptide column, 20 mL/min, with a gradient as follows (0–5 min: 100% water, 25 min: 30% acetonitrile/ 70% water. Both solvents contained 0.05% trifluoroacetic acid). The product fractions were combined and lyophilized to a white powder.

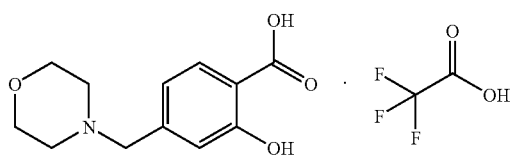

M.P.: 138–146° C. $^1$H NMR (300 MHz, d6-DMSO) δ 7.87 (d, J=8.0 Hz, 1 H), 7.11 (bs, 1 H), 7.03 (dd, J=8.0Hz, 1 H), 4.30 (s, 2 H), 3.78 (bs, 4 H), 3.15 (bs, 4 H). Elemental analysis: Calc'd for $C_{12}H_{15}NO_4 \cdot 1.1\ C_2HF_3O_2$: C, 47.03; H, 4.47%; N, 3.86%. Found: C, 47.03%; H, 4.37%; N, 3.87%.

$IC_{50}$ (nM) DNA-PK Assay—100,000.

EXAMPLE 53

2-Hydroxy-4-morpholin-4-ylmethyl benzoic acid hydrochloride

A solution of 2-hydroxy-4-morpholin-4-ylmethyl-benzoic acid methyl ester hydrochloride (75 mg, 0.26 mmol) in MeOH (0.5 mL) was treated with ammonium hydroxide (1 mL) and stirred in a sealed vial for 2 h at 60° C. After cooling, the reaction mixture was concentrated under a stream of nitrogen to approximately ¼ the original volume and was treated with 1 M HCl (0.25 mL, 0.25 mmol). The solid that formed was collected by filtration and recrystallized from water to yield the white crystalline product.

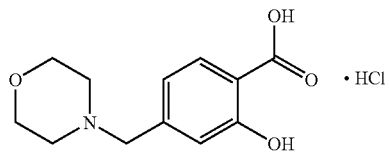

$^1$H NMR (300 MHz, d6-DMSO: δ 13.21 (s, 1 H), 10.95 (br s, 1 H), 8.51 (s, 1 H), 8.05 (s, 1 H), 7.92 (d, J=8.1 Hz, 1 H), 7.18–7.01 (m, 3 H), 4.28 (s, 2 H), 3.95–3.72 (m, 4 H), 3.25–3.06 (m, 4 H). Elemental analysis: Calc'd for $C_{12}H_{16}N_2O_3 \cdot HCl$: C, 52.85; H, 6.28%; N, 10.27%. Found: C, 52.47%; H, 6.16%; N, 10.10%.

$IC_{50}$ (nM) DNA-PK Assay—100,000.

EXAMPLE 54

4-Amino-2-hydroxy-benzoic acid methyl ester

Esterification Procedure:

To a stirred solution of 4-amino salicylic acid (110.0 g; 718 mmol) in dry MeOH (3025 mL) was slowly added concentrated sulfuric acid (187 mL; 3.5 mmol) via pipette at room temperature under nitrogen atmosphere. The resulting solution was heated to reflux for 20 hours then allowed to cool to room temperature. The reaction was concentrated at reduced pressure to about ¼ the original volume, then neutralized by the careful addition of saturated aqueous sodium bicarbonate to pH 7–8. The resulting precipitate was collected on a Buchner funnel with suction, washed with water, and allowed to air dry. The resulting gray solid was dissolved in EtOAc (1.5 L) and treated with decolorizing charcoal. Filtration and recrystallization (EtOAc/hexanes or MeOH/water (1:3)) provided the ester as an off white crystal (94.5 g; 79%).

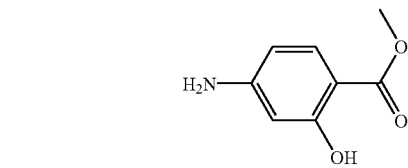

¹H NMR (CDCl₃, 400 MHz): δ 10.95 (s, 1H), 7.59 (dd, 1H), 6.14 (s, 1H), 6.12 (d, 1H), 4.16 (br s, 2H), 3.85 (s, 3H).

EXAMPLE 55

2-Hydroxy-4-morpholin-4-yl-benzoic acid methyl ester

Morpholine Cyclization Procedure:

A stirred suspension of free aniline (50.0 g; 299 mmol), Hunig's base (104.3 mL; 598 mmol), chloro-ethyl ether (35.1 mL; 299 mmol) and sodium iodide (89.75 g; 598 mmol) in dry toluene (450 mL) was heated to reflux under a nitrogen atmosphere for 5 days. After cooling to room temperature, the reaction was quenched with cold aqueous citric acid (10%) and extracted with EtOAc (3×500 mL). Combined organic extracts were washed with 5% aqueous sodium bicarbonate and brine then dried (Na₂SO₄), decolorized (activated charcoal), filtered and concentrated in vacuo. The residue was purified via flash chromatography (5:1 hexanes/EtOAc on silica gel) to provide the morpholine as a white crystalline product (26.0 g; 37%).

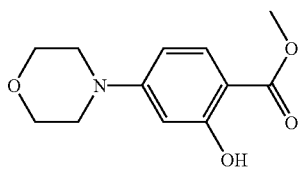

¹H NMR (CDCl₃, 400 MHz): δ 10.86 (s, 1H), 7.65 (d, 1H), 6.36 (dd, 1H), 6.31 (d, 1H), 3.87 (s, 3H), 3.79 (t, 4H), 3.25 (t, 4H).

EXAMPLE 56

2-Hydroxy-N-methyl-4-morpholin-4-yl-benzamide

Weinreb Amidation Procedure:

To a cooled (0° C.), stirred solution of methylamine in dry tetrahydrofuran (1.27 mL of 2.0 M solution; 2.52 mmol) was slowly added a solution of trimethylaluminum in dry toluene (1.27 mL of 2.0 M solution; 2.52 mmol) via syringe under a nitrogen atmosphere. The resulting solution was allowed to warm to room temperature and stir for 2 hours. To the resulting solution, a solution of the 2-hydroxy-4-morpholin-4-yl-benzoic acid methyl ester (100 mg; 0.42 mmol) in dry toluene (4.0 mL) was added via cannula and the resulting solution was heated to reflux for 2 hours. After cooling to room temperature, the reaction was quenched with the careful addition of 1 N aqueous hydrochloric acid to pH 4. The mixture then was extracted with EtOAc (3×10 mL), and the combined organic layers washed with brine, dried (Na₂SO₄), filtered and concentrated in vacuo. The residue was recrystallized from CH₂Cl₂—hexanes to provide the amide (93 mg; 93%).

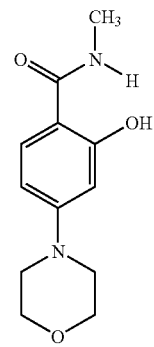

¹NMR (CDCl₃, 400 MHz, mixture of rotomers): δ 12.60 (s, 1H), 7.20 (d, 1H), 6.38–6.33 (m, 2H), 6.14 (br s, 1H), 3.82 (t, 4H), 3.23 (t, 4H), 2.97 (d, 3H). LRMS (Electrospray, negative): Da/e 235.2 (m−1).

EXAMPLE 57

1-(2-Hydroxy-4-morpholin-4-yl-phenyl)-1-morpholin-4-yl-methanone

Prepared via the Weinreb amidation procedure of Example 56.

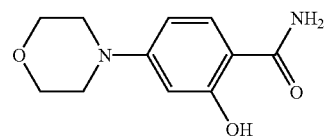

¹H NMR (CDCl₃, 400 MHz): δ 10.45 (s, 1H), 7.14 (d, 1H), 6.42 (d, 1H), 6.35 (dd, 1H), 3.83 (t, 4H), 3.73 (s, 8H), 3.23 (t, 4H). LRMS (Electrospray, negative): Da/e 291.3 (m−1).

EXAMPLE 58

2-Hydroxy-4-morpholin-4-yl-benzamide

Prepared via the Weinreb amidation procedure of Example 56.

¹H NMR (CDCl₃, 400 MHz): δ 7.33 (d, 1H), 6.45 (dd, 1H), 6.37 (d, 1H), 6.15 (br s, 2H), 3.83 (t, 4H), 3.26 (t, 4H). LRMS (Electrospray, positive): Da/e 223.3 (m+1).

EXAMPLE 59

2-Hydroxy-4-morpholin-4-yl-N-benzyl-benzamide

Prepared via the Weinreb amidation procedure of Example 56.

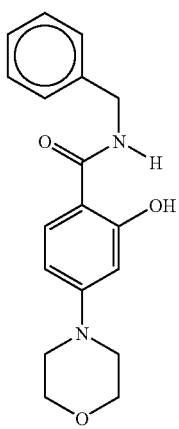

$^1$H NMR (CDCl$_3$, 400 MHz): δ 12.55 (d, 1H), 7.39–7.27 (m, 5H), 7.20 (d, 1H), 6.38 (d, 1H), 6.34 (dd, 1H), 6.31 (br s, 1H), 4.62 (d, 2H), 3.82 (t, 4H), 3.24 (t, 4H). LRMS (Electrospray, negative): Da/e 311.4 (m−1).

EXAMPLE 60

2-Hydroxy-4-morpholin-4-yl-N-phenyl-benzamide

Prepared via the Weinreb amidation procedure of Example 56.

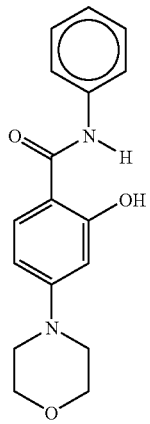

$^1$H NMR (d6-DMSO, 400 MHz): δ 12.41 (s, 1H), 10.10 (s, 1H), 7.92 (d, 1H), 7.67 (d, 2H), 7.34 (t, 2H), 7.10 (t, 1H), 6.56 (dd, 1H), 6.35 (d, 1H), 3.70 (t, 4H), 3.22 (t, 4H). LRMS (Electrospray, negative): Da/e 297.3 (m−1).

EXAMPLE 61

N-Cyclopropyl-2-hydroxy-4-morpholin-4-yl-N-phenyl-benzamide

Prepared via the Weinreb amidation procedure of Example 56.

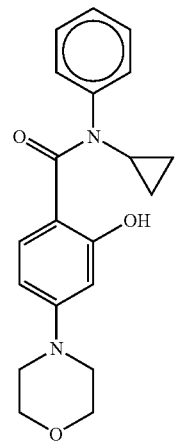

$^1$H NMR (CDCl$_3$, 400 MHz): δ 12.55 (s, 1H), 7.13 (d, 1H), 6.36–6.32 (m, 2H), 6.18 (br s, 1H), 3.82 (t, 4H), 3.23 (t, 4H), 2.84 (c, 1H), 0.92–0.83 (m, 2H), 0.65–0.60 (m, 2H). LRMS (Electrospray, negative): Da/e 261.4 (m−1).

EXAMPLE 62

2-Hydroxy-4-morpholin-4-yl-N-(2-methoxyethyl)-benzamide

Prepared via the Weinreb amidation procedure of Example 56.

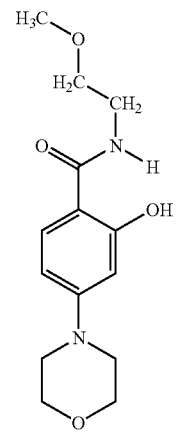

$^1$H NMR (CDCl$_3$, 400 MHz): δ 12.56 (s, 1H), 7.22 (br s, 1H), 6.45–6.31 (m, 2H), 3.82 (t, 4H), 3.60 (t, 2H), 3.55 (t, 2H), 3.39 (d, 3H), 3.24 (t, 4H). LRMS (Electrospray, negative): Da/e 279.4 (m−1).

EXAMPLE 63

2-Hydroxy-4-morpholin-4-yl-N-methoxy-N-methyl-benzamide

Prepared via the Weinreb amidation procedure of Example 56.

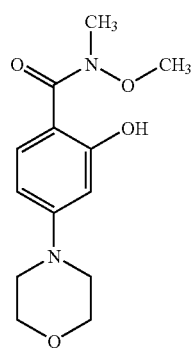

¹H NMR (CDCl₃, 400 MHz): δ 12.06 (s, 1H), 7.95 (dd, 1H), 6.39–6.34 (m, 2H), 3.83 (t, 4H), 3.66 (s, 3H), 3.37 (s, 3H), 3.27 (t, 4H). LRMS (Electrospray, negative): Da/e 265.3 (m−1).

EXAMPLE 64

2-Hydroxy-4-morpholin-4-yl-N-(3-dimethylamino-propyl)-benzamide

Prepared via the Weinreb amidation procedure of Example 56.

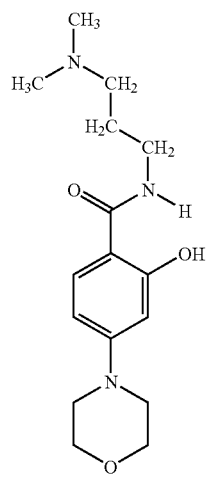

¹H NMR (CDCl₃, 400 MHz,): δ 8.89 (s, 1H), 7.13 (d, 1H), 6.37–6.34 (m, 2H), 3.82 (t, 4H), 3.52 (t, 2H), 3.22 (dd, 4H), 2.52 (t, 2H), 2.31 (s, 6H), 1.76 (c, 2H). LRMS (Electrospray, negative): Da/e 306.3 (m−1).

EXAMPLE 65

2-Hydroxy-4-morpholin-4-yl-N-methoxy-benzamide

Prepared via the Weinreb amidation procedure of Example 56.

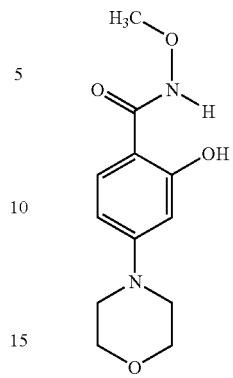

¹H NMR (CDCl₃, 400 MHz): δ 11.80 (s, 1H), 8.82 (s, 1H), 7.18 (d, 1H), 6.35 (br s, 1H), 6.32 (d, 1H), 3.85 (s, 3H), 3.82 (t, 4H), 3.24 (t, 4H). LRMS (Electrospray, negative): Da/e 251.0 (m−1).

EXAMPLE 66

2-Hydroxy-4-morpholin-4-yl-N-(2-methanesulfonyl-ethyl)-benzamide

Prepared via the Weinreb amidation procedure of Example 56.

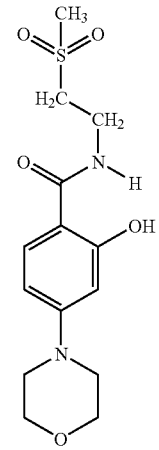

¹H NMR (CDCl₃, 400 MHz): δ 12.28 (s, 1H), 7.25 (d, 1H), 6.98 (t, 1H), 6.37 (d, 1H), 6.34 (t, 1H), 3.96 (q, 2H), 3.82 (t, 4H), 3.33 (t, 2H), 3.24 (t, 4H), 2.99 (s, 3H). LRMS (Electrospray, negative): Da/e 327.1 (m−1).

EXAMPLE 67

2-Hydroxy-4-morpholin-4-yl-N-pyridin-3-yl-benzamide

Prepared via the Weinreb amidation procedure of Example 56.

¹H NMR (d6-DMSO, 400 MHz): δ 12.21 (s, 1H), 10.24 (s, 1H), 8.83 (s, 1H), 8.30 (d, 1H), 8.09 (d, 1H), 7.89 (d, 1H), 7.37 (dd, 1H), 6.58 (d, 1H), 6.35 (s, 1H), 3.70 (d, 4H), 3.23 (d, 4H). LRMS (Electrospray, negative): Da/e 298.4 (m−1).

EXAMPLE 68

2-Hydroxy-4-morpholin-4-yl-N-pyridin-4-yl-benzamide

Prepared via the Weinreb amidation procedure of Example 56.

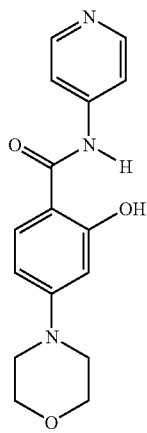

¹H NMR (d6-Acetone, 400 MHz): δ 9.71 (s, 1H), 8.48 (dd, 1H), 7.85 (d, 1H), 7.75 (dd, 2H), 6.56 (dd, 1H), 6.38 (d, 1H), 3.76 (t, 4H), 3.30 (t, 4H). LRMS (Electrospray, negative): Da/e 298.5 (m−1). LRMS (Electrospray, positive): Da/e 300.3 (m+1).

EXAMPLE 69

2-Hydroxy-4-morpholin-4-yl-N-thiazol-2-yl-benzamide

Prepared via the Weinreb amidation procedure of Example 56.

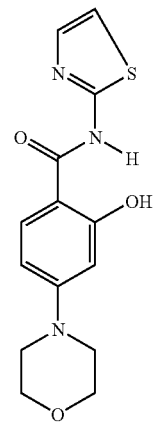

¹H NMR (d6-DMSO, 400 MHz): δ 7.93 (d, 1H), 7.51 (d, 1H), 7.23 (br s, 1H), 6.60 (dd, 1H), 6.39 (d, 1H), 3.72 (t, 4H), 3.25 (t, 4H). LRMS (Electrospray, negative): Da/e 304.1 (m−1).

EXAMPLE 70

2-Hydroxy-4-morpholin-4-yl-N-(1,4-thiazin-2-yl)-benzamide

Prepared via the Weinreb amidation procedure of Example 56.

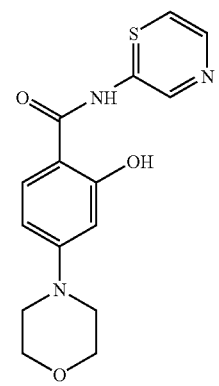

¹H NMR (d6-Acetone, 400 MHz), δ 12.33 (s, 1H), 10.88 (s, 1H), 7.52–7.37 (m, 6H), 6.48–6.34 (m, 2H), 5.00 (s, 2H), 3.75 (t, 4H), 3.25 (t, 4H). LRMS (Electrospray, negative): Da/e 327.1 (m−1).

EXAMPLE 71

2,N-Dihydroxy-4-morpholin-4-yl-benzamide

Hydrogenation Procedure:
To a stirred solution of o-benzyl hydroxamate (80 mg; 0.24 mmol) in dry MeOH (3 mL) and dry tetrahydrofuiran (3 mL) was carefully added 10% palladium on carbon (6 mg; cat.) under nitrogen atmosphere at room temperature. The resulting mixture was purged on nitrogen and placed under an atmosphere of hydrogen (balloon pressure) and allowed to stir for 1.5 hours. The reaction was then carefully filtered through GF/F paper with suction (nitrogen blanket) and washed with CH₂Cl₂. The filtrate then was concentrated in vacuo and the residue recrystallized from acetone/toluene to provide the hydroxamic acid as an off-white solid (38 mg; 66%).

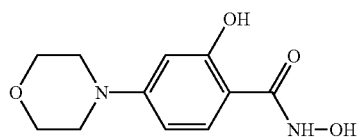

¹H NMR (d6-Acetone, 400 MHz): δ 12.28 (br s, 1H), 10.69 (br s, 1H), 8.29 (br s, 1H), 7.54 (dd, 1H), 6.48 (dt, 1H), 6.34 (t, 1H), 3.76 (t, 4H), 3.24 (t, 4H). LRMS (Electrospray, negative): Da/e 237.0 (m−1).

EXAMPLE 72

2-Hydroxy-4-morpholin-4-yl-N-(4-pyridylmethyl)-benzamide

Prepared via the Weinreb amidation procedure of Example 56.

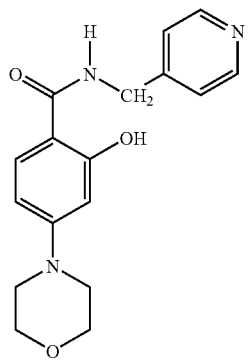

¹NMR (d4-MeOH, 400 MHz): δ 8.46 (dd, 2H), 7.65 (d, 1H), 7.38 (dd, 2H), 6.50 (dd, 1H), 6.35 (d, 1H), 4.88 (s, 2H), 3.79 (t, 4H), 3.23 (t, 4H). LRMS (Electrospray, positive): Da/e 314.4. (m+1). LRMS (Electrospray, negative): Da/e 312.3 (m−1).

EXAMPLE 73

1-(2-Hydroxy-4-morpholin-4-yl-phenyl)-1-(4-phenylpiperizin-1-yl)-methanone

Prepared via the Weinreb amidation procedure of Example 56.

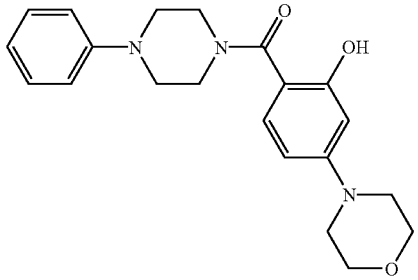

¹H NMR (d6-DMSO, 400 MHz): δ 9.80 (s, 1H), 7.24 (dd, 2H), 7.08 (d, 1H), 6.97 (d, 2H), 6.82 (t, 1H), 6.49 (dd, 1H), 6.38 (d, 1H), 3.74 (t, 4H), 3.59 (br s, 4H), 3.17–3.10 (m, 8H). LRMS (Electrospray, positive): Da/e 368.3 (m+1). LRMS (Electrospray, negative): Dale 366.3 (m−1).

Example 74

2-Hydroxy-4-morpholin-4-yl-benzoic acid

Hydrolysis Procedure:

To a stirred solution of 2-hydroxy-4-morpholin-4-yl-benzoic acid methyl ester (4.6 g; 19.4 mmol) in MeOH (120 mL) was added water (60 mL) and lithium hydroxide hydrate (4.08 g; 97 mmol). The resulting mixture was heated to 80° C. for 15 hours. The resulting mixture then was washed with EtOAc (3×60 mL), and cooled to 0° C. and acidified with 2 N aqueous hydrochloric acid to pH 4. The resulting precipitate was collected on a Buchner funnel with suction, washed with water, and air dried to provide the acid (4.16 g; 96%).

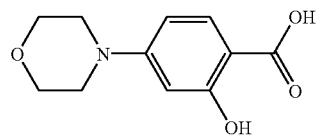

¹H NMR (d6-DMSO, 400 MHz): δ 13.21 (br s, 1H), 11.37 (br s, 1H), 7.56 (d, 1H), 6.48 (dd, 1H), 6.32 (d, 1H), 3.68 (t, 4H), 3.23 (t, 4H).

Example 75

N-(Carboxymethyl-2-hydroxy-4-morpholin-4-yl-phenyl)-carboxamide methyl ester

EDC Coupling Procedure:

To a stirred mixture of 2-hydroxy-4-morpholin-4-ylbenzoic acid (300 mg; 1.34 mmol) in CH₂Cl₂ (4 mL) and tetrahydrofuran (4 mL) was added glycine methyl ester hydrochloride (676 mg; 5.36 mmol), 1-(3-dimethylaminopropyl)-3-ethylcarbodiimide hydrochloride (258 mg; 1.34 mmol), and Hunig's base (0.937 mL; 5.36 mmol) at room temperature under a nitrogen atmosphere. The resulting solution was allowed to stir at room temperature for 24 hours, then concentrated at reduced pressure and re-dissolved in EtOAc (30 mL). The resulting solution was washed with water (3×10 mL), 10% aqueous citric acid, 5% aqueous NaHCO₃ and brine, then dried (Na₂SO₄), filtered and concentrated in vacuo. The residue was recrystallized from EtOAc/hexanes to provide the amide as a white solid (79%).

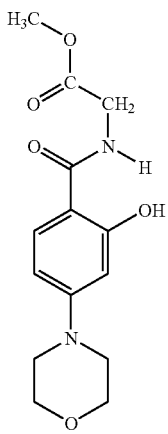

¹H NMR (d6-Actone, 400 MHz): δ 12.62 (s, 1H), 8.18 (br s, 1H), 7.66 (d, 1H), 6.52 (dd, 1H), 6.34 (d, 1H), 4.13 (d, 2H), 3.78 (t, 4H), 3.71 (s, 3H), 3.27 (t, 4H). LRMS (Electrospray, negative): Da/e 293.1 (m−1).

Example 76

N-Carboxymethyl-2-hydroxy-4-morpholin-4-yl-phenyl-carboxamide

Prepared via the hydrolysis procedure of Example 74.

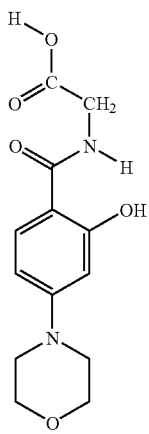

¹H NMR (d4-MeOH, 400 MHz): δ 7.63 (d, 1H), 6.50 (dd, 1H), 6.34 (d, 1H), 4.88 (s, 2H), 3.80 (t, 4H), 3.23 (t, 4H). LRMS (Electrospray, negative): Da/e 279.0 (m−1).

Example 77

2-Hydroxy-4-morpholin-4-yl-thiobenzamide

To a stirred solution of 2-hydroxy-4-morpholin-4-yl-benzamide (102 mg; 0.46 mmol) and t-butyldimethylsilyl chloride (73 mg; 0.48 mmol) in dry tetrahydrofuran (4 mL) was added Hunig's base (0.084 mL; 0.48 mmol) via syringe at room temperature under a nitrogen atmosphere. After stirring at room temperature for 4 hours, Lawesson's reagent was added (117 mg; 0.28 mmol) in one portion and the resulting solution was stirred for 16 hours. Benzyl trimethyl ammonium fluoride (1.84 mmol) then was added and stirring was continued for 2 hours longer. The reaction was concentrated at reduced pressure, and the residue re-dissolved in EtOAc (10 mL) and washed with water, 10% citric acid, 5% NaHCO₃, and brine then dried (Na₂SO₄), filtered and concentrated in vacuo. The residue was then recrystallized from EtOAc/hexanes to provide the thioamide as a yellow solid (31 mg; 28%).

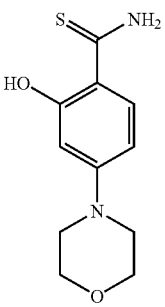

¹H NMR (d6-Acetone, 400 MHz): δ 12.65 (br s, 1H), 8.73 (br s, 1H), 8.50 (br s, 1H), 7.72 (d, 1H), 6.51 (dd, 1H), 6.35 (d, 1H), 3.77 (t, 4H), 3.30 (t, 4H). LRMS (Electrospray, positive): Da/e 239.2 (m+1).

Example 78

2-(4-Ethylphenyl)-4-imino-7-morpholin-4-yl-benzo[e]-1,3,2-oxathiaphosphane-2-thione To a stirred solution of 2-hydroxy-4-morpholin-4-yl-benzamide (0.53 g; 2.4 mmol) in dry toluene (20 mL) was added Lawesson's reagent (0.58 g; 1.44 mmol) and the resulting mixture was heated to 100° C. for 0.5 h under a nitrogen atmosphere. The resulting yellow mixture was allowed to cool to room temperature and was concentrated at reduced pressure and the residue purified via flash chromatography (1:1 hexanes/EtOAc on silica gel) to provide the heterocycle as a bright yellow solid (0.79 g; 99%).

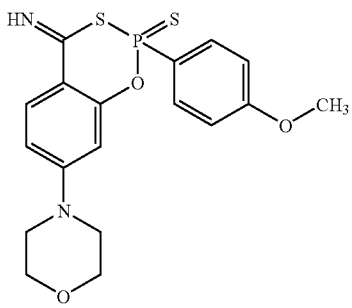

$^1$H NMR (CDCl$_3$, 400 Mz): δ 8.35 (d, 1H), 8.21 (br d, 1H), 7.84 (dd, 2H), 6.95 (dd, 2H), 6.66 (dd, 1H), 6.35 (d, 1H), 3.85 (s, 3H), 3.82 (t, 4H), 3.33 (t, 4H). LRMS (Electrospray, positive): Da/e 405.1 (m+1).

Example 79

1-(2-Hydroxy-4-morpholin-4-yl-phenyl)-1-phenyl-methanone

Ketone Procedure

To a stirred, cooled (−78° C.) solution of bromobenzene (0.475 mL; 4.5 mmol) in dry tetrahydrofuran (10 mL) was added n-butyllithium (1.8 mL of 2.5 M in hexanes; 4.5 mmol) via syringe under nitrogen atmosphere. After stirring for 0.5 h at −78° C., the resulting solution was treated with a solution of the N-methyl-N-methoxy-(2-hydroxy-4-morpholin-4ylphenyl)-carboxamide (0.30 g; 1.13 mmol) in dry tetrahydrofuran (2 mL) via carinula. After stirring at −78° C. for 3 hours, the reaction was quenched with the addition of 10% aqueous citric acid. After warming to room temperature, the tetrahydrofuran was removed at reduced pressure and the residue extracted with EtOAc (3×15 mL). Combined organic layers were washed with water and brine, then dried (Na$_2$SO$_4$), filtered and concentrated in vacuo. Purification of the residue via flash chromatography (10:1 hexanes/EtOAc on silica gel) provided the ketone as a light yellow crystalline solid (0.213 g; 70%).

$^1$H NMR (CDCl$_3$, 400 MHz): δ 12.74 (s, 1H), 7.62 (d, 2H), 7.55–7.43 (m, 4H), 6.37 (d, 1H), 6.33 (dd, 1H), 3.82 (t, 4H), 3.35 (t, 4H). $^{13}$C NMR (CDCl$_3$, 100 MHz): δ 199.0, 166.1, 156.6, 138.8, 135.4, 131.3, 129.0, 128.4, 111.3, 105.3, 100.6, 66.7, 47.2.

Example 80

1-(2-Hydroxy-4-morpholin-4-yl-phenyl)-1-(4-trifluoromethylphenyl)-methanone

Prepared via the ketone procedure of Example 79.

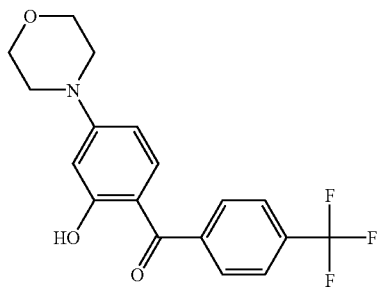

$^1$H NMR (CDCl$_3$, 400 MHz): δ 12.56 (s, 1H), 7.73 (q, 4H), 7.32 (d, 1H), 6.37 (d, 1H), 6.33 (dd, 1H), 3.83 (t, 4H), 3.37 (t, 4H). $^{13}$C NMR (CDCl$_3$, 100 MHz): δ 197.2, 166.1, 156.8, 141.9, 135.0, 128.0, 125.4 (q), 110.9, 105.5, 100.4, 66.7, 47.1. LRMS (Electrospray, negative): Da/e 350.3 (m−1).

EXAMPLE 81

1-(2-Hydroxy-4-morpholin-4-yl-phenyl)-1-(o-tolyl)-methanone

Prepared via the ketone procedure of Example 79.

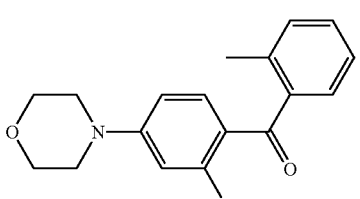

$^1$H NMR (CDCl$_3$, 400 MHz): δ 12.79 (s, 1H), 7.38–7.31 (c, 1H), 7.28–7.22 (m, 3H), 7.10 (d, 1H), 6.35 (d, 1H), 6.26 (dd, 1H), 3.81 (t, 4H), 3.34 (t, 4H), 2.29 (s, 3H). $^{13}$C NMR (CDCl$_3$, 100 MHz): δ 201.1, 165.8, 156.8, 138.5, 135.4, 135.3, 130.8, 129.7, 127.4, 125.4, 112.2, 105.4, 100.3, 66.7, 47.2, 30.1, 19.9. LRMS (Electrospray, positive): Da/e 298.2 (m+1).

EXAMPLE 82

1-(2-Hydroxy-4-morpholin-4-yl-phenyl)-1-(4-methoxyphenyl)-methanone

Prepared via the ketone procedure of Example 79.

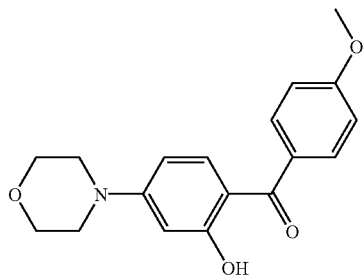

$^1$H NMR (CDCl$_3$, 400 MHz): δ 12.75 (s, 1H), 7.65 (d, 2H), 7.50 (d, 1H), 6.98 (d, 2H), 6.38 (d, 1H), 6.35 (dd, 1H), 3,88 (s, 3H), 3.83 (t, 4H), 3.35 (t, 4H).

$^{13}$C NMR (CDCl$_3$, 100 MHz): δ 197.9, 165.8, 162.4, 156.4, 135.2, 131.4, 131.2, 113.8, 111.5, 105.2, 100.8, 66.8, 55.8, 47.3. LRMS (Electrospray, negative): Da/e 312.2 (m−1).

EXAMPLE 83

1-(2-Hydroxy-4-morpholin-4-yl-phenyl)-1-pyridin-3-yl-methanone

Prepared via the ketone procedure of Example 79.

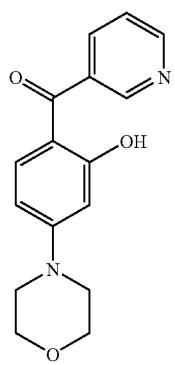

$^1$H NMR (CDCl$_3$, 400 MHz): δ 12.56 (s, 1H), 8.86 (dd, 1H), 8.77 (dd, 1H), 7.95 (dt, 1H), 7.44 (ddd, 1H), 7.37 (d, 1H), 6.37 (t, 1H), 6.34 (d, 1H), 3.84 (t, 4H), 3.38 (t, 4H). $^{13}$C NMR (CDCl$_3$, 100 MHz): δ 196.0, 166.1, 15 6.8, 151.9, 149.6, 136.4, 134.9, 134.4, 123.5, 111.1, 105.6, 100.4, 66.7, 47.1. LRMS (Electrospray, negative): Da/e 283.7 (m−1). LRMS (Electrospray, positive): Da/e 285.3 (m+1).

EXAMPLE 84

1-(2-Hydroxy-4-morpholin-4-yl-phenyl)-pentan-1-one

Prepared via the ketone procedure of Example 79.

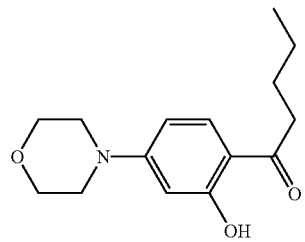

$^1$H NMR (CDCl$_3$, 400 MHz): δ 12.88 (s, 1H), 7.60 (d, 1H), 6.37 (dd, 1H), 6.28 (d, 1H), 3.82 (t, 4H), 3.31 (t, 4H), 2.85 (t, 2H), 1.70 (p, 2H), 1.40 (h, 2H), 0.94 (t, 3H). $^{13}$C NMR (CDCl$_3$, 100 MHz): δ 204.4, 165.1, 156,5, 131.8, 111.8, 105.5, 100.8, 66.8, 47.3, 37.7, 27.6, 22.9, 14.3. LRMS (Electrospray, negative): Da/e 262.3 (m−1).

EXAMPLE 85

1-(2-Hydroxy-4-morpholin-4-yl-phenyl)-2-phenyl-ethanone

Prepared via the ketone procedure of Example 79.

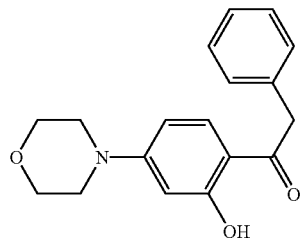

$^1$H NMR (CDCl$_3$, 400 MHz): δ 12.72 (s, 1H), 7.69 (d, 1H), 7.35–7.24 (m, 5H), 6.37 (dd, 1H), 6.27 (d, 1H), 4.17 (s, 2H), 3.81 (t, 4H), 3.31 (t, 4H). $^{13}$C NMR (CDCl$_3$, 100 MHz). δ 200.9, 165.5, 156,6, 135.1, 132.3, 129.5, 128.9, 127.1, 111.4, 105.7, 100.6, 66.7, 47.2, 44.9.

EXAMPLE 86

1-(2-Hydroxy-4-morpholin-4-yl-phenyl)-1-thiophen-2-yl-methanone

Prepared via the ketone procedure of Example 79.

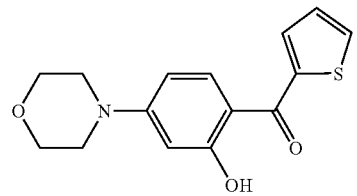

¹H NMR (CDCl₃, 400 MHz): δ 12.49 (s, 1H), 7.86 (d, 1H), 7.66 (d, 2H), 7.17 (t, 1H), 6.42 (dd, 1H), 6.37 (d, 1H), 3.84 (t, 4H), 3.37 (t, 4H). ¹³C NMR (CDCl₃, 100 MHz): δ 188.7, 165.6, 156.4, 142.7, 133.8, 132.9, 132.4, 127.7, 111.3, 105.6, 100.8, 66.8, 47.2. LRMS (Electrospray, positive): Da/e 290.2 (m+1).

EXAMPLE 87

1-(2-Hydroxy-4-morpholin-4-yl-phenyl)-1,3-thiazol-2-yl-methanone

Prepared via the ketone procedure of Example 79.

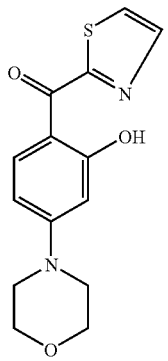

¹H NMR (CDCl₃, 400 MHz): δ 12.74 (s, 1H), 8.97 (d, 1H), 8.19 (q, 2H), 6.64 (dd, 1H), 6.35 (d, 1H), 3.69 (t, 4H), 3.41 (t, 4H). ¹³C NMR (d6-DMSO, 100 MHz): δ 182.3, 168.7, 167.0, 157.3, 145.7, 135.5, 127.9, 108.9, 107.0, 99.4, 66.5, 46.9. LRMS (Electrospray, positive): Da/e 291.2 (m+1).

EXAMPLE 88

1-(3-Chlorophenyl)-1-(2-hydroxy-4-morpholin-4-yl-phenyl)-methanone

Prepared via the ketone procedure of Example 79.

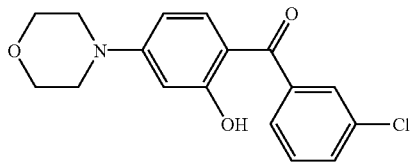

¹H NMR (CDCl₃, 400 MHz): δ 12.56 (s, 1H), 7.59 (t, 1H), 7.52–7.48 (m, 2H), 7.42 (d, 1H), 7.37 (d, 1H), 6.36 (t, 1H), 6.33 (d, 1H), 3.83 (t, 4H), 3.36 (t, 4H). ¹³C NMR (CDCl₃, 100 MHz): δ 197.1, 166.1, 156.8, 140.4, 135.1, 134.6, 131.3, 129.8, 128.7, 127.0, 111.0, 105.5, 100.5, 66.7, 47.1. LRMS (Electrospray, positive): Da/e 318.3 (m+1).

EXAMPLE 89

2-Chloro-1-(2-hydroxy-4-morpholin-4-yl-phenyl)-ethanone

Sugasawa Procedure

An oven-dried, 500-mL 3-necked round-bottom flask equipped with mechanical stirrer, condenser with a nitrogen inlet and dropping funnel with rubber septum was charged with 5.0 g (27.8 mmol) of 3-morpholinylphenol, 2.1 mL (33.8 mmol) chloroacetonitrile, and 150 mL of dichloroethane, and the mixture chilled in an ice bath. The dropping funnel was charged with 100 mL (100 mmol) of 1.0 M boron trichloride in CH₂Cl₂ and this was added dropwise with vigorous stirring. When the addition was completed 1.9 g (14 mmol) of aluminum trichloride was added in one portion. The reaction then was heated at 60° C. for 18 h. The reaction then was chilled (0° C.). The dropping funnel was charged with 100 mL of 2 N aqueous hydrochloric acid, which was added dropwise forming a solid. When the addition was complete, the reaction was heated at 60° C. for 1 h which dissolved most of the solids. The reaction was cooled, and the organic layer separated and washed with 2 N HCl (2×40 mL), water (40 mL), and brine (40 mL). The organic layer then was dried (MgSO₄), filtered and concentrated in vacuo to give 1.8 g (25.5%) of the desired chloroketone as a yellowish green solid.

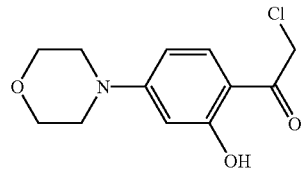

¹H NMR (CDCl₃, 400 MHz): δ 12.16 (s, 1H), 7.53 m (d, 1H), 6.39 (dd, 1H), 6.29 (d, 1H), 4.56 (d, 2H), 3.82 (t, 4H), 3.36 (t, 4H).

EXAMPLE 90

1-(2-Hydroxy-4-morpholin-4-yl-phenyl)-2-morpholin-4-yl-ethanone

Amination Procedure:

To a stirred solution of 2-chloro-1-(2-hydroxy-4-morpholin-4-yl-phenyl)-ethanone (95 mg; 0.37 mmol) in dry acetonitrile (3 mL) was added powdered K₂CO₃ (77 mg; 0.56 mmol) and morpholine (0.034 mL; 0.39 mmol) at room temperature under a nitrogen atmosphere. The resulting mixture was heated to reflux for 0.5 hour, then allowed to cool to room temperature. The reaction was diluted with CH₂Cl₂ (50 mL), filtered, and concentrated in vacuo. The residue was purified by radial chromatography (2 mm chromatotron plate with 2% MeOH in CH₂Cl₂) to provide the amine as a clear, colorless oil (87 mg; 77%).

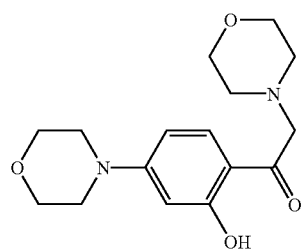

¹H NMR (CDCl₃, 400 MHz): δ 12.68 (br s, 1H), 7.72 (d, 1H), 6.33 (dd, 1H), 6.22 (d, 1H), 3.77 (t, 4H), 3.71 (t, 4H), 3.62 (s, 2H), 3.28 (t, 4H), 2.55 (t, 4H). LRMS (Electrospray, positive): Da/e 307.4 (m+1).

EXAMPLE 91

1-(2-Hydroxy-4-morpholin-4-yl-phenyl)-2imidazol-1-yl-ethanone

Prepared via the amination procedure of Example 90.

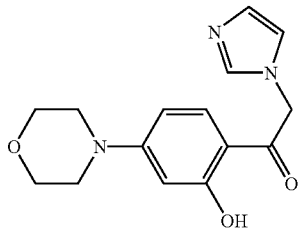

¹H NMR (CDCl₃, 400 MHz): δ 12.05 (br s, 1H), 7.55–7.50 (m, 2H), 7.14 (s, 1H), 6.95 (s, 1H), 6.42 (dd, 1H), 6.29 (d, 1H), 5.28 (s, 2H), 3.83 (t, 4H), 3.36 (t, 4H). LRMS (Electrospray, positive): Da/e 288.3 (m+1). LRMS (Electrospray, negative): Da/e 286.3 (m−1).

EXAMPLE 92

1-(2-Hydroxy-4-morpholin-4-yl-phenyl)-1-pyrrolidin-1-yl-methanone

Prepared via the amination procedure of Example 90.

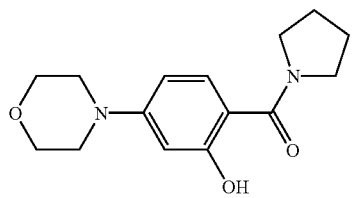

¹H NMR (CDCl₃, 400 MHz): δ 7.77 (d, 1H), 6.38 (dd, 1H), 6.26 (d, 1H), 3.82 (t, 4H), 3.77 (s, 2H), 3.30 (t, 4H), 2.71 (br s, 4H), 1.89–1.82 (m, 4H). LRMS (Electrospray, positive): Da/e 291.3 (m+1).

EXAMPLE 93

1-(2-Hydroxy-4-morpholin-4-yl-phenyl)-1-(4-methyl-piperazin-1-yl)-methanone

Prepared via the amination procedure of Example 90.

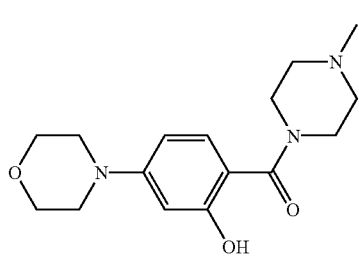

¹H NMR (CDCl₃, 400 MHz): δ 7.76 (d, 1H), 6.35 (dd, 1H), 6.25 (d, 1H), 3.79 (t, 4H), 3.62 (s, 2H), 3.29 (t, 4H), 2.62–2.29 (m, 8H), 2.28 (s, 3H). LRMS (Electrospray, positive): Da/e 320.4 (m+1). LRMS (Electrospray, negative): Da/e 318.4 (m−1).

EXAMPLE 94

2-Hydroxy-4-morpholin-4-yl-phenyl-1-piperidin-1-yl-methanone

Prepared via the amination procedure of Example 90.

¹H NMR (CDCl₃, 400 MHz): δ 7.83 (d, 1H), 6.37 (dd, 1H), 6.25 (d, 1H), 3.80 (t, 4H), 3.53 (s, 2H), 3.29 (t, 4H), 2.55 (br s, 4H), 1.70–1.62 (m, 4H), 1.47 (br s, 2H). LRMS (Electrospray, positive): Da/e 305.4 (m+1).

EXAMPLE 95

2-(Benzyl-methyl-amino)-1-(2-hydroxy-4-morpholin-4-yl-phenyl)-ethanone

Prepared via the amination procedure of Example 90.

¹H NMR (CDCl₃, 400 MHz): δ 7.75 (d, 1H), 7.37–7.25 (m, 5H), 6.34 (dd, 1H), 6.26 (d, 1H), 3.81 (t, 4H), 3.64 (d, 2H), 3.31 (t, 4H), 2.33 (s, 3H). LRMS (Electrospray, positive): Da/e 341.4 (m+1).

EXAMPLE 96

2-Acetylthio-1-(2-hydroxy-4-morpholin-4-yl-phenyl)-ethanone

Prepared via the amination procedure of Example 90 with potassium thioacetate:

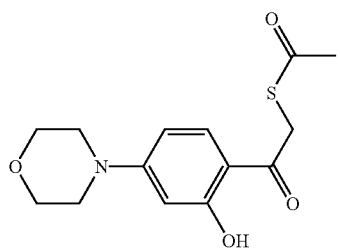

¹H NMR (CDCl₃, 400 MHz): δ 12.30 (s, 1H), 7.64 (d, 1H), 6.39 (dd, 1H), 6.26 (d, 1H), 4.29 (s, 2H), 3.82 (t, 4H), 3.34 (t, 4H), 2.40 (s, 3H). ¹³C NMR (CDCl₃, 100 MHz): δ 195.6, 194.1, 165.2, 156.8, 131.9, 110.5, 100.3, 66.7, 47.1, 35.6, 30.5. LRMS (Electrospray, positive): Da/e 296.1 (m+1).

Example 97

1-(2-Hydroxy-4-morpholin-4-yl-phenyl)-2-mercapto-ethanone

To a stirred solution of thioester (74.1 mg; 0.25 mmol) in dry MeOH (2 mL) was added sodium methoxide (5 mg; 0.1 mmol) at room temperature under a nitrogen atmosphere. The resulting mixture was allowed to stir for 22 hours, then concentrated at reduced pressure and redissolved in CH₂Cl₂ (10 mL). This solution was washed with 1 N aqueous hydrochloric acid (2×3 mL), water and brine then dried (MgSO₄), filtered and concentrated in vacuo. The residue was purified via radial chromatography (1 mm chromatotron plate with 20% EtOAc in hexanes) to provide the free thiol as a pale yellow solid (10.1 mg; 16%).

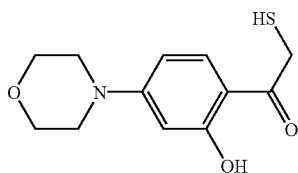

¹H NMR (CDCl₃, 400 MHz): δ 12.46 (s, 1H), 7.53 (d, 1H), 6.37 (dd, 1H), 6.26 (d, 1H), 4.04 (s, 2H), 3.82 (t, 4H), 3.34 (t, 4H). LRMS (Electrospray, negative): Da/e 252.0 (m−1).

EXAMPLE 98

6-Morpholin-4-yl-2-hydrobenzo(b)furan-3-one

Prepared via the amination procedure of Example 90 via omission of amine.

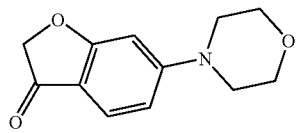

¹H NMR (CDCl₃, 400 MHz): δ 7.50 (d, 1H), 6.59 (dd, 1H), 6.36 (d, 1H), 4.57 (s, 2H), 3.83 (t, 4H), 3.35 (t, 4H). ¹³C NMR (CDCl₃, 100 MHz): δ 196.9, 176.5, 158.6, 125.2, 112.2, 109.7, 95.6, 75.7, 66.7, 47.7.

EXAMPLE 99

4-(2-Methyl-4-morpholin-4-yl-phenyl)-2-(3-pyridyl)-1,3-thiazole

Thiazole Cyclization Procedure:

A stirred solution of chloro-ketone (76 mg; 0.30 mmol) and 3-thioamide-pyridine (41 mg; 0.30 mmol) in ethanol (2 mL) was heated to reflux for 5 hours under a nitrogen atmosphere. The reaction was allowed to cool to room temperature, then concentrated in vacuo. The dark oil was purified by radial chromatography (2 mm chromatotron plate with 5% MeOH in CH₂Cl₂) to provide the heterocycle as a yellow oil (27 mg; 27%).

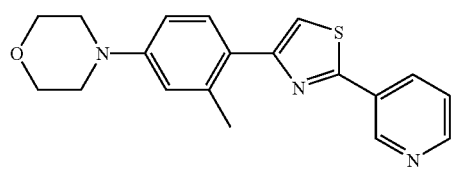

¹H NMR (CDCl₃, 400 MHz): δ 11.53 (br s, 1H), 9.16 (d, 1H), 8.69 (dd, 1H), 8.21 (dt, 1H), 7.51 (d, 1H), 7.45–7.40 (m, 2H), 6.51 (t, 1H), 6.49 (d, 1H), 3.86 (t, 4H), 3.22 (t, 4H). LRMS (Electrospray, positive): Da/e 340.3 (m+1). LRMS (Electrospray, negative): Da/e 338.3 (m−1).

EXAMPLE 100

5-Morpholin-4-yl-2-(2-phenylamino-1,3-thiazol-4-yl)-phenol

Prepared via the thiazole cyclization procedure of Example 99.

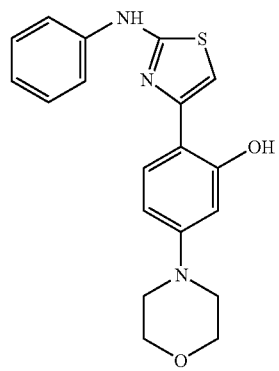

¹H NMR (d6-DMSO, 400 MHz): δ 11.02 (s, 1H), 10.34 (s, 1H), 7.68 (d, 1H), 7.49 (d, 2H), 7.34 (t, 2H), 7.14 (s, 1H), 6.99 (t, 1H), 6.50 (dd, 1H), 6.37 (d, 1H), 3.71 (t, 4H), 3.09 (t, 4H). LRMS (Electrospray, negative): Da/e 352.2 (m−1).

EXAMPLE 101

3-Methoxy-1-morpholin-4-yl-benzene

To a stirred mixture of 3-morpholinyl-phenol (3.8 g; 21.2 mmol) and powdered K$_2$CO$_3$ (4.4 g; 31.8 mmol) in dry DMF (15 mL) was added iodomethane (1.45 mL; 23.3 mmol) via syringe at room temperature under nitrogen atmosphere. The resulting mixture was allowed to stir at room temperature for 22 hours. The reaction was diluted with ether (150 mL) and washed successively with water (2×40 mL) and brine (40 mL), then dried (MgSO$_4$), filtered and concentrated in vacuo to provide the desired ether as a yellow oil (2.51 g; 61%).

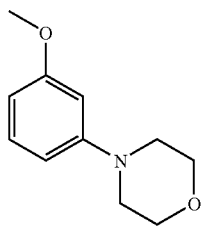

$^1$H NMR (CDCl$_3$, 400 MHz): δ 7.19 (t, 1H), 6.53 (ddd, 1H), 6.45 (d, 1H), 3.85 (t, 4H), 3.80 (s, 3H), 3.15 (t, 4H). LRMS (Electrospray, positive): Da/e 194.1 (m+1).

EXAMPLE 102

4-Methoxy-2-morpholin-4-yl-benzenesulfonic acid

To a cooled (0° C.), stirred portion of 1-methoxy-3-morpholin-4-yl-benzene (1.08 g; 5.6 mmol) was added neat to chlorosulfonic acid (1.8 mL; 28 mmol) via pipette over 2 minutes under calcium sulfate-dried atmosphere. The resulting thick, red solution was allowed to warm to room temperature and stirred for 5 hours. The resulting solution was poured onto ice, then extracted with CH$_2$Cl$_2$ (3×50 mL). Combined organic layers then were washed with brine, dried (MgSO$_4$), filtered and concentrated in vacuo to give the acid as a light green solid (0.31 g; 20%).

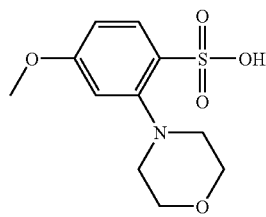

$^1$H NMR (CDCl$_3$, 400 MHz): δ 8.14 (d, 1H), 7.08 (dd, 1H), 6.85 (t, 1H), 4.23 (dd, 1H), 4.11–4.01 (m, 2H), 3.90 (d, 3H), 3.86 (t, 1H), 3.67 (d, 1H), 3.57–3.50 (m, 2H), 3.37 (t, 1H). LRMS (Electrospray, negative): Da/e 272.0 (m−1).

EXAMPLE 103

4-Methoxy-2-morpholin-4-yl-benzenesulfonyl chloride

A mixture of 4-methoxy-2-morpholin-4-yl-benzenesulfonyl chloride (0.31 g; 1.14 mmol) and thionyl chloride (25 mL) was refluxed under a calcium sulfate-dried atmosphere for 4 hours. Excess thionyl chloride was distilled from the residue, which was dried in vacuo to provide the crude sulfonyl chloride as a brown solid (0.30 g; 90%).

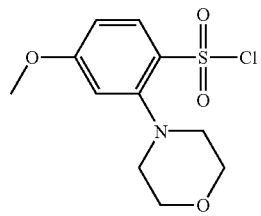

$^1$H NMR (CDCl$_3$, 400 MHz): δ 7.98 (d, 1H), 6.86 (d, 1H), 6.77 (dd, 1H), 3.90–3.86 (m, 7H), 3.07–3.04 (m, 4H).

EXAMPLE 104

4-Methoxy-2-morpholin-4-yl-N-methyl-benzenesulfonamide

Sulfonylation Procedure

To a stirred solution of 4-methoxy-2-morpholin-4-yl-benzenesulfonyl chloride (37 mg; 0. 13 mmol) in dry CH$_2$Cl$_2$ (1 mL) was added methylamine (0.16 mL of 2.0 M solution in tetrahydrofuran; 0.32 mmol) via syringe at room temperature under a nitrogen atmosphere. After stirring for 15 hours, the reaction was diluted with CH$_2$Cl$_2$ (25 mL), washed with water, saturated aqueous NaHCO$_3$ and brine, then dried (MgSO$_4$), filtered, and concentrated in vacuo. The residue was purified via HPLC (Biotage with 2:1 hexanes/EtOAc) to provide the sulfonamide as a white solid (12.5 mg; 34%).

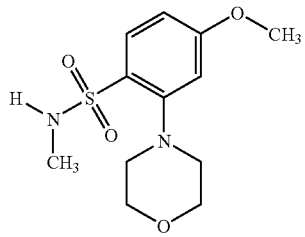

$^1$H NMR (CDCl$_3$, 400 MHz): δ 7.95 (d, 1H), 6.87 (d, 1H), 6.80 (dd, 1H), 5.68 (br d, 1H), 3.87 (s, 7H), 3.03 (t, 4H), 2.47 (d, 3H). $^{13}$C NMR (CDCl$_3$, 100 MHz): δ 164.1, 152.3, 132.9, 126.2, 110.3, 109.9, 67.9, 56.0, 54.5, 30.1. LRMS (Electrospray, positive): Da/e 287.2 (m+1). LRMS (Electrospray, negative): Da/e 285.4 (m−1).

EXAMPLE 105

4-Methoxy-2-morpholin-4-yl-N-benzyl-benzenesulfonamide

Prepared via the sulfonylation procedure of Example 104.

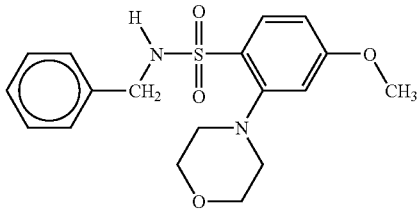

$^1$H NMR (CDCl$_3$, 400 MHz): δ 8.00 (dd, 1H), 7.23–7.19 (m, 3H), 7.02 (dd, 2H), 6.82 (dd, 1H), 6.73 (d, 1H), 6.08 (t, 1H), 3.98 (d, 2H), 3.87 (d, 3H), 3.64 (br s, 4H), 2.77 (t, 4H). $^{13}$C NMR (CDCl$_3$, 100 MHz): δ 164.1, 152.3, 136.7, 132.2, 128.9, 128.3, 128.2, 127.9, 110.3, 109.7, 67.7, 56.0, 54.2, 48.6. LRMS (Electrospray, positive): Da/e 363.3 (m+1). LRMS (Electrospray, negative): Da/e 361.7 (m−1).

EXAMPLE 106

4-Methoxy-2-morpholin-4-yl-N-cyclopropylmethyl-benzenesulfonamide

Prepared via the sulfonylation procedure of Example 104.

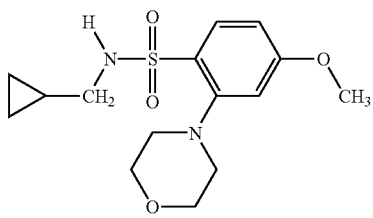

$^1$H NMR (CDCl$_3$, 400 MHz): δ 7.99 (dd, 1H), 6.87 (d, 1H), 6.80 (dd, 1H), 6.12 (br s, 1H), 3.87–3.85 (m, 7H), 3.04 (t, 4H), 1.95 (c, 1H), 0.64–0.57 (m, 2H), 0.52–0.48 (m, 2H). $^{13}$C NMR (CDCl$_3$, 100 MHz): δ 164.2, 152.4, 132.8, 127.5, 110.4, 109.9, 67.9, 56.0, 54.4, 25.2, 6.1. LRMS (Electrospray, negative): Da/e 311.7 (m−1).

EXAMPLE 107

N,N-Diethyl-(3-morpholin-4-yl-phenoxy)carboxamide

To a stirred mixture of 3-morpholinylphenol (0.34 g; 1.9 mmol) and powdered K$_2$CO$_3$ (0.576 g; 4.2 mmol) in dry acetonitrile (10 mL) was added diethyl carbamylchloride (0.26 mL; 2.0 mmol) via syringe at room temperature under nitrogen atmosphere. The resulting mixture was heated to reflux for 24 hours, then allowed to cool to room temperature. The reaction was diluted with EtOAc (60 mL), washed with water (2×20 mL) and brine, then dried (MgSO$_4$), filtered, and concentrated in vacuo. The residue was purified via radial chromatography (4 mm chromatotron plate with 2:1 hexanes/EtOAc) to provide the carbamate as a clear, colorless oil (0.39 g; 74%).

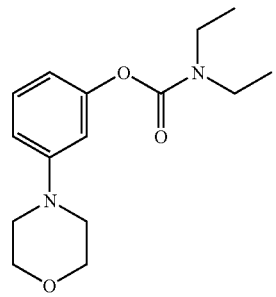

$^1$H NMR (CDCl$_3$, 400 MHz; mixture of rotomers): δ 7.22 (dt, 1H), 6.72 (ddd, 1H), 6.66 (t, 1H), 6.62 (ddd, 1H), 3.83 (dt, 4H), 3.40 (br q, 4H), 3.15 (dt, 4H), 1.26–1.18 (m, 6H). LRMS (Electrospray, positive): Da/e 279.1 (m+1).

EXAMPLE 108

N,N-Diethyl-(2-benzenesulfonyl-5-morpholin-4-yl-phenoxy)carboxamide

To a cooled (−78° C.), stirred solution of carbamate (95 mg; 0.34 mmol) in dry tetrahydrofuran (2 mL) and tetramethylethylenediamine (0.4 mL) was added sec-butyllithium (0.29 mL of a 1.3 M solution in cyclohexane; 0.38 mmol) via syringe under a nitrogen atmosphere. The resulting solution was allowed to stir at −78° C. for 0.6 hour, then benzenesulfonyl fluoride (0.043 mL; 0.36 mmol) was added via syringe. The resulting light yellow solution was allowed to stir at −78° C. for 2.5 hours, then warmed to room temperature and stirred overnight. The reaction was quenched with water, extracted with ether (3×20 mL). Combined organic layers were washed with brine, dried (MgSO$_4$), filtered, and concentrated in vacuo. The residue was purified via radial chromatography (2 mm chromatotron plate with 1:1 hexanes/EtOAc) to provide the desired sulfone (49 mg; 67% based on recovered starting material).

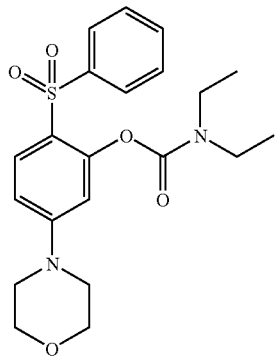

$^1$H NMR (CDCl$_3$, 400 MHz; mixture of rotomers): δ 7.96 (dd, 1H), 7.79 (dd, 2H), 7.50 (c, 1H), 7.42 (tt, 2H), 6.74 (dd, 1H), 6.57 (d, 1H), 3.79 (t, 4H), 3.39 (q, 2H), 3.26 (t, 4H), 3.20 (q, 2H), 1.17 (t, 3H), 1.06 (t, 3H). LRMS (Electrospray, positive): Da/e 419.3 (m+1).

EXAMPLE 109

2-Benzenesulfonyl-5-morpholin-4-yl-phenol

To a stirred solution of carbamate (31 mg; 0.07 mmol) in ethanol (1.5 mL) and water (0.3 mL) was added potassium hydroxide (118 mg; 2.1 mmol). The resulting solution was heated to reflux for 5 hours, then allowed to cool to room temperature. The reaction was neutralized with the addition of aqueous hydrochloric acid (0.35 mL of 6.0 N solution; 2.1 mmol), and the solution concentrated in vacuo. The residue was purified via radial chromatography (2 mm chromatotron plate with 2:1 hexanes/EtOAc) to provide the phenol as a clear semi-solid (15.6 mg; 66%).

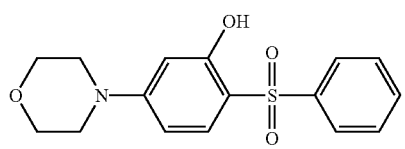

$^1$H NMR (CDCl$_3$, 400 MHz): δ 9.16 (s, 1H), 7.89–7.87 (m, 2H), 7.56–7.46 (m, 4H), 6.43 (dd, 1H), 6.32 (d, 1H), 3.78 (t, 4H), 3.24 (t, 4H). $^{13}$C NMR (CDCl$_3$, 100 MHz): δ 157.6, 156.7, 143.0, 133.3, 130.6, 129.5, 126.5, 112.5, 107.3, 101.9, 66.7, 47.3. LRMS (Electrospray, negative): Da/e 318.0 (m−1).

EXAMPLE 110

3-Nitro-1-morpholin-4-yl-benzene

Morpholine Ring Construction Procedure

A 2-L 3-necked roundbottom flask equipped with mechanical stirrer, condenser with nitrogen inlet, and thermocouple was charged with 138.13 (1.0 mol) 3-nitrophenylamine, 152.0 g (1.1 mol) K$_2$CO$_3$, and 1 L DMF. To this was added 129 mL (1.1 mol) of bis 2-chloroethylether and 30 g (0.2 mol) NaI and the mixture heated at reflux for 72 h. The reaction was allowed to cool to room temperature, then filtered, and the filtrate concentrated in vacuo with water bath at 60° C. The resulting dark oil was treated with 500 mL MeOH and Darco, and heated on steam bath for 1 h. The mixture then was filtered over GF/F paper and the filtrate allowed to slowly cool to room temperature resulting in crystal formation. The mixture was placed in at 5° C. overnight then filtered cold, washing with MeOH. Upon drying recovered the desired aryl morpholine 54.9 g (26.3%) was recovered as orange needles.

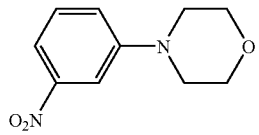

$^1$H NMR (CDCl$_3$, 400 MHz): δ 7.72–7.67 (m, 2H), 7.39 (t, 1H), 7.19 (dd, 1H), 3.88 (t, 4H), 3.25 (t, 4H). LRMS (Electrospray, positive): Da/e 209.2 (m+1).

EXAMPLE 111

3-Morpholin-4-yl-phenylamine

Hydrogenation Procedure

A 500 mL roundbottom flask equipped with stir bar and 3-way stopcock charged with MeOH/tetrahydrofuran/water (200 mL of 2:1:1) was purged thoroughly with nitrogen. To this was added 1.0 g of 10% Pd/C followed by addition of 10 g (48.0 mmol) of 3-morpholinyl nitrobenzene. The mixture then was stirred under a hydrogen atmosphere for 4 days (1 atm). The reaction was filtered over GF/F filter paper and the filtrate concentrated in vacuo to remove MeOH and THF. The resulting solid was recovered by filtration, washed with water, air dried, then dried in vacuo to give 7.3 g (83% yield) of the desired aniline as beige crystals.

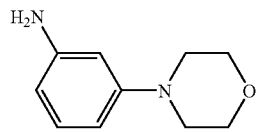

$^1$H NMR (CDClH, 400 MHz): δ 7.06 (t, 1H), 6.35 (ddd, 1H), 6.26–6.23 (m, 2H), 3.84 (t, 4H), 3.62 (br s, 2H), 3.12 (t, 4H). LRMS (Electrospray, positive): Da/e 179.2 (m+1).

EXAMPLE 112

1-(2-Amino-4-morpholin-4-yl-phenyl)-2-chloro-ethanone

Prepared via the Sugasawa procedure of Example 89.

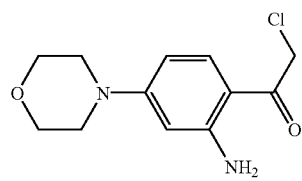

$^1$H NMR (CDCl$_3$, 400 MHz): δ 7.50 (d, 1H), 6.36 (br s, 2H), 6.22 (dd, 1H), 5.94 (d, 1H), 4.57 (s, 2H), 3.81 (t, 4H), 3.27 (t, 4H). LRMS (Electrospray, positive): Da/e 255.3 (m+1).

EXAMPLE 113

2-Amino-4-morpholin-4-yl-N-benzyl-N-methyl-benzamide

Prepared via the amination procedure of Example 90.

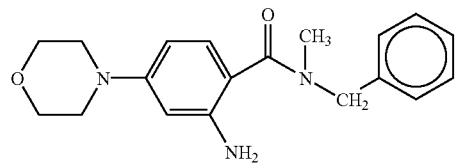

$^1$H NMR (CDCl$_3$, 400 MHz): δ 7.72 (d, 1H), 7.37–7.23 (m, 5H), 6.35 (br s, 2H), 6.17 (dd, 1H), 5.93 (d, 1H), 3.81

(t, 4H), 3.64 (s, 2H), 3.63 (s, 2H), 3.24 (t, 4H), 2.32 (s, 3H). $^{13}$C NMR (CDCl$_3$, 100 MHz): δ 197.3, 155.2, 152.9, 138.8, 133.3, 129.4, 128.4, 127.3, 110.6, 103.8, 99.4, 66.9, 64.2, 62.6, 47.6, 43.1. LRMS (Electrospray, positive): Da/e 340.1 (m+1).

EXAMPLE 114

1-(2-Amino-4-morpholin-4-yl-phenyl)-1-pyrrolidin-1-yl-methanone

Prepared via the amination procedure of Example 90.

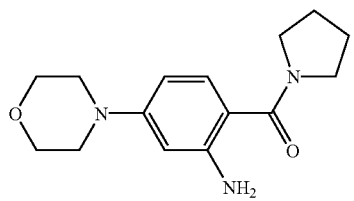

$^1$H NMR (CDCl$_3$, 400 MHz): δ 7.68 (d, 1H), 6.34 (br s, 2H), 6.19 (dd, 1H), 5.94 (d, 1H), 3.83 (s, 2H), 3.80 (t, 4H), 3.23 (t, 4H), 2.66 (br s, 4H), 1.84–1.78 (m, 4H). $^{13}$C NMR (CDCl$_3$, 100 MHz): δ 196.3, 155.1, 152.7, 132.5, 110.4, 104.0, 99.6, 66.9, 62.6, 54.7, 47.6, 24.0. LRMS (Electrospray, positive): Da/e 290.0 (m+1).

EXAMPLE 115

(2-Amino-4-morpholin-4-yl-phenyl)-1-piperidin-1-yl-methanone

Prepared via the amination procedure of Example 90.

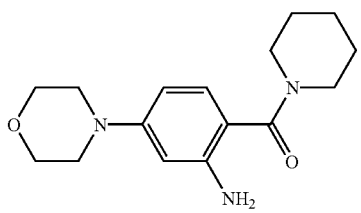

$^1$H NMR (CDCl$_3$, 400 MHz): δ 7.77 (d, 1H), 6.34 (br s, 2H), 6.19 (dd, 1H), 5.93 (d, 1H), 3.80 (t, 4H), 3.60 (s, 2H), 3.23 (t, 4H), 2.49 (br s, 4H), 1.65–1.59 (m, 4H), 1.46–1.42 (m, 2H). $^{13}$C NMR (CDCl$_3$, 100 MHz): δ 196.5, 155.1, 152.8, 132.9, 110.8, 103.9, 99.5, 66.9, 65.9, 55.3, 47.6, 26.2, 24.4. LRMS (Electrospray, positive): Da/e 304.0 (m+1).

EXAMPLE 116

2-Amino-4-fluoro-benzoic acid methyl ester

To a cooled (0° C.), stirred solution of 4-fluoro-2-aminobenzoic acid (2.68 g; 17.3 mmol) in dry tetrahydrofuran (60 mL) and MeOH (10 mL) was added a solution of trimethylsilyldiazomethane in hexanes (12 mL of 2.0 N; 24 mmol) via syringe over 20 minutes under nitrogen atmosphere. The resulting solution was allowed to warm to room temperature and stirred for 2 hours then concentrated in vacuo to provide the ester a light yellow solid (~100%).

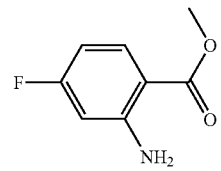

$^1$H NMR (d6-DMSO, 400 MHz): δ 7.76 (dd, 1H), 6.91 (br s, 2H), 6.53 (dd, 1H), 6.34 (ddd, 1H), 3.78 (s, 3H).

EXAMPLE 117

4-Fluoro-2-(2,2,2-trifluoroacetylamino)-benzoic acid methyl ester

To a cooled (0° C.), stirred solution of methyl ester (0.525 g; 3.1 mmol) in dry CH$_2$Cl$_2$ (20 mL) was added trifluoroacetic anhydride (0.5 mL; 3.5 mmol) via syringe under a nitrogen atmosphere. The resulting solution was allowed to stir for 20 minutes, then quenched with the addition of MeOH (0.5 mL) and water (2 mL). The mixture was diluted with CH$_2$Cl$_2$ (20 mL) and washed with water (3×5 mL) and brine then dried (MgSO$_4$), filtered and concentrated in vacuo to provide the amide as a light yellow solid (89%).

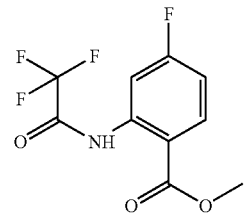

$^1$H NMR (CDCl$_3$, 400 MHz): δ 12.21 (br s, 1H), 8.42 (dd, 1H), 8.06 (dd, 1H), 6.98 (ddd, 1H), 3.98 (s, 3H). LRMS (Electrospray, negative): Da/e 264.3 (m−1).

EXAMPLE 118

4-Morpholin-4-yl-2-(2,2,2-trifluoroacetylamino)-benzoic acid methyl ester

Nucleophilic Addition of Morpholine Procedure

To a stirred solution of arylfluoride (0.727 g; 2.7 mmol) in dimethylsulfoxide (20 mL) was added morpholine (0.95 mL; 10.9 mmol), and the resulting solution was heated at 80° C. for 4 hours under a nitrogen atmosphere. After cooling to room temperature, the reaction was diluted with EtOAc (60 mL) and washed with 1 N aqueous hydrochloric acid. The aqueous layer was back extracted with EtOAc (3×10 mL), and combined organic layers were washed with water (3×10 mL) and brine, then dried (MgSO$_4$), filtered, and concentrated in vacuo. The residue was purified via flash chromatography (3:1 hexanes/EtOAc on silica gel) to provide the arylmorpholine as a white solid (629 mg; 70%).

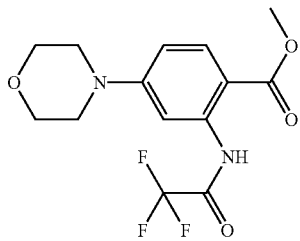

¹H NMR (CDCl₃, 400 MHz): δ 12.51 (s, 1H), 8.22 (d, 1H), 7.94 (d, 1H), 6.62 (dd, 1H), 3.91 (s, 3H), 3.84 (t, 4H), 3.35 (t, 4H). LRMS (Electrospray, negative): Da/e 331.3 (m−1).

EXAMPLE 119

2-Amino-4-morpholin-4-yl-benzoic acid

Lithium Hydroxide Hydrolysis Procedure

To a stirred solution of ester-trifluoroamide (54 mg; 0.16 mmol) in tetrahydrofuran (1 mL), MeOH (0.5 mL) and water (0.5 mL) was added lithium hydroxide monohydrate (30 mg; 0.71 mmol) at room temperature. The resulting solution was heated to 50° C. for 22 hours, then allowed to cool to room temperature. The mixture was neutralized with 1 N aqueous hydrochloric acid (0.7 mL; 0.70 mmol), then extracted with EtOAc (3×10 mL). Combined organic layers were washed with water and brine, then dried (MgSO₄), filtered and concentrated in vacuo. The residue was purified via radial chromatography (2 mm chromatotron plate with 5% MeOH in CH₂Cl₂) to provide the acid as a light yellow solid.

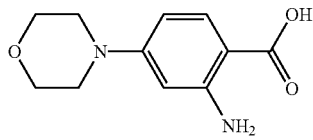

¹H NMR (d6-DMSO, 400 MHz): δ 7.52 (d, 1H), 6.19 (dd, 1H), 6.12 (d, 1H), 3.68 (t, 4H), 3.11 (t, 4H). LRMS (Electrospray, negative): Da/e 221.3 (m−1).

EXAMPLE 120

2-Methylsulfonylamino-4-morpholin-4-yl-benzoic acid

To a suspension of 2-amino-4-morpholin-4-yl-benzoic acid (230 mg; 1.04 mmol) in CH₂Cl₂ (3 mL) was added N-methyl-N-(trimethylsilyl)trifluoroacetamide (0.4 mL; 2.1 mmol) via syringe at room temperature under a nitrogen atmosphere. The resulting mixture was heated to reflux for 10 minutes, then allowed to cool to room temperature. Methanesulfonyl chloride (1.2 eq.) and triethylamine (1.2 eq.) were added, and the resulting mixture allowed to stir for 2 hours. The reaction was diluted with CH₂Cl₂ (30 mL) and washed with water (2×10 mL) and brine, then dried (MgSO₄), filtered, and concentrated in vacuo to provide the sulfonamide as a white solid (280 mg; 90%).

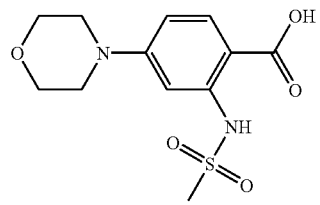

¹H NMR (d6-DMSO, 400 MHz): δ 10.88 (s, 1H), 7.80 (d, 1H), 6.92 (d, 1H), 6.71 (dd, 1H), 3.71 (t, 4H), 3.25 (t, 4H), 3.16 (s, 3H). LRMS (Electrospray, negative): Da/e 299.0 (m−1).

EXAMPLE 121

4-Morpholin-4-yl-2-(2,2,2-trifluoroacetylamino)-N-benzyl-benzamide

Prepared by the EDC Coupling procedure of Example 75.

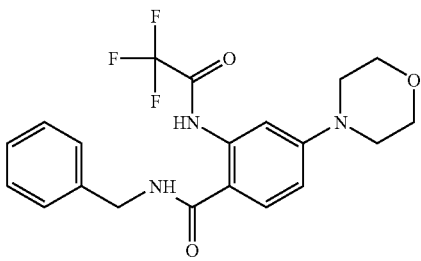

¹H NMR (CDCl₃, 400 MHz): δ 13.33 (s, 1H), 8.26 (d, 1H), 7.42–7.32 (m, 6H), 6.60 (dd, 1H), 6.39 (br s, 1H), 4.63 (d, 2H), 3.84 (t, 4H), 3.31 (t, 4H). LRMS (Electrospray, negative): Da/e 406.3 (m−1).

EXAMPLE 122

N,N-Dimethyl-4-morpholin-4-yl-2-(2,2,2-trifluoro-acetylamino)-benzamide

Prepared via the Weinreb amidation procedure of Example 56.

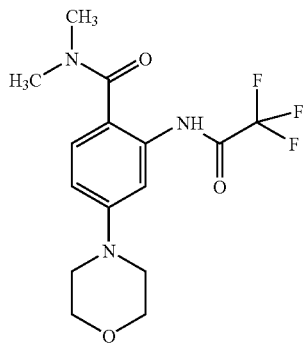

¹H NMR (CDCl₃, 400 MHz): δ 11.26 (s, 1H), 7.99 (d, 1H), 7.27 (d, 1H), 6.63 (dd, 1H), 3.84 (t, 4H), 3.28 (t, 4H), 3.11 (s, 6H). LRMS (Electrospray, positive): Da/e 346.3 (m+1). LRMS (Electrospray, negative): Da/e 344.3 (m−1).

EXAMPLE 123

2-Amino-4-morpholin-4-yl-N,N-dimethyl-benzamide

Prepared via the lithium hydroxide hydrolysis procedure of Example 119 (without heat).

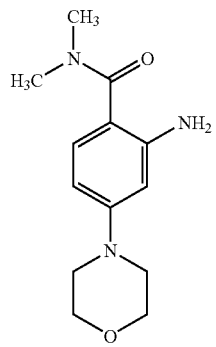

$^1$H NMR (CDCl$_3$, 400 MHz): δ 7.00 (d, 1H), 6.23 (dd, 1H), 6.14 (d, 1H), 4.58 (br s, 2H), 3.80 (t, 4H), 3.13 (t, 4H), 3.03 (s, 6H). LRMS (Electrospray, positive): Da/e 250.1 (m+1).

EXAMPLE 124

N-Methyl-4-morpholin-4-yl-2-(2,2,2-trifluoroacetylamino)-benzamide

Prepared via the Weinreb amidation procedure of Example 56.

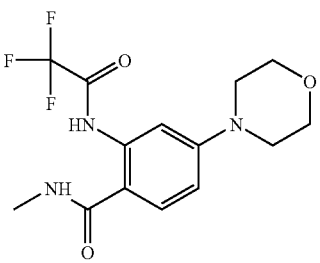

$^1$H NMR (CDCl$_3$, 400 MHz): δ 13.35 (s, 1H), 8.24 (d, 1H), 7.38 (d, 1H), 6.61 (dd, 1H), 6.19 (br s, 1H), 3.84 (t, 4H), 3.31 (t, 4H), 3.00 (d, 3H). LRMS (Electrospray, negative): Da/e 330.1 (m−1).

EXAMPLE 125

2-Amino-4-morpholin-4-yl-benzoic acid methyl ester

Prepared via the lithium hydroxide hydrolysis procedure of Example 119 (without heating).

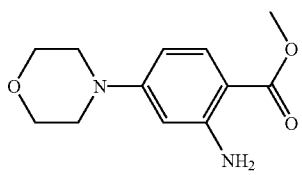

$^1$H NMR (CDCl$_3$, 400 MHz): δ 7.74 (d, 1H), 6.23 (dd, 1H), 6.00 (d, 1H), 5.71 (br s, 2H), 3.85–3.81 (m, 7H), 3.22 (t, 4H). LRMS (Electrospray, positive): Da/e 237.4 (m+1).

EXAMPLE 126

2-Acetylamino-4-morpholin-4-yl-benzolic acid methyl ester

To a stirred solution of methyl 2-amino-4-morpholin-4-ylbenzoate (55 mg; 0.23 mmol) in dry CH$_2$Cl$_2$ (2 mL) was added acetic anhydride (0.05 mL; 0.53 mmol) and pyridine (0.02 mL; 0.25 mmol) via syringe at room temperature under a nitrogen atmosphere. The resulting solution was allowed to stir for 22 hours, then diluted with EtOAc (15 mL) and washed with 0.5 N aqueous hydrochloric acid, water, and brine, then dried (MgSO$_4$), filtered and concentrated in vacuo to provide the amide as a white solid (56 mg; 88%).

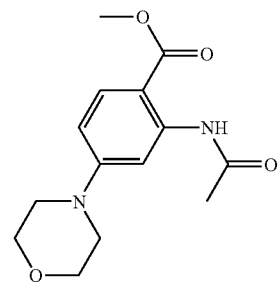

$^1$H NMR (CDCl$_3$, 400 MHz): δ 11.24 (s, 1H), 8.33 (s, 1H), 7.88 (d, 1H), 6.50 (d, 1H), 3.86 (br s, 4H), 3.32 (br s, 4H), 2.22 (s, 3H). LRMS (Electrospray, positive): Da/e 279.3 (m+1).

EXAMPLE 127

2-Acetylamino-4-morpholin-4-yl-benzoic acid

Prepared via the lithium hydroxide hydrolysis procedure of Example 119 (with heat).

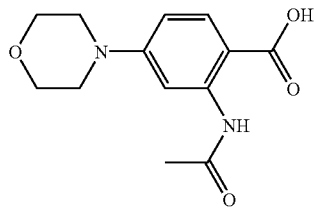

$^1$H NMR (d6-DMSO, 400 MHz): δ 12.93 (s, 1H), 11.35 (s, 1H), 8.18 (s, 1H), 7.81 (d, 1H), 6.68 (d, 1H), 3.73 (br s, 4H), 3.24 (br s, 4H), 2.12 (s, 3H). LRMS (Electrospray, negative): Da/e 263.3 (m−1).

EXAMPLE 128

2-Methanesulfonylamino-4-morpholin-4-yl-benzoic acid methyl ester

To stirred solution of methyl 2-amino-4-morpholin-4-ylbenzoate (47 mg; 0.2 mmol) in CH$_2$Cl$_2$ (2 mL) was added Hunig's base (0.10 mL; 0.57 mmol) and methanesulfonyl chloride (0.040 mL; 0.52 mmol) at room temperature under a nitrogen atmosphere. After stirring for 4 hours, the reaction was quenched with MeOH (0.5 mL) and diluted with EtOAc (25 mL). The resulting solution was washed with 0.5 N aqueous hydrochloric acid, water and brine, then dried (MgSO$_4$), filtered, and concentrated in vacuo. The residue was purified via radial chromatography (2:1 hexanes/ EtOAc) to provide the ester-sulfonamide as a yellow solid (45 mg; 72%).

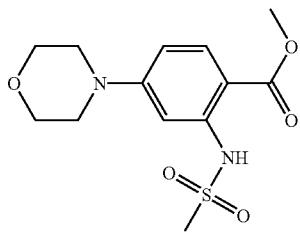

$^1$H NMR (CDCl$_3$, 400 MHz): δ 10.55 (s, 1H), 7.89 (d, 1H), 7.18 (d, 1H), 6.55 (dd, 1H), 3.87 (s, 3H), 3.83 (t, 4H), 3.32 (t, 4H), 3.02 (s, 3H). $^{13}$C NMR (CDCl$_3$, 100 MHz): δ 168.5, 155.3, 142.8, 133.0, 108.5, 105.9, 102.5, 66.7, 52.3, 47.3, 39.8. LRMS (Electrospray, negative): Da/e 313.1 (m−1).

EXAMPLE 129

(2-N-Methyl-N-(2,2,2-trifluoroacetyl)amino]-4-morpholin-4-yl-benzoic acid methyl ester To a stirred solution of (2-N-methyl-N-(2,2,2-trifluoroacetyl)amino)-4-morpholin-4-yl-2-benzoic acid (330 mg; 0.99 mmol) in dry DMF (5 mL) was added K$_2$CO$_3$ (140 mg; 1.01 mmol) and iodomethane (0.065 mL; 1.04 mmol) at room temperature under a nitrogen atmosphere. After stirring for 8 hours, the reaction was diluted with EtOAc (35 mL), washed with water (3×10 mL) and brine, then dried (MgSO$_4$), filtered, and concentrated in vacuo. The residue was purified via radial chromatography (2 mm chromatotron plate with 2:1 hexanes/EtOAc) to provide the N-methyl amide as a white solid (303 mg; 88%).

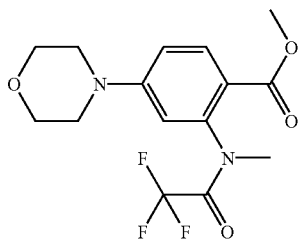

$^1$H NMR (CDCl$_3$, 400 MHz): δ 8.00 (d, 1H), 6.88 (dd, 1H), 6.67 (d, 1H), 3.86 (t, 4H), 3.84 (d, 3H), 3.30 (t, 4H), 3.29 (s, 3H). LRMS (Electrospray, positive): Da/e 347.2 (m+1).

EXAMPLE 130

2-Methylamino-4-morpholin-4-yl-benzoic acid methyl ester

Prepared via the lithium hydroxide hydrolysis procedure of Example 119 (without heat).

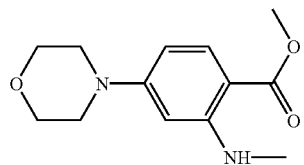

$^1$H NMR (CDCl$_3$, 400 MHz): δ 7.78 (d, 1H), 6.16 (dd, 1H), 5.95 (d, 1H), 3.84 (t, 4H), 3.80 (s, 3H), 3.28 (t, 4H), 2.89 (d, 3H). $^{13}$C NMR (CDCl$_3$, 100 MHz): δ 168.9, 155.9, 153.6, 133.1, 102.4, 94.4, 67.0, 51.3, 48.0, 29.8. LRMS (Electrospray, positive): Da/e 251.4 (m+1).

EXAMPLE 131

2-Methylamino-4-morpholin-4-yl-benzoic acid

Prepared via the lithium hydroxide procedure of Example 119 (with heat).

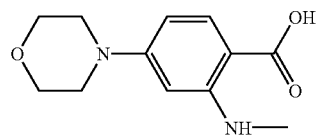

$^1$H NMR (d6-DMSO, 400 MHz): δ 7.59 (d, 1H), 6.17 (dd, 1H), 5.94 (d, 1H), 3.69 (t, 41H), 3.31 (br s, 1H), 3.21 (t, 4H), 2.80 (s, 3H). LRMS (Electrospray, negative): Da/e 235.0 (m−1).

EXAMPLE 132

2-Chloro-1-(2-acetamido-4-morpholin-4-yl-phenyl)-ethanone

A 25-mL round-bottom flask equipped with stir bar and nitrogen inlet was charged with 271.6 mg (1.07 mmol) of 2-amino-4-morpholinyl chloroacetophenone and the resulting solution was chilled (5° C.). To this was added 1 mL (10 mmol) of acetic anhydride. After 18 h, 1 mL MeOH was added, and the reaction stirred for an additional 1 h, then concentrated in vacuo to a brown solid which was purified by radial chromatography (2 mm chromatotron plate). Solvent: 100% CH$_2$Cl$_2$ to 2% MeOH/CH$_2$Cl$_2$. Recovered 170.1 mg (53.7%) of the desired amide as a tan solid.

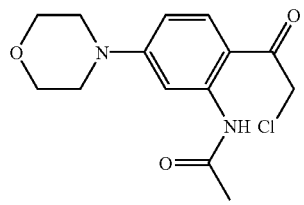

$^1$H NMR (CDCl$_3$, 400 MHz, mixture of rotamers): δ 11.84 (s, 1H), 8.39 (t, 1H), 7.66 (dd, 1H), 6.50 (dt, 1H), 4.65 (d, 2H), 3.82 (dt, 4H), 3.40 (dt, 4H), 2.22 (d, 3H).

EXAMPLE 133

1-Acetyl-6-morpholin-4-yl-1,2-dihydro-indol-3-one

To a cooled (0° C.), stirred suspension of sodium hydride (5.3 mg of 60% dispersion in oil; 0.16 mmol) in dry tetrahydrofuran (2 mL) was added a solution of N-(2-(2-chloroacetyl)-5-morpholin-4-ylphenyl]acetamide (30.8 mg; 0.10 mmol) in dry tetrahydrofuran (2 mL) via syringe under nitrogen atmosphere. The resulting mixture was stirred at 0° C. for 1 hour, then warmed to room temperature and stirred for an additional 2 hours. The reaction mixture was concentrated in vacuo, and the residue purified via radial chromatography (1 mm chromatotron plate with 30% EtOAc in hexanes) to provide the oxoindole as a pinkish tan solid (12.0 mg; 46%).

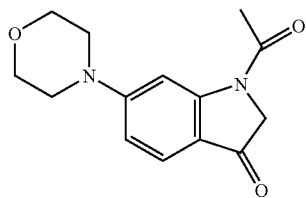

$^1$H NMR (CDCl$_3$, 400 MHz): δ 7.99 (d, 1H), 7.59 (d, 1H), 6.67 (dd, 1H), 4.23 (s, 2H), 3.83 (t, 4H), 3.40 (t, 4H), 2.28 (s, 3H). $^{13}$C NMR (CDCl$_3$, 100 MHz): δ 191.9, 168.7, 157.7, 156.1, 125.3, 110.8, 101.4, 66.7, 57.1, 47.7, 24.8.

EXAMPLE 134

4-Morpholin-4-yl-2-nitrobenzoic acid methyl ester

Prepared via the nucleophilic addition of morpholine procedure of Example 118.

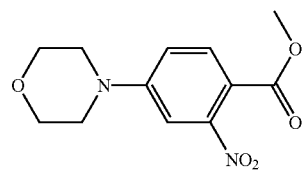

$^1$H NMR (CDCl$_3$, 400 MHz): δ 7.75 (d, 1H), 7.03 (d, 1H), 6.95 (dd, 1H), 3.84 (t, 4H), 3.83 (s, 3H), 3.30 (t, 4H). $^{13}$C NMR (CDCl$_3$, 100 MHz): δ 164.9, 153.6, 151.8, 132.3, 115.7, 114.1, 108.4, 66.5, 52.9, 47.5. LRMS (Electrospray, positive): Da/e 267.1 (m+1).

EXAMPLE 135

4-Morpholin-4-yl-2-nitrobenzoic acid

Prepared via the lithium hydroxide hydrolysis procedure of Example 119 (with heat).

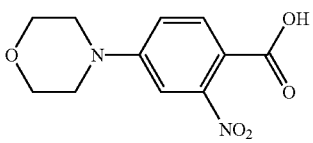

$^1$H NMR (d6-Acetone, 400 MHz): δ 7.87 (d, 1H), 7.21 (d, 1H), 7.18 (dd, 1H), 3.81 (t, 4H), 3.43 (t, 4H). $^{13}$C NMR (d6-Acetone, 100 MHz): δ 205.4, 164.2, 154.3, 132.6, 114.9, 112.2, 107.9, 66.3, 47.3. LRMS (Electrospray, negative): Da/e 251.0 (m−1).

EXAMPLE 136

(4-Morpholin-4-yl-2-nitro)-N-(methylcarboxymethyl)-benzamide

Prepared via the EDC coupling procedure of Example 75.

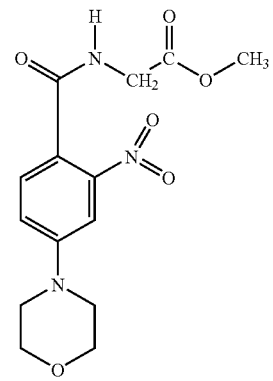

$^1$H NMR (CDCl$_3$, 400 MHz): δ 7.45 (d, 1H), 7.39 (d, 1H), 7.03 (dd, 1H), 6.36 (br s, 1H), 4.22 (d, 2H), 3.87 (t, 4H), 3.80 (s, 3H), 3.27 (t, 4H). LRMS (Electrospray, positive): Da/e 324.2 (m+1).

EXAMPLE 137

Benzyl 2-((4-benzyl)carbonyl]-5-morpholin-4-yl-benzene phosphate

To a stirred, cooled (0° C.) suspension of 2-hydroxy-4-morpholin-4-ylphenyl 4-methoxyphenyl ketone (89 mg, 0.28 mmol) in acetonitrile (1.5 mL) and CH$_2$Cl$_2$ (1 mL) was added 1H-tetrazole (76 mg, 1.1 mmol), followed by dropwise addition of dibenzyl diisopropylphosphoramidite (250 μL, 0.74 mmol). The reaction mixture was stirred under nitrogen at 0° C. for two hours, then warmed to room temperature and diluted with CH$_2$Cl$_2$. The mixture was washed with ice cold saturated aqueous NaHCO$_3$, water, and brine, then dried (MgSO$_4$), filtered, and concentrated in vacuo. The residue was purified by radial chromatography (2:1 hexane/EtOAc, 1 mm silica gel plate) to give a light brown oil (155 mg, 99.4%).

The above-described light brown oil (155 mg, 0.28 mmol) was dissolved in tetrahydrofuran (3 mL) and stirred under nitrogen at −78° C. A solution of 30% hydrogen peroxide in water (1.2 mL) was dropwise added. The reaction mixture was warmed to room temperature, and continued stirred for 45 minutes. It then was extracted with diethyl ether. The organic layer was further washed with saturated aqueous sodium thiosulfate three times, water, saturated aqueous NaHCO$_3$, and brine, then dried (MgSO$_4$), filtered, and concentrated in vacuo. Purification of the residue by radial chromatography (2:1 to 1:2 hexane/EtOAc, 1 mm silica gel plate) yielded a pale yellow oil (126 mg, 79.1%)

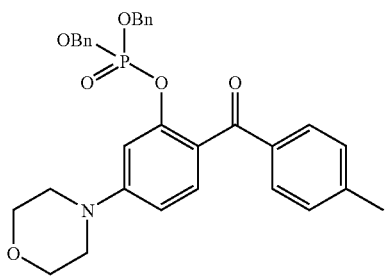

¹H NMR (CDCl₃, 400 MHZ): δ 7.78 (dd, 1 H) 7.77 (d, 1 H), 7.42 (dd, 1 H), 7.36 (s, 1 H), 7.32–7.24 (m, 5 H), 7.22–7.15 (m, 4 H), 6.92–6.84 (m, 3 H), 6.70 (dd, 1 H), 4.86–4.75 (m, 4 H), 3.79 (t, 4 H), 3.79 (s, 3 H), 3.15 (t, 4 H). LRMS (Electrospray, positive): Da/e 574.5 (m+1).

EXAMPLE 138

4-Methylphenyl 4-morpholin-4-yl-2-(phosphonooxy)phenyl methanone disodium salt

To a solution of the above-described diester (126 mg, 0.22 mmol) in MeOH (3 mL) and EtOAc (1 mL) was added 10% palladium on carbon (10 mg). The reaction flask was purged with hydrogen three times. The black suspension then was stirred at room temperature under hydrogen, which was supplied by a balloon. Half an hour later, mass spectroscopy indicated the formation of the mono-debenzylated intermediate (negative electrospray, Da/e 482.2 found). The hydrogenation was allowed to proceed for another 1.5 h for complete debenzylation. The reaction system then was purged with nitrogen. The mixture was filtered through a Nylon-66 membrane to remove the palladium on carbon. To the above-described filtrate was added a solution of NaHCO₃ (37 mg, 0.44 mmol) in water (2 mL) to convert the acid to a bis-sodium salt. The mixture was stirred for ten minutes, then concentrated in vacuo to remove the volatile solvents. The residue then was lyophilized from a mixture of water and 1,4-dioxane to yield a yellow solid (98 mg, 100%). HPLC analysis showed no impurity.

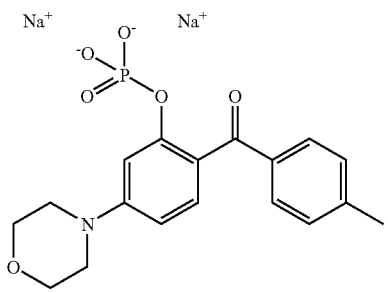

¹H NMR (CD₃OD, 400 MHz): δ 7.76 (d, 1 H), 7.76 (dd, 1 H), 7.45 (d, 1 H), 7.19 (dd, 1 H), 6.96 (d, 1 11), 6.96 (dd, 1 H), 6.54 (dd, 1 H), 3.86 (s, 3 H), 3.81 (t, 4 H), 3.33 (t, 4 H). LRMS (Electrospray, negative):Da/e 392.1 (m−1 for the acid form).

EXAMPLE 139

5-Hydroxy-7-morpholin-4-yl-2-phenyl-chromen-4-one

A solution of trifluoromethanesulfonic acid 5-hydroxy-4-oxo-2-phenyl-4H-chromen-7-yl ester (200 mg, 0.518 mmol), morpholine (0.05 mL, 0.622 mmol), tris(dibenzylideneacetone)dipalladium(0) (9.4 mg, 0.010 mmol), racemic-2,2'bis(diphenylphosphino)-1,1'-binapthyl (19 mg, 0.030 mmol), and cesium carbonate (236 mg, 0.725 mmol) in toluene (5 mL) was heated to reflux for 24 h. The mixture was allowed to cool to room temperature, filtered through a ¾" silica gel (60 Å) plug, then the plug was washed with EtOAc (40 mL). The resulting solution was concentrated under vacuum and purified via Biotage chromatography with gradient elution from 15% EtOAc/hexanes to 50% EtOAc/hexanes to yield 37 mg (22%) of 5-hydroxy-7-morpholin-4-yl-2-phenyl-chromen-4-one. See, A. Echavarren et al., J. Am. Chem. Soc., 109, pp. 5478–5486 (1987). Rf=0.12 (25% EtOAc/hexanes).

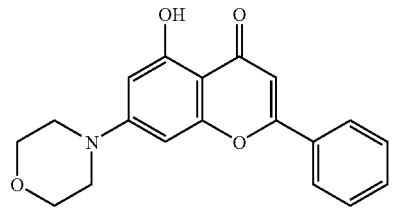

¹H NMR (CDCl₃, 400 MHz) δ 12.56 (s, 1H), 7.85 (d, 2H), 7.54–7.48 (c, 3H), 6.61 (s, 1H), 6.37 (d, 1H), 6.29 (d, 1H), 3.85 (m, 4H), 3.34 (m, 4H). ¹³C (CDCl₃, 100MHz) d 182.0, 163.7, 161.9, 158.3, 156.3, 131.8, 129.2, 126.4, 106.1, 106.0, 104.2, 97.2, 91.7, 66.7, 47.5. LRMS (Electrospray, positive): Da/e 324.6 (m+1).

EXAMPLE 140

5-Hydroxy-2-phenyl-7-piperidin-1-yl-chromen-4-one

A solution of trifluoromethanesulfonic acid 5-hydroxy-4-oxo-2-phenyl-4H-chromen-7-yl ester (130 mg, 0.337 mmol), piperidine (0.040 mL, 0.40 mmol), tris(dibenzylideneacetone) dipalladium(0) (15 mg, 0.017 mmol), biphenyl-2-yl-di-tert-butyl-phosphane (20 mg, 0.067 mmol), and tripotassium phosphate (K₃PO₄) (143 mg, 0.674 mmol) in THF (2 mL) was heated to reflux for 24 h, then cooled to room temperature for 24 h. The reaction mixture was filtered through a ¾" silica gel (60 Å) plug. The plug was washed with EtOAc (75 mL), and the filtrate concentrated. The concentrate was purified via Biotage chromatography eluting with 5% EtOAc/hexanes to yield 18 mg (17%) of 5-hydroxy-2-phenyl-7-piperidin-1-yl-chromen-4-one.

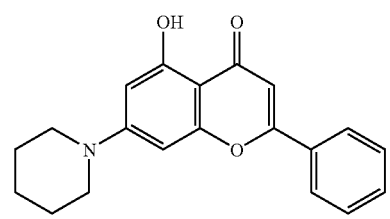

¹H NMR (CDCl₃, 400 MHz) δ 12.6 (s, 1H), 7.87 (m, 2H), 7.52–7.49 (c, 3H), 6.59 (m, 1H), 6.36 (m, 1H), 6.28 (m, 1H), 3.41 (br s, 4H), 1.68 (br s, 6H). LRMS (Electrospray, positive): Da/e 322.5 (m+1).

EXAMPLE 141

Trifluoromethanesulfonic acid 3,5-dihydroxy-4-oxo-2-phenyl-4H-chromen-7-yl ester To a solution of galangin (100 mg, 0.00037 mmol) and triethylamine (0.103 mL, 0.740 mmol) in CH₂Cl₂ (6 mL) was added N-phenyltrifluoromethanesulfonimide (132 mg, 0.37 mmol). After 24 h the reaction was concentrated to yield a yellow semisolid and purified via Biotage chromatography with gradient elution from 100% hexanes to 25% EtOAc/hexanes to yield 91 mg (61%) of trifluoromethanesulfonic acid 3,5-dihydroxy-4-oxo-2-phenyl-4H-chromen-7-yl ester. Tf is CF₃SO₂—.

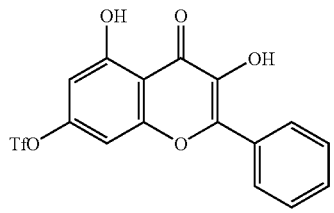

¹H NMR (CDCl₃, 400 MHz) δ 12.64 (s, 1H), 10.19 (s, 1H), 8.24 (d, 2H), 7.59–7.51 (c, 4H), 6.97 (d, 1H).

EXAMPLE 142

3,5-Dihydroxy-7-morpholin-4-yl-2-phenyl-chromen-4-one

A solution of trifluoromethanesulfonic acid 3,5-dihydroxy-4-oxo-2-phenyl-4H-chromen-7-yl ester (90 mg, 0.224 mmol), morpholine (0.024 mL, 0.269 mmol), tris(dibenzylideneacetone) dipalladium(0) (10 mg, 0.011 mmol), biphenyl-2-yl-di-tert-butyl-phosphane (13 mg, 0.045 mmol), and K₃PO₄ (67 mg, 0.314 mmol) in THF (1.2 mL) was capped and heated to 85° C. After 9 h, the reaction mixture was allowed to cool to room temperature, then filtered through a ½" silica gel (60 Å) plug. The plug was washed with EtOAc (40 mL) and the filtrate concentrated. The concentrate was purified via Biotage chromatography eluting with 100% CH₂Cl₂ to yield 7 mg (9%) of 3,5-dihydroxy-7-morpholin-4-yl-2-phenyl-chromen-4-one. Rf=0.22 (100% CH₂Cl₂).

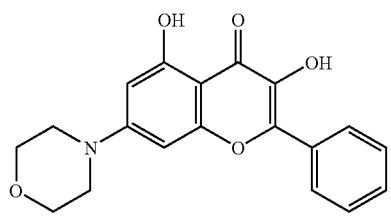

¹H NMR (CDCl₃, 400 MHz) δ 11.52 (s, 1H), 8.18 (d, 2H), 7.54–7.45 (c, 3H), 6.65(s, 1H), 6.38 (s, 1H), 6.32 (s, 1H), 3.84 (m, 4H), 3.38(m, 4H). LRMS (APCI, positive): Da/e 340.4 (m+1).

EXAMPLE 143

Trifluoromethanesulfonic acid 4-acetyl-3,5-dihydroxy-phenyl ester

A suspension of 1-(2,4,6-trihydroxyphenyl)-ethanone hydrate (5.0 g, 26.9 mmol), triethylamine (7.50 mL, 53.7 mmol) and crushed 4 Å molecular sieves was stirred in CH₂Cl₂ (250 mL). After 3 h, N-phenyltrifluoromethanesulfonimide (9.61 g, 26.9 mmol) was added in 10 portions (about 1 g each) over 5 hours. After 24 h, the reaction was filtered through a silica gel ¾" (60 Å) plug, and the plug washed with 5% MeOH/CH₂Cl₂ (200 mL). The filtrate was concentrated under reduced pressure, and the resulting oil purified via Biotage chromatography eluting with 15% EtOAc/hexanes to yield 590 mg (73%) of trifluoro-methanesulfonic acid 4-acetyl-3,5-dihydroxy-phenyl ester. Rf=0.50 (30% EtOAc/hexanes).

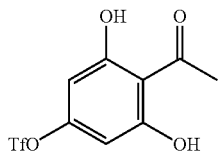

¹H NMR (CDCl₃, 400 MHz) δ 10.60 (s, 2H), 6.34 (s, 2H), 2.76 (s, 3H). ¹³C NMR (CDCl₃, 100 MHz) δ 205.5, 163.2, 153.9, 110.1, 101.8, 101.6, 33.5.

EXAMPLE 144

1-(2,6-Dihydroxy-4-morpholin-4-yl-phenyl)-ethanone

A solution of trifluoromethanesulfonic acid 4-acetyl-3,5-dihydroxy-phenyl ester (1.0 g, 3.33 mmol), morpholine (0.35 mL, 3.99 mmol), tris(dibenzylideneacetone) dipalladium(0) (153 mg, 0.167 mmol), biphenyl-2-yl-di-tert-butyl-phosphane (198 mg, 0.666 mmol), and K₃PO₄ (1.41 mg, 6.66 mmol) in THF (2 mL) was heated to 85° C. in a sealed tube for 2 h. The reaction mixture was allowed to cool to room temperature, and filtered through a ¾" silica gel (60 Å) plug. The plug was washed with EtOAc (75 mL) and the filtrate concentrated. The concentrate was purified via Biotage chromatography with gradient elution from 100% hexanes to 40% EtOAc/hexanes to yield 475 mg (60%) of 1-(2,6-dihydroxy-4-morpholin-4-yl-phenyl)-ethanone. Rf=0.16 (50% EtOAc/hexanes).

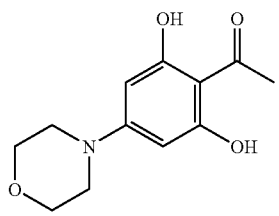

$^1$H NMR (CDCl$_3$, 400 MHz) δ 7.26 (s, 2H), 5.82 (s, 2H), 3.79 (c, 4H), 3.26 (m, 4H), 2.65 (s, 3H). LRMS (Electrospray, positive): Da/e 238.3 (m+1).

EXAMPLE 145

4-(5-Hydroxy-7-morpholin-4-yl-4-oxo-4H-chromen-2-yl)-benzonitrile

To a suspension of 1-(2,6-dihydroxy-4-morpholin-4-yl-phenyl)-ethanone (45 mg, 0.190 mmol) and K$_2$CO$_3$ (130 mg, 0.948 mmol) in acetone (3 mL) was added 4-cyanobenzoyl chloride 33 mg, 0.20 mmol). The reaction vessel was sealed and heated to 60° C. for 14 h. After cooling to room temperature, water (about 2 mL) was added, and the mixture was allowed to stir for about 10 min. The contents were transferred to a separatory funnel and extracted with EtOAc (3×15 mL). The organic layer was dried (MgSO$_4$) and concentrated. The concentrate was suspended in 50% EtOAc/hexanes and filtered to yield 1 mg (1%) of 4-(5-hydroxy-7-morpholin-4-yl-4-oxo-4H-chromen-2-yl)-benzonitrile.

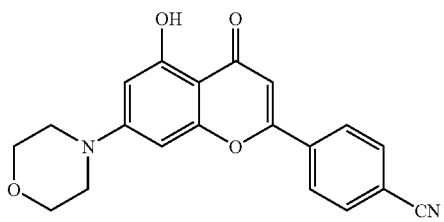

$^1$H NMR (CDCl$_3$, 400 MHz) δ 12.40 (s, 1H), 7.98 (d, 1H), 7.81 (d, 1H), 6.67 (s, 1H) 6.4 (s, 1H), 6.31 (s, 1H), 3.90 m, 4H), 3.37 (m, 4H).

EXAMPLE 146

3-(5-Hydroxy-7-morpholin-4-yl-4-oxo-4H-chromen-2-yl)-benzonitrile

To a suspension of 1-(2,6-dihydroxy-4-morpholin-4-yl-phenyl)-ethanone (61 mg, 0.257 mmol) and K$_2$CO$_3$ (178 mg, 1.29 mmol) in acetone (3 mL) was added 3-cyanobenzoyl chloride (43 mg, 0.257 mmol). The reaction vessel was sealed and heated to 60° C. for 2 d. After cooling to room temperature, water (about 2 mL) was added, and the mixture was allowed to stir for about 10 min. The contents were transferred to a separatory funnel containing water (5 mL) and extracted with EtOAc (3×15 mL). The organic layer was dried (MgSO$_4$) and concentrated. The concentrate was purified via Biotage chromatography with gradient elution from 100% hexanes to 30% EtOAc/hexanes to yield 6 mg (7%) of 3-(5-hydroxy-7-morpholin-4-yl-4-oxo-4H-chromen-2-yl)-benzonitrile. Rf=0.33 (50% EtOAc/hexanes).

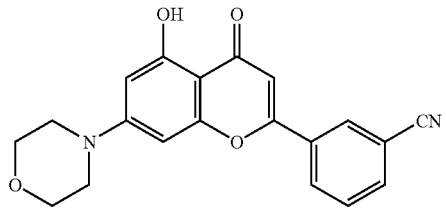

$^1$H NMR (CDCl$_3$, 400 MHz) δ 12.40 (s, 1H), 8.20 (s, 1H), 8.05 (d, 1H), 7.81 (d, 1H), 7.66 (dd, 1H), 6.64 (s, 1H), 6.41 (s, 1H), 6.31 (s, 1H), 3.87 (m, 4H), 3.38 (m, 4H). LRMS (APCI, positive): Da/e 349.4 (m+1).

EXAMPLE 147

5-Hydroxy-2-(4-methoxyphenyl)-7-morpholin-4-yl-chromen-4-one

To a suspension of 1-(2,6-dihydroxy-4-morpholin-4-yl-phenyl)-ethanone (112 mg, 0.472 mmol) and K$_2$CO$_3$ (326 mg, 2.36 mmol) in acetone (3 mL) was added p-anisoyl chloride (0.066 mL, 0.472 mmol). The reaction vessel was sealed and heated to 80° C. for 4 days. After cooling to room temperature, water (about 2 mL) was added, and the mixture was allowed to stir for about 15 min. The contents were transferred to a separatory funnel containing water (5 mL) and extracted with EtOAc (3×15 mL). The organic layer was dried (MgSO$_4$) and concentrated. The concentrate was purified via Biotage chromatography with gradient elution from 100% hexanes to 30% EtOAc/hexanes to yield 9 mg (5%) of 5-hydroxy-2-(4-methoxy-phenyl)-7-morpholin-4-yl-chromen-4-one. Me is CH$_3$—.

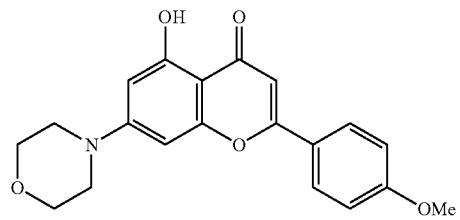

$^1$H NMR (CDCl$_3$, 400 MHz) δ 12.67 (s, 1H), 7.83 (d, 2H), 7.00 (d, 2H), 7.81 (d, 1H), 6.54 (s, 1H), 6.37(d, 1H), 6.29 (d, 1H), 3.89 (s, 3H), 3.86 (m, 4H), 3.34 (m, 4H). LRMS (Electrospray, positive): Da/e 354.6 (m+1).

EXAMPLE 148

5-Hydroxy-7-morpholin-4-yl-2-pyridin-3-yl-chromen-4-one

To a suspension of 1-(2,6-dihydroxy-4-morpholin-4-yl-phenyl)-ethanone (86 mg, 0.362 mmol) and K$_2$CO$_3$ (250 mg, 1.81 mmol) in acetone (3 mL) was added nicotinoyl chloride hydrochloride (0.71 mL, 0.399). The reaction vessel was sealed and heated to 85° C. for 24 h. After cooling to room temperature, water (about 2 mL) was added, and the mixture was allowed to stir for about 10 min. The contents were transferred to a separatory funnel containing water (5 mL) and extracted with EtOAc (3×15 mL). The organic layer was dried (MgSO$_4$) and concentrated. The concentrate was purified via Biotage chromatography with gradient elution from 100% hexanes to 100% EtOAc to yield 14 mg (12%) of 5-hydroxy-7-morpholin-4-yl-2-pyridin-3-yl-chromen-4-one. Rf=0.22 (100% EtOAc).

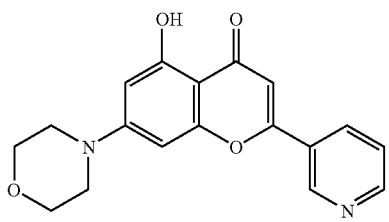

$^1$H NMR (CDCl$_3$, 400 MHz) δ 12.44 (s, 1H), 9.12 (s, 1H), 8.76 (d, 1H), 8.13 (d, 1H), 7.47 (m, 1H), 6.64 (s, 1H), 6.39 (d, 1H), 6.30 (s, 1H), 3.86 (m, 4H), 3.36 (m, 4H). LRMS (Electrospray, positive): Da/e 325.6 (m+1).

EXAMPLE 149

2-Hydroxy-1-(2-hydroxy-4-morpholin-4-yl-phenyl)-ethanone 1-(2-Hydroxy-4-morpholin-4-yl-phenyl)-ethanone was dissolved in triethylamine (12 mL), and trimethylsilyl chloride (1.60 mL, 12.6 mmol) was added dropwise while maintaining the temperature of the solution below 35° C. A solution of sodium iodide (0.54 g, 3.62 mmol) dissolved in acetonitrile (30 mL) was added dropwise without allowing the temperature to rise above 35° C. The reaction was stirred at 22° C. for 16 hours, then poured into ice water/hexanes. The layers were separated and the aqueous layer was washed with hexanes (2×). The combined organics were dried over K$_2$CO$_3$ and concentrated in vacuo. This material, 4-(3-trimethylsilanyloxy-4-(1-trimethylsilanyloxy-vinyl)-phenyl]-morpholine, ($^1$H NMR (CDCl$_3$, 400 MHz): δ 7.42 (d, 1H), 6.53–6.49 (m, 1H), 6.33–6.31 (d, 1H), 5.06 (s, 1H), 4.53 (s, 1H), 3.87–3.83 (m, 4H), 3.16–3.11 (m, 4H), 0.28 (s, 9H), 0.23 (s, 9H)), was used in the reaction below.

3-Chloroperoxybenzoic acid (1.48 g, 6.0 mmol) was slurried in hexanes (40 mL) and cooled to −78° C. A solution of 4-(3-trimethylsilanyloxy-4-(1-trimethylsilanyloxy-vinyl)-phenyl]-morpholine (1.10 g, 3.01 mmol) dissolved in hexanes (5 mL) was added slowly. The resulting suspension was maintained at −78° C. for 60 minutes then slowly warmed to 22° C. After stirring at 22° C. for 16 hours, the reaction mixture was diluted with methanol and concentrated in vacuo. The residue was redissolved in methanol and concentrated two additional times. The solids were resuspended in EtOAc and washed 2 times with saturated NaHCO$_3$, and once with saturated NaCl then dried over Na$_2$SO$_4$. After concentration, the residue was chromatographed on SiO2 using 2:1 hexane/EtOAc then 1:1 hexane/EtOAc. After concentration, the alcohol was recrystallized from EtOAc. (19% yield).

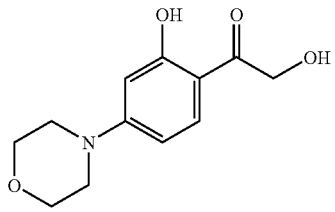

$^1$H NMR (CDCl$_3$, 400 MHz): δ 11.86 (s, 1H), 7.38 (m, 1H), 6.40 (m, 1H), 6.31 (s, 1H), 4.76 (d, 1H), 3.86–3.80 (m, 4H), 3.38–3.32 (m, 4H). $^{13}$C NMR (CDCl$_3$, 100 MHz): d 199.1, 164.5, 157.0, 130.0, 108.7, 106.1, 100.3, 66.5, 63.7, 47.0. LRMS (Electrospray, negative): Da/e 236.4 (m−1).

Obviously, many modifications and variations of the invention as hereinbefore set forth can be made without departing from the spirit and scope thereof, and, therefore, only such limitations should be imposed as are indicated by the appended claims.

What is claimed is:

1. A compound having a formula

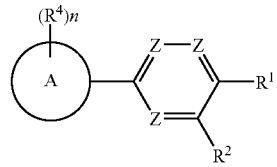

or a pharmaceutically acceptable salt thereof, wherein:

n is an integer 0 through 2;

R$^1$ is selected from the group consisting of carboxy, cyano, thiocarboxamide, R$^a$C(=O)—;

R$^2$ is OH; or

R$^1$ and R$^2$ are taken together with the carbon atoms to which each is attached to form a monocyclic 5- or 6-membered partially saturated ring, wherein 1, 2, or 3 carbon atoms of R$^1$ and R$^2$ optionally are a heteroatom selected from the group consisting of O, N, S, and P, said ring optionally substituted with one or more =O, =S, =NH, OR$^h$, N(R$^h$)$_2$, aryl, substituted aryl, heteroaryl, or substituted heteroaryl, said nitrogen or phosphorus heteroatom optionally substituted with a group consisting of aryl, substituted aryl, alkyl, alkyl substituted with R$^a$C(=O), and R$^a$C (=O)

R$^3$, independently, is selected from the group consisting of hydrogen, sulfonamido, sulfamyl, sulfonyl chloride, and sulfo;

wherein R$^a$ is selected from the group consisting of alkyl, substituted alkyl, cycloalkyl, heteroaryl, substituted heteroaryl, heterocycloalkyl, and substituted heterocycloalkyl;

wherein R$^h$, independently, is selected from the group consisting of hydrogen, alkyl, substituted alkyl, cycloalkyl, aryl, substituted aryl, heteroaryl, and substituted heteroaryl; and R$^4$, independently, is selected from the group consisting of OR$^h$, alkyl, substituted alkyl, aryl, and substituted aryl;

and wherein cycloalkyl is a nonaromatic cyclic hydrocarbon group having three to six carbon atoms;

heterocycloalkyl is a monocyclic, bicyclic, or tricyclic nonaromatic partially unsaturated or saturated ring system having 3 to 10 members and having one to four heteroatoms independently selected from the group consisting of oxygen, nitrogen, and sulfur;

heteroaryl is a cyclic aromatic ring system having five- to ten-ring atoms, wherein one- to four-ring atoms independently are selected from the group consisting of oxygen, nitrogen, and sulfur, and the remaining ring atoms are carbon;

substituted alkyl is an alkyl group having a substituent selected from the group consisting of cycloalkyl, aryl, heteroaryl, heterocycloalkyl, substituted aryl, substituted heteroaryl, substituted heterocycloalkyl, $N(R^h)_2$, $OR^h$, $SR^h$, sulfoxide, sulfonyl, halo, $R^aC(=O)$, carboxy, hydrazino, hydrazono, and hydroxy-amino;

substituted aryl is an aryl group having one to three substituents selected from the group consisting of halo, $OR^h$, $N(R^h)_2$, CN, alkyl, substituted alkyl, mercapto, nitro, CHO, carboxy, carboxamide, aryl, heteroaryl, cycloalkyl, heterocycloalkyl, $O(CH_2)_{1-3}N(R^h)_2$, $O(CH^2)_{1-3}CO_2H$, and trifluoromethyl;

substituted heteroaryl is a heteroaryl group having one to three substituents selected from the group consisting of halo, $OR^h$, $N(R^h)_2$, CN, alkyl, substituted alkyl, mercapto, nitro, CHO, carboxy, carboxamide, aryl, heteroaryl, cycloalkyl, heterocycloalkyl, $O(CH_2)_{1-3}N(R^h)_2$, $O(CH_2)_{1-3}CO_2H$, and trifluoromethyl; and substituted heterocycloalkyl is a heterocycloalkyl group having one to three substituents selected from the group consisting of halo, $OR^h$, $N(R^h)_2$, CN, alkyl, substituted alkyl, mercapto, nitro, CHO, carboxy, carboxamide, aryl, heteroaryl, cycloalkyl, heterocycloalkyl, $O(CH_2)_{1-3}N(R^h)_2$, $O(CH_2)_{1-3}CO_2H$, and trifluoromethyl.

2. The compound of claim 1 wherein $R^1$ is selected from the group consisting of —C≡N, —(CO)—OH, —(CO)—O—$CH_3$, —(CO)—$CF_3$, —(CO)-alkyl, —(CO)-substituted alkyl, —(CO)-heteroaryl, and —(CO)—$CH_2$—$N(R^h)_2$.

3. A compound having a formula:

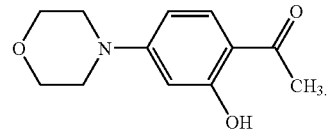

4. The compound of claim 1, wherein $R^1$ is selected from the group consisting of carboxy, cyano, thiocarboxamide, $R^aC(=O)$, and $R^2$ is OH.

5. The compound of claim 4, wherein n is 0.

6. The compound of claim 4, wherein $R^3$ is H.

7. The compound of claim 4, wherein n is 0 and $R^3$ is H.

* * * * *

UNITED STATES PATENT AND TRADEMARK OFFICE
CERTIFICATE OF CORRECTION

| | | |
|---|---|---|
| PATENT NO. | : 7,179,912 B2 | Page 1 of 1 |
| APPLICATION NO. | : 09/941897 | |
| DATED | : February 20, 2007 | |
| INVENTOR(S) | : James W. Halbrook et al. | |

It is certified that error appears in the above-identified patent and that said Letters Patent is hereby corrected as shown below:

On The Title Page, Item (73)
Assignee: should be changed from "ICOS Corporation, Bothell, WA (US)" to -- Luitpold Pharmaceuticals, Inc., One Luitpold Drive, Shirley, NY (US) --

Col. 118,
In Claim 1, lines 25-30, delete the formula:

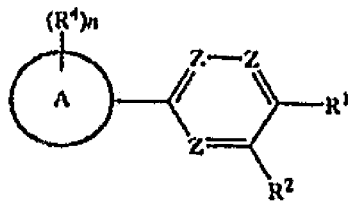

and replace with

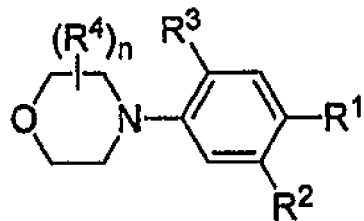

Signed and Sealed this

Twenty-eighth Day of August, 2007

JON W. DUDAS
*Director of the United States Patent and Trademark Office*